(12) United States Patent
Hechler et al.

(10) Patent No.: US 12,403,201 B2
(45) Date of Patent: Sep. 2, 2025

(54) B-LYMPHOCYTE SPECIFIC AMATOXIN ANTIBODY CONJUGATES

(71) Applicant: Heidelberg Pharma Research GmbH, Ladenburg (DE)

(72) Inventors: Torsten Hechler, Ladenburg (DE); Michael Kulke, Ladenburg (DE); Andreas Pahl, Ladenburg (DE)

(73) Assignee: Heidelberg Pharma Research GmbH, Ladenburg (DE)

( * ) Notice: Subject to any disclaimer, the term of this patent is extended or adjusted under 35 U.S.C. 154(b) by 0 days.

(21) Appl. No.: 17/697,583

(22) Filed: Mar. 17, 2022

(65) Prior Publication Data

US 2022/0370632 A1 Nov. 24, 2022
US 2025/0090678 A2 Mar. 20, 2025

(30) Foreign Application Priority Data

Mar. 19, 2021 (EP) .................................... 21163784

(51) Int. Cl.
*A61K 47/68* (2017.01)
*A61P 35/00* (2006.01)
*A61P 37/06* (2006.01)

(52) U.S. Cl.
CPC ...... *A61K 47/6831* (2017.08); *A61K 47/6849* (2017.08); *A61P 35/00* (2018.01); *A61P 37/06* (2018.01)

(58) Field of Classification Search
None
See application file for complete search history.

(56) References Cited

U.S. PATENT DOCUMENTS

| | | | |
|---|---|---|---|
| 4,880,935 A | 11/1989 | Thorpe | |
| 5,122,368 A | 6/1992 | Greenfield et al. | |
| 5,622,929 A | 4/1997 | Willner et al. | |
| 5,824,805 A | 10/1998 | King et al. | |
| 5,859,205 A | 1/1999 | Adair et al. | |
| 6,548,640 B1 | 4/2003 | Winter | |
| 7,491,532 B2 | 2/2009 | Bout et al. | |

(Continued)

FOREIGN PATENT DOCUMENTS

| | | |
|---|---|---|
| JP | 2018-513120 A | 5/2018 |
| WO | 2006/121168 A1 | 11/2006 |

(Continued)

OTHER PUBLICATIONS

Witkowska et al., Expert Opinion on Investigational Drugs, 2018 vol. 27, No. 2, 171-177 (Year: 2018).*

(Continued)

*Primary Examiner* — Karl J Puttlitz
(74) *Attorney, Agent, or Firm* — Grüneberg and Myers PLLC

(57) ABSTRACT

The present application relates to conjugates comprising an amatoxin a target-binding moiety wherein the target is CD37, i.e., a CD37-binding moiety, and optionally a linker linking said amatoxin and said CD37-binding moiety. The invention further relates to the synthesis of said conjugates. In addition, the invention relates to a pharmaceutical composition comprising such conjugate for use in the treatment of immune cell-, particularly B-cell and/or lymphoma associated diseases and/or malignancies.

8 Claims, 39 Drawing Sheets

Specification includes a Sequence Listing.

| | $R_1$ | $R_2$ | $R_3$ | $R_4$ |
|---|---|---|---|---|
| α-amanitin | OH | OH | $NH_2$ | OH |
| β-amanitin | OH | OH | OH | OH |
| γ-amanitin | H | OH | $NH_2$ | OH |
| ε-amanitin | H | OH | OH | OH |
| amanin | OH | OH | OH | H |
| amaninamide | OH | OH | $NH_2$ | H |
| amanullin | H | H | $NH_2$ | OH |
| amanullinic acid | H | H | OH | OH |
| γ-amanin | H | OH | OH | H |
| γ-amaninamide | H | OH | NH2 | H |

(56) References Cited

U.S. PATENT DOCUMENTS

| | | | |
|---|---|---|---|
| 8,008,449 | B2 | 8/2011 | Korman et al. |
| 8,354,509 | B2 | 1/2013 | Carven et al. |
| 2010/0311116 | A1 | 12/2010 | Wurm et al. |
| 2012/0100161 | A1* | 4/2012 | Faulstich .................. A61P 1/16 |
| | | | 424/183.1 |
| 2016/0002298 | A1* | 1/2016 | Müller .................. C07K 16/32 |
| | | | 514/19.9 |
| 2017/0349666 | A1 | 12/2017 | Klein et al. |
| 2018/0043033 | A1* | 2/2018 | Anderl .................... A61P 43/00 |
| 2019/0218308 | A1 | 7/2019 | Chanteux et al. |
| 2020/0407440 | A1* | 12/2020 | McDonagh ............. A61P 35/00 |
| 2022/0133902 | A1 | 5/2022 | Kulke et al. |
| 2023/0135930 | A1 | 5/2023 | McDonagh et al. |
| 2025/0009901 | A1 | 1/2025 | Kulke et al. |
| 2025/0064960 | A1 | 2/2025 | Hechler et al. |

FOREIGN PATENT DOCUMENTS

| | | | |
|---|---|---|---|
| WO | 2009/007861 | A1 | 1/2009 |
| WO | 2009/101611 | A1 | 8/2009 |
| WO | 2009/114335 | A2 | 9/2009 |
| WO | 2010/115629 | A2 | 10/2010 |
| WO | 2011092295 | * | 8/2011 |
| WO | 2012/041504 | A1 | 4/2012 |
| WO | 2013088363 | * | 6/2013 |
| WO | WO 2013/088363 | A1 | 6/2013 |
| WO | 2014/043403 | A1 | 3/2014 |
| WO | 2014/135282 | A1 | 9/2014 |
| WO | 2015/033301 | A1 | 3/2015 |
| WO | 2016/142049 | A1 | 9/2016 |
| WO | 2017/149077 | A1 | 9/2017 |
| WO | 2017/210288 | A1 | 12/2017 |
| WO | 2018/115466 | A1 | 6/2018 |
| WO | 2018/134787 | A2 | 7/2018 |
| WO | 2018/220169 | A1 | 12/2018 |
| WO | 2019/030171 | A1 | 2/2019 |
| WO | 2019/030173 | A1 | 2/2019 |
| WO | 2019/197654 | A1 | 10/2019 |
| WO | WO 2020/216947 | A1 | 10/2020 |
| WO | WO 2022/096604 | A1 | 5/2022 |

OTHER PUBLICATIONS

Pereira et al., Mol Cancer Ther. Jul. 2015; 14(7): 1650-1660 (Year: 2015).*

Deckert et al., Blood. 2013;122(20):3500-3510 (Year: 2013).*

Pardoll et al., Nat Rev Cancer 12, 252-264 (2012) (Year: 2012).*

Stathis et al., "Safety, Tolerability, and Preliminary Activity of IMGN529, a CD37-targeted Antibody-Drug Conjugate, in Patients with Relapsed or Refractory B-cell non-Hodgkin Lymphoma: a Dose-escalation, Phase I Study," *Invest. New Drugs*., 36(5): 869-876 (2018).

Vaisitti et al., "Anti-CD37 Alpha-Amanitin Conjugated Antibodies as Therapeutic Weapons for Richter's Syndrome," *Blood.*, 138(Suppl. 1): 791-792 (2021).

Voss et al., "Preclinical Evaluation of Anti-CD37 Antibody-targeted Amanitin Conjugates (ATAC) in B-cell Malignancies," *Cancer Res.*, 81(Suppl. 13): 915 (2021).

Cormedi et al., "Predicting immunotherapy response through genomics", Current opinion in Genetics & Development, vol. 66, Feb. 2021, pp. 1-9.

Communication pursuant to Article 94(3) EPC received for European Patent Application No. 20724752.9, mailed on Jun. 27, 2024, 4 pages.

Darvin et al., "Immune checkpoint inhibitors: recent progress and potentia biomarkers", Experimental and Molecular Medicine, vol. 50, No. 165, Dec. 13, 2018. pp. 1-11.

Edwards et al., "The Remarkable Flexibility of the Human Antibody Repertoire; Isolation of Over One Thousand Different Antibodies to a Single Protein, BLyS", J. Mol. Biol., vol. 334, No. 1, Nov. 14, 2003, pp. 103-118.

International Search Report received for PCT Application No. PCT/EP2020/061555, mailed on Aug. 18, 2020, 6 pages.

Kroemer et al., "Immunogenic Cell Death in Cancer Therapy", Annu. Rev. Immunol., vol. 31, 2013, pp. 51-72.

Li et al., "A Mini-Review for Cancer Immunotherapy: Molecular Understanding of PD-1/PD-L1 Pathway & Translational Blockade of Immune Checkpoints", Int. J. Mo. Sci., vol. 17, No. 1151, Jul. 18, 2016, pp. 1-22.

Lloyd et al., "Modelling the human immune response: performance of a $10^{11}$ human antibody repertoire against a broad panel of therapeutically relevant antigens", Protein Engineering, Design & Selection, vol. 22, No. 3, Oct. 29, 2008, pp. 159-168.

Marshall et al., "Immuno-Oncology: Emerging Targets and Combination Therapies", Frontiers in Oncology, vol. 8, Article 315, Aug. 23, 2018, pp. 1-29.

Martins et al., "Adverse effects of immune-checkpoint inhibitors: epidemiology, management and surveillance", Nat. Rev. Clin. Oncol., vol. 16, No. 9, Sep. 2019, pp. 563-580.

Martin E. Hemler, "Specific tetraspanin functions", The Journal of Cell Biology, vol. 155, No. 7, Dec. 24, 2001, pp. 1103-1107.

Obeid et al., "Calreticulin exposure dictates the immunogenicity of cancer cell death", Nat. Med., vol. 13, No. 1, Jan. 2007, pp. 54-61.

Office Action received for U.S. Appl. No. 17/518,911, mailed on Mar. 6, 2024, 41 pages.

Office Action received for U.S. Appl. No. 17/046,497, mailed on Mar. 26, 2024, 27 pages.

Office Action for U.S. Appl. No. 17/518,911, mailed on Jul. 20, 2023, 34 pages.

Office Action received for Japanese Patent Application No. 2021-562940, mailed on Aug. 20, 2024, 6 pages with English Translation.

Office Action received for Japanese Patent Application No. 2021-562940, mailed on Nov. 7, 2023, 14 pages with English Translation.

Qin et al., "Novel immune checkpoint targets: moving beyond PD-1 and CTLA-4", Mol. Cancer, vol. 18, No. 155, Nov. 6, 2019, pp. 1-14.

Sambi et al., "Current Challenges in Cancer Immunotherapy: Multimodal Approaches to Improve Efficacy and Patient Response Rates", J. Oncol., Feb. 28, 2019, pp. 1-13.

Singh et al., "Immune checkpoint inhibitors: a promising anticancer therapy", Drug Discov. Today, vol. 25, No. 1, Jan. 2020, pp. 223-229.

Strop et al., "Location matters: site of conjugation modulates stability and pharmacokinetics of antibody drug conjugates", Chemistry and Biology, vol. 20, Feb. 21, 2013, pp. 161-167.

Search Report received for Singaporean Patent Application No. 11202110287Q mailed on Nov. 26, 2023, 6 pages.

Taams et al., "Immune checkpoint inhibition: from molecules to clinical application", Clinical and Experimental Immunology., vol. 200, No. 2, 2020, pp. 105-107.

Wei et al., "Fundamental Mechanisms of Immune Checkpoint Blockade Therapy", Cancer Discov., vol. 8, No. 9, Aug. 16, 2018, pp. 1069-1086.

Wieland et al., "Amatoxins, Phallotoxins, Phallolysin, and Antamanide: The Biologically Active Components of Poisonous Amanita Mushroom", Critical Review in Biochem., vol. 5, No. 3, Dec. 1978, pp. 185-260.

Wu et al., "Humanization of a Murine Monoclonal Antibody by Simultaneous Optimization of Framework and CDR Residues", J. Mol. Biol., vol. 294, Issue 1, Nov. 19, 1999, pp. 151-162.

Written Opinion received for PCT Application No. PCT/EP2020/061555, mailed on Aug. 18, 2020, 7 pages.

Written Opinion received for Singaporean Patent Application No. 11202110287Q, mailed on Nov. 27, 2023, 10 pages.

Xu-Monette et al., "Assessment of CD37 B-cell antigen and cell of origin significantly improves risk prediction in diffuse large B-cell lymphoma", Blood., vol. 128, No. 26, Dec. 29, 2016, pp. 3083-3100.

Zou et al., "Expression and Function of Tetraspanins and Their Interacting Partners in B Cells", Front. Immunol., vol. 9, Article 1606, Jul. 18, 2018, pp. 1-17.

Almagro et al., "Humanization of antibodies", Frontiers in Bioscience, vol. 13, Jan. 1, 2008, pp. 1619-1633.

(56) References Cited

OTHER PUBLICATIONS

Altschul et al., "Basic Local Alignment Search Tool", J. Mol. Biol., vol. 215, May 15, 1990, pp. 403-410.
Altschul et al., "Gapped Blast and PSI-Blast: a new generation of protein database search programs", Nucleic Acids Research, vol. 25, No. 17, Jul. 16, 1997, pp. 389-3402.
Bargh et al., "Cleavable linkers in antibody-drug conjugates", Chem. Soc. Rev., vol. 48, Apr. 9, 2019, pp. 4361-4374.
Beckwith et al., "The CD37-targeted antibody-drug conjugate IMGN529 is highly active against human CLL and in a novel CD37 transgenic murine leukemia model", Leukemia, vol. 28, No. 7, Jul. 2014, pp. 1501-1510.
Behrens et al., "Antibody-Drug Conjugates (ADCs) Derived from Interchain Cysteine Cross-Linking Demonstrate Improved Homogeneity and Other Pharmacological Properties over Conventional Heterogeneous ADCs", Mol. Pharm., vol. 12, No. 11, Nov. 2, 2015, pp. 3986-3998.
Belov et al., "Immunophenotyping of Leukemias Using a Cluster of Differentiation Antibody Microarray", Cancer Research, vol. 61, Jun. 1, 2001, pp. 4483-4489.
Binz et al., "Engineering novel binding proteins from nonimmunoglobulin domains", Nature Biotechnology, vol. 23, No. 10, Oct. 6, 2005, pp. 1257-1268.
Buchman et al., "Comparison of Intron-Dependent and Intron-Independent Gene Expression", Mol. Cell. Biol. vol. 8, No. 10, Jul. 11, 1988, pp. 4395-4405.
Chothia et al., "Canonical structures for the Hypervariable Regions of Immunoglobulins", J. Mol. Biol., vol. 196, Apr. 23, 1987, pp. 901-917.
"Compendium of Chemical Terminology", Published by the International Union of Pure and Applied Chemistry, Feb. 24, 2014, pp. 1-1622.
Costa et al., "Guidelines to cell engineering for monoclonal antibody production", Eur. J. Pharm. Biopharm., vol. 74, Oct. 22, 2009, pp. 127-138.
David W. Womble, "GCG: The Wisconsin Package of sequence analysis programs", Methods in Molecular Biology, vol. 132, 2000, pp. 3-22.
Deuereux et al., "A comprehensive set of sequence analysis programs for the VAX", Nucleic Acids Research, vol. 12, No. 1, Aug. 18, 1983, pp. 387-395.
Dubowchik et al., "Receptor-mediated and enzyme-dependent targeting of cytotoxic anticancer drugs", Pharmacology & Therapeutics, vol. 83, No. 2, Aug. 1999, pp. 67-123.
Dubowchik et al., "Cathepsin B-Labile Dipeptide Linkers for Lysosomal Release of Doxorubicin from Internalizing Immunoconjugates: Model Studies of Enzymatic Drug Release and Antigen-Specific In Vitro Anticancer Activity", Bioconjugate Chem., vol. 13, Apr. 30, 2002, pp. 855-869.
Edelman et al., "The covalent structure of an entire γGimmunoglobulin molecule", Proc. Natl. Acad. Sci. USA, vol. 63, Mar. 21, 1969, pp. 78-85.
English et al., "Ancient species offers contemporary therapeutics: an update on shark $V_{NAR}$ single domain antibody sequences, phage libraries and potential clinical applications", Antibody Therapeutics, vol. 3, No. 1, 1969, pp. 1-9.
Filho et al., "Blood group antigen studies using CdTe quantum dots and flow cytometry", International Journal of Nanomedicine, vol. 10, Jul. 8, 2015, pp. 4393-4404.
Furman et al., "Ibrutinib Resistance in Chronic Lymphocytic Leukemia", N. Engl. J. Med., vol. 370, No. 24, Jun. 12, 2014, pp. 1-4.
George et al., "Ibrutinib Resistance Mechanisms and Treatment Strategies for B-Cell Lymphomas", Cancers, vol. 12, No. 1328, May 22, 2020, pp. 1-31.
Hamid et al., "Safety and Tumor Responses with Lambrolizumab (Anti-PD-1) in Melanoma", The New England Journal of Medicine, vol. 369, No. 2, Jul. 11, 2013, pp. 134-144.
Jäger et al., "High level transient production of recombinant antibodies and antibody fusion proteins in HEK293 cells", BMC Biotechnology, vol. 13, No. 52, Jun. 26, 2013, pp. 1-20.

Jennifer R. Brown, "How I treat CLL patients with ibrutinib", Blood, vol. 131, No. 4, Jan. 25, 2018, pp. 379-386.
Junutula et al., "Site-specific conjugation of a cytotoxic drug to an antibody improves the therapeutic index", Nature Biotechnology, vol. 26, No. 8, Jul. 20, 2008, pp. 925-932.
Kamat et al., "Designing binding kinetic assay on the bio-layer interferometry (BLI) biosensor to characterize antibody-antigen interactions", Analytical Biochemistry, vol. 536, Aug. 10, 2017, pp. 16-31.
Karlin et al., "Applications and statistics for multiple high-scoring segments in molecular sequences", Proc. Natl. Acad. Sci. USA, vol. 90, Mar. 24, 1993, pp. 5873-5877.
Kim et al., "Use of the human elongation factor 1 α promoter as a versatile and efficient expression system", Gene, vol. 91, No. 2, Feb. 10, 1990, pp. 217-223.
Knobeloch et al., "Targeted inactivation of the tetraspanin CD37 impairs T-cell-dependent B-cell response under suboptimal costimulatory conditions", Mol. Cell. Biol., vol. 20, No. 15, Apr. 17, 2000, pp. 5363-5369.
Lapalombella et al., "Tetraspanin CD37 directly mediates transduction of survival and apoptotic signals", Cancer Cell., vol. 21, No. 5, May 25, 2012, pp. 694-708.
Lefranc et al., "IMGT unique numbering for immunoglobulin and T cell receptor variable domains and Ig superfamily V-like domains", Developmental and Comparative Immunology, vol. 27, May 29, 2002, pp. 55-77.
Link et al., "A unique antigen on mature B cells defined by a monoclonal antibody", J. Immunol., vol. 137, No. 9, Nov. 1, 1986, pp. 3013-3018.
Liu et al., "TP53 loss creates therapeutic vulnerability in colorectal cancer", Nature, vol. 520, No. 7549, Apr. 30, 2015, pp. 697-701.
Merz et al., "Baseline characteristics, chromosomal alterations, and treatment affecting prognosis of deletion 17p in newly diagnosed myeloma", American Journal of Hematology, vol. 91, No. 11, Nov. 2016, pp. E473-E477.
Neville et al., "Enhancement of Immunotoxin Efficacy by Acid-cleavable Cross-linking Agents Utilizing Diphtheria Toxin and Toxin Mutants", The Journal of Biological Chemistry, vol. 264, No. 25, Sep. 5, 1989, pp. 14653-14661.
Noy-Porat et al., "Characterization of antibody-antigen interactions using biolayer interferometry", Star Protocols, vol. 2, No. 100836, Dec. 17, 2021, pp. 1-14.
Paul Carter, "Site-directed mutagenesis", Biochem. J., vol. 237, pp. 1-7, 1986.
Pearson et al., "Improved tools for biological sequence comparison", Proc. Natl. Acad. Sci. USA, vol. 85, Apr. 1988, pp. 2444-2448.
Pillow et al., "Decoupling stability and release in disulfide bonds with antibody-small molecule conjugates", Chem. Sci., vol. 8, No. 1, Apr. 26, 2016, pp. 366-370.
Pula et al., "Overcoming Ibrutinib Resistance in Chronic Lymphocytic Leukemia", Cancers, vol. 11, No. 1834, Nov. 21, 2019, pp. 1-24.
Rajkumar et al., "Multiple myeloma current treatment algorithms", Blood Cancer Journal, vol. 10, No. 94, Sep. 28, 2020, pp. 1-10.
Saiz et al., "Tetraspanins as Organizers of Antigen-Presenting Cell Function", Frontiers in Immunology, Voume 9, Article 1074, May 23, 2018, pp. 1-12.
Schwartz-Albiez et al., "The B cell-associated CD37 antigen (gp40-52) Structure and subcellular expression of an extensively glycosylated glycoprotein", J. Immunol., vol. 140, No. 3, Feb. 1, 1988, pp. 905-914.
Smeland et al., "Characterization of Two Murine Monoclonal Antibodies Reactive with Human B Cells, Their use in a high-yield, high-purity method for isolation of B cells and utilization of such cells in an assay for B-cell stimulating factor", Scand. J. Immunol., vol. 21, No. 3, Oct. 8, 1984, pp. 205-214.
Smith et al., "Identification of common molecular subsequences", J. Mol. Biol., vol. 147, No. 1, Mar. 25, 1981, pp. 195-197.
Spangler et al., "Toward a Ferrous Iron-Cleavable Linker for Antibody-Drug Conjugates", Mol. Pharm., vol. 15, No. 5, Mar. 23, 2018, pp. 2054-2059.
Stacchini et al., "MEC1 and MEC2: two new cell lines derived from B-chronic lymphocytic leukaemia in prolymphocytoid transformation", Leukemia Research, vol. 23, Aug. 29, 1998, pp. 127-136.

(56) References Cited

OTHER PUBLICATIONS

Stilgenbauer et al., "Phase 1 first-in-human trial of the anti-CD37 antibody BI 836826 in relapsed/refractory chronic lymphocytic leukemia", Leukemia, vol. 33, No. 10, May 14, 2019, pp. 2531-2535.

Thorpe et al., "New Coupling Agents for the Synthesis of Immunotoxins Containing a Hindered Disulfide Bond with Improved Stability in Vivo", Cancer Research, vol. 47, Nov. 15, 1987, pp. 5924-5931.

Tsimberidou et al., "Phase I-II study of oxaliplatin, fludarabine, cytarabine, and rituximab combination therapy in patients with Richter's syndrome or fludarabine-refractory chronic lymphocytic leukemia", J. Clin. Oncol., vol. 26, No. 2, Jan. 10, 2008, pp. 196-203.

Vaisitti et al., "Novel Richter Syndrome Xenograft Models to Study Genetic Architecture, Biology, and Therapy Responses", Cancer Research, vol. 78, No. 13, Jul. 1, 2018, pp. 3413-3420.

Van Spriel et al., "A Regulatory Role for CD37 in T Cell Proliferation", The Journal of Immunology, vol. 172, No. 5, Dec. 18, 2003, pp. 2953-2961.

Villalba et al., "Site-directed Mutagenesis Reveals Regions Implicated in the Stability and Fiber Formation of Human λ3r Light Chains", The Journal of Bioloical Chemist , vol. 290, No. 5, Jan. 30, 2015, pp. 2577-2592.

William R. Pearson, "Rapid and Sensitive Sequence Comparison with FASTP and FASTA", Methods in Enzymology, vol. 183, 1990, pp. 63-98.

Zhao et al., "Targeting CD37-positive lymphoid malignancies with a novel engineered small modular immunopharmaceutical", Blood, vol. 110, No. 7, Oct. 1, 2007, pp. 2569-2577.

* cited by examiner

| | $R_1$ | $R_2$ | $R_3$ | $R_4$ |
|---|---|---|---|---|
| α-amanitin | OH | OH | $NH_2$ | OH |
| β-amanitin | OH | OH | OH | OH |
| γ-amanitin | H | OH | $NH_2$ | OH |
| ε-amanitin | H | OH | OH | OH |
| amanin | OH | OH | OH | H |
| amaninamide | OH | OH | $NH_2$ | H |
| amanullin | H | H | $NH_2$ | OH |
| amanullinic acid | H | H | OH | OH |
| γ-amanin | H | OH | OH | H |
| γ-amaninamide | H | OH | $NH_2$ | H |

SEQUENCE LISTING

```
<160> NUMBER OF SEQ ID NOS: 16

<210> SEQ ID NO 1
<211> LENGTH: 5
<212> TYPE: PRT
<213> ORGANISM: Artificial Sequence
<220> FEATURE:
<223> OTHER INFORMATION: CDRH1 of chHH1-HDP

<400> SEQUENCE: 1

Asp Tyr Asn Met Tyr
```

```
<210> SEQ ID NO 2
<211> LENGTH: 17
<212> TYPE: PRT
<213> ORGANISM: Artificial Sequence
<220> FEATURE:
<223> OTHER INFORMATION: CDRH2 of chHH1-HDP

<400> SEQUENCE: 2

Tyr Ile Asp Pro Tyr Asn Gly Asp Thr Thr Tyr Asn Gln Lys Phe Lys
1               5                   10                  15

Gly

<210> SEQ ID NO 3
<211> LENGTH: 10
<212> TYPE: PRT
<213> ORGANISM: Artificial Sequence
<220> FEATURE:
<223> OTHER INFORMATION: CDRH3 of chHH1-HDP

<400> SEQUENCE: 3

Ser Pro Tyr Gly His Tyr Ala Met Asp Tyr
1               5                   10

<210> SEQ ID NO 4
<211> LENGTH: 11
<212> TYPE: PRT
<213> ORGANISM: Artificial Sequence
<220> FEATURE:
<223> OTHER INFORMATION: CDRL1 of chHH1-HDP

<400> SEQUENCE: 4

Lys Ala Ser Gln Asp Val Ser Thr Ala Val Asp
1               5                   10

<210> SEQ ID NO 5
<211> LENGTH: 7
<212> TYPE: PRT
<213> ORGANISM: Artificial Sequence
<220> FEATURE:
<223> OTHER INFORMATION: CDRL2 of chHH1-HDP

<400> SEQUENCE: 5

Trp Ala Ser Thr Arg His Thr
1               5

<210> SEQ ID NO 6
<211> LENGTH: 9
<212> TYPE: PRT
<213> ORGANISM: Artificial Sequence
<220> FEATURE:
<223> OTHER INFORMATION: CDRL3 of chHH1-HDP

<400> SEQUENCE: 6

Arg Gln His Tyr Ser Thr Pro Phe Thr
1               5

<210> SEQ ID NO 7
<211> LENGTH: 119
<212> TYPE: PRT
<213> ORGANISM: Artificial Sequence
<220> FEATURE:
<223> OTHER INFORMATION: Heavy chain variable region of chHH1-HDP

<400> SEQUENCE: 7
```

Glu Ile Gln Leu Gln Gln Ser Gly Pro Glu Leu Val Lys Pro Gly Ala
1               5                   10                  15

Ser Val Lys Val Ser Cys Lys Ala Ser Gly Tyr Ser Phe Thr Asp Tyr
            20                  25                  30

Asn Met Tyr Trp Val Lys Gln Ser His Gly Lys Ser Leu Glu Trp Ile
        35                  40                  45

Gly Tyr Ile Asp Pro Tyr Asn Gly Asp Thr Thr Tyr Asn Gln Lys Phe
    50                  55                  60

Lys Gly Lys Ala Thr Leu Thr Val Asp Lys Ser Ser Thr Ala Phe
65                  70                  75                  80

Ile His Leu Asn Ser Leu Thr Ser Glu Asp Ser Ala Val Tyr Tyr Cys
                85                  90                  95

Ala Arg Ser Pro Tyr Gly His Tyr Ala Met Asp Tyr Trp Gly Gln Gly
                100                 105                 110

Thr Ser Val Thr Val Ser Ser
            115

<210> SEQ ID NO 8
<211> LENGTH: 108
<212> TYPE: PRT
<213> ORGANISM: Artificial Sequence
<220> FEATURE:
<223> OTHER INFORMATION: Light chain variable region of chHH1-HDP

<400> SEQUENCE: 8

Asp Ile Val Met Thr Gln Ser His Lys Leu Leu Ser Thr Ser Val Gly
1               5                   10                  15

Asp Arg Val Ser Ile Thr Cys Lys Ala Ser Gln Asp Val Ser Thr Ala
            20                  25                  30

Val Asp Trp Tyr Gln Gln Lys Pro Gly Gln Ser Pro Lys Leu Leu Ile
        35                  40                  45

Asn Trp Ala Ser Thr Arg His Thr Gly Val Pro Asp Arg Phe Thr Gly
    50                  55                  60

Ser Gly Ser Gly Thr Asp Tyr Thr Leu Thr Ile Ser Ser Met Gln Ala
65                  70                  75                  80

Glu Asp Leu Ala Leu Tyr Tyr Cys Arg Gln His Tyr Ser Thr Pro Phe
                85                  90                  95

Thr Phe Gly Ser Gly Thr Lys Leu Glu Ile Lys Arg
                100                 105

<210> SEQ ID NO 9
<211> LENGTH: 449
<212> TYPE: PRT
<213> ORGANISM: Artificial Sequence
<220> FEATURE:
<223> OTHER INFORMATION: Heavy chain of chHH1-HDP

<400> SEQUENCE: 9

Glu Ile Gln Leu Gln Gln Ser Gly Pro Glu Leu Val Lys Pro Gly Ala
1               5                   10                  15

Ser Val Lys Val Ser Cys Lys Ala Ser Gly Tyr Ser Phe Thr Asp Tyr
            20                  25                  30

Asn Met Tyr Trp Val Lys Gln Ser His Gly Lys Ser Leu Glu Trp Ile
        35                  40                  45

Gly Tyr Ile Asp Pro Tyr Asn Gly Asp Thr Thr Tyr Asn Gln Lys Phe
    50                  55                  60

Lys Gly Lys Ala Thr Leu Thr Val Asp Lys Ser Ser Thr Ala Phe
65                  70                  75                  80

```
Ile His Leu Asn Ser Leu Thr Ser Glu Asp Ser Ala Val Tyr Tyr Cys
                 85                  90                  95

Ala Arg Ser Pro Tyr Gly His Tyr Ala Met Asp Tyr Trp Gly Gln Gly
            100                 105                 110

Thr Ser Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 10
<211> LENGTH: 449
<212> TYPE: PRT
<213> ORGANISM: Artificial Sequence
<220> FEATURE:
<223> OTHER INFORMATION: Heavy chain of chHH1-HDP-D265C comprising amino
``` acid substitution D265C

<400> SEQUENCE: 10

```
Glu Ile Gln Leu Gln Gln Ser Gly Pro Glu Leu Val Lys Pro Gly Ala
1               5                   10                  15
Ser Val Lys Val Ser Cys Lys Ala Ser Gly Tyr Ser Phe Thr Asp Tyr
            20                  25                  30
Asn Met Tyr Trp Val Lys Gln Ser His Gly Lys Ser Leu Glu Trp Ile
        35                  40                  45
Gly Tyr Ile Asp Pro Tyr Asn Gly Asp Thr Thr Tyr Asn Gln Lys Phe
    50                  55                  60
Lys Gly Lys Ala Thr Leu Thr Val Asp Lys Ser Ser Thr Ala Phe
65                  70                  75                  80
Ile His Leu Asn Ser Leu Thr Ser Glu Asp Ser Ala Val Tyr Tyr Cys
                85                  90                  95
Ala Arg Ser Pro Tyr Gly His Tyr Ala Met Asp Tyr Trp Gly Gln Gly
            100                 105                 110
Thr Ser Val Thr Val Ser Ser Ala Ser Thr Lys Gly Pro Ser Val Phe
        115                 120                 125
Pro Leu Ala Pro Ser Ser Lys Ser Thr Ser Gly Gly Thr Ala Ala Leu
    130                 135                 140
Gly Cys Leu Val Lys Asp Tyr Phe Pro Glu Pro Val Thr Val Ser Trp
145                 150                 155                 160
Asn Ser Gly Ala Leu Thr Ser Gly Val His Thr Phe Pro Ala Val Leu
                165                 170                 175
Gln Ser Ser Gly Leu Tyr Ser Leu Ser Ser Val Val Thr Val Pro Ser
            180                 185                 190
Ser Ser Leu Gly Thr Gln Thr Tyr Ile Cys Asn Val Asn His Lys Pro
        195                 200                 205
Ser Asn Thr Lys Val Asp Lys Lys Val Glu Pro Lys Ser Cys Asp Lys
    210                 215                 220
Thr His Thr Cys Pro Pro Cys Pro Ala Pro Glu Leu Leu Gly Gly Pro
225                 230                 235                 240
Ser Val Phe Leu Phe Pro Pro Lys Pro Lys Asp Thr Leu Met Ile Ser
                245                 250                 255
Arg Thr Pro Glu Val Thr Cys Val Val Val Cys Val Ser His Glu Asp
            260                 265                 270
Pro Glu Val Lys Phe Asn Trp Tyr Val Asp Gly Val Glu Val His Asn
        275                 280                 285
Ala Lys Thr Lys Pro Arg Glu Glu Gln Tyr Asn Ser Thr Tyr Arg Val
    290                 295                 300
Val Ser Val Leu Thr Val Leu His Gln Asp Trp Leu Asn Gly Lys Glu
305                 310                 315                 320
Tyr Lys Cys Lys Val Ser Asn Lys Ala Leu Pro Ala Pro Ile Glu Lys
                325                 330                 335
Thr Ile Ser Lys Ala Lys Gly Gln Pro Arg Glu Pro Gln Val Tyr Thr
            340                 345                 350
Leu Pro Pro Ser Arg Glu Glu Met Thr Lys Asn Gln Val Ser Leu Thr
        355                 360                 365
Cys Leu Val Lys Gly Phe Tyr Pro Ser Asp Ile Ala Val Glu Trp Glu
    370                 375                 380
Ser Asn Gly Gln Pro Glu Asn Asn Tyr Lys Thr Thr Pro Pro Val Leu
385                 390                 395                 400
```

```
Asp Ser Asp Gly Ser Phe Phe Leu Tyr Ser Lys Leu Thr Val Asp Lys
            405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

Lys

<210> SEQ ID NO 11
<211> LENGTH: 449
<212> TYPE: PRT
<213> ORGANISM: Artificial Sequence
<220> FEATURE:
<223> OTHER INFORMATION: Heavy chain of chHH1-HDP-LALA-D265C comprising
      amino acid substitutions L235A, L235A and D265C

<400> SEQUENCE: 11

Glu Ile Gln Leu Gln Gln Ser Gly Pro Glu Leu Val Lys Pro Gly Ala
1               5                   10                  15

Ser Val Lys Val Ser Cys Lys Ala Ser Gly Tyr Ser Phe Thr Asp Tyr
            20                  25                  30

Asn Met Tyr Trp Val Lys Gln Ser His Gly Lys Ser Leu Glu Trp Ile
        35                  40                  45

Gly Tyr Ile Asp Pro Tyr Asn Gly Asp Thr Thr Tyr Asn Gln Lys Phe
50                  55                  60

Lys Gly Lys Ala Thr Leu Thr Val Asp Lys Ser Ser Ser Thr Ala Phe
65                  70                  75                  80

Ile His Leu Asn Ser Leu Thr Ser Glu Asp Ser Ala Val Tyr Tyr Cys
                85                  90                  95

Ala Arg Ser Pro Tyr Gly His Tyr Ala Met Asp Tyr Trp Gly Gln Gly
            100                 105                 110

Thr Ser Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
210                 215                 220

Thr His Thr Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Cys Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
290                 295                 300
```

```
Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 12
<211> LENGTH: 214
<212> TYPE: PRT
<213> ORGANISM: Artificial Sequence
<220> FEATURE:
<223> OTHER INFORMATION: Light chain of chHH1-HDP, chHH1-HDP-265C,
      chHH1-HDP-LALA-D265C, respectively

<400> SEQUENCE: 12

Asp Ile Val Met Thr Gln Ser His Lys Leu Leu Ser Thr Ser Val Gly
1               5                   10                  15

Asp Arg Val Ser Ile Thr Cys Lys Ala Ser Gln Asp Val Ser Thr Ala
            20                  25                  30

Val Asp Trp Tyr Gln Gln Lys Pro Gly Gln Ser Pro Lys Leu Leu Ile
        35                  40                  45

Asn Trp Ala Ser Thr Arg His Thr Gly Val Pro Asp Arg Phe Thr Gly
    50                  55                  60

Ser Gly Ser Gly Thr Asp Tyr Thr Leu Thr Ile Ser Ser Met Gln Ala
65                  70                  75                  80

Glu Asp Leu Ala Leu Tyr Tyr Cys Arg Gln His Tyr Ser Thr Pro Phe
                85                  90                  95

Thr Phe Gly Ser Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205
```

Phe Asn Arg Gly Glu Cys
    210

<210> SEQ ID NO 13
<211> LENGTH: 281
<212> TYPE: PRT
<213> ORGANISM: Homo sapiens

<400> SEQUENCE: 13

Met Ser Ala Gln Glu Ser Cys Leu Ser Leu Ile Lys Tyr Phe Leu Phe
1               5                   10                  15

Val Phe Asn Leu Phe Phe Phe Val Leu Gly Ser Leu Ile Phe Cys Phe
            20                  25                  30

Gly Ile Trp Ile Leu Ile Asp Lys Thr Ser Phe Val Ser Phe Val Gly
        35                  40                  45

Leu Ala Phe Val Pro Leu Gln Ile Trp Ser Lys Val Leu Ala Ile Ser
    50                  55                  60

Gly Ile Phe Thr Met Gly Ile Ala Leu Leu Gly Cys Val Gly Ala Leu
65                  70                  75                  80

Lys Glu Leu Arg Cys Leu Leu Gly Leu Tyr Phe Gly Met Leu Leu Leu
                85                  90                  95

Leu Phe Ala Thr Gln Ile Thr Leu Gly Ile Leu Ile Ser Thr Gln Arg
            100                 105                 110

Ala Gln Leu Glu Arg Ser Leu Arg Asp Val Val Glu Lys Thr Ile Gln
        115                 120                 125

Lys Tyr Gly Thr Asn Pro Glu Glu Thr Ala Ala Glu Glu Ser Trp Asp
    130                 135                 140

Tyr Val Gln Phe Gln Leu Arg Cys Cys Gly Trp His Tyr Pro Gln Asp
145                 150                 155                 160

Trp Phe Gln Val Leu Ile Leu Arg Gly Asn Gly Ser Glu Ala His Arg
                165                 170                 175

Val Pro Cys Ser Cys Tyr Asn Leu Ser Ala Thr Asn Asp Ser Thr Ile
            180                 185                 190

Leu Asp Lys Val Ile Leu Pro Gln Leu Ser Arg Leu Gly His Leu Ala
        195                 200                 205

Arg Ser Arg His Ser Ala Asp Ile Cys Ala Val Pro Ala Glu Ser His
    210                 215                 220

Ile Tyr Arg Glu Gly Cys Ala Gln Gly Leu Gln Lys Trp Leu His Asn
225                 230                 235                 240

Asn Leu Ile Ser Ile Val Gly Ile Cys Leu Gly Val Gly Leu Leu Glu
                245                 250                 255

Leu Gly Phe Met Thr Leu Ser Ile Phe Leu Cys Arg Asn Leu Asp His
            260                 265                 270

Val Tyr Asn Arg Leu Ala Arg Tyr Arg
        275                 280

<210> SEQ ID NO 14
<211> LENGTH: 1347
<212> TYPE: DNA
<213> ORGANISM: Artificial Sequence
<220> FEATURE:
<223> OTHER INFORMATION: Heavy chain of chHH1-HDP-LALA-265C, DNA
      sequence

<400> SEQUENCE: 14
gagatccagc tgcagcagtc tggacctgag ctggtgaagc ctggggcttc agtgaaggta      60
tcctgcaagg cttctggtta ctcattcact gactacaaca tgtactgggt gaagcagagc     120

```
catggaaaga gccttgagtg gattggatat attgatcctt acaatggtga tactacctac      180
aaccagaagt tcaagggcaa ggccacattg actgttgaca agtcctccag cacagccttc      240
atccatctca acagcctgac atctgaggac tctgcagtct attactgtgc aagatcccct      300
tatggtcact atgctatgga ctactggggt caaggaacct cagtcaccgt ctcctcagct      360
agcaccaagg gcccatcggt cttccccctg gcacctcct ccaagagcac ctctgggggc      420
acagcggccc tgggctgcct ggtcaaggac tacttcccg aaccggtgac ggtgtcgtgg        480
aactcaggcg ccctgaccag cggcgtgcac accttcccgg ctgtcctaca gtcctcagga      540
ctctactccc tcagcagcgt ggtgaccgtg ccctccagca gcttgggcac ccagacctac      600
atctgcaacg tgaatcacaa gcccagcaac accaaggtgg acaagaaagt tgagcccaaa      660
tcttgtgaca aaactcacac atgcccaccg tgcccagcac ctgaagccgc ggggggaccg      720
tcagtcttcc tcttccccc aaaacccaag gacaccctca tgatctcccg gacccctgag       780
gtcacatgcg tggtggtgtg cgtgagccac gaagaccctg aggtcaagtt caactggtac      840
gtggacggcg tggaggtgca taatgccaag acaaagccgc gggaggagca gtacaacagc      900
acgtaccgtg tggtcagcgt cctcaccgtc ctgcaccagg actggctgaa tggcaaggag      960
tacaagtgca aggtctccaa caaagccctc ccagccccca tcgagaaaac catctccaaa     1020
gccaaagggc agccccgaga accacaggt a tacaccctgc ccccatcccg ggaggagatg     1080
accaagaacc aggtcagcct gacctgcctg gtcaaaggct tctatcccag cgacatcgcc     1140
gtggagtggg agagcaatgg gcagccggag aacaactaca agaccacgcc tcccgtgctg     1200
gactccgacg gctccttctt cctctacagc aagctcaccg tggacaagag caggtggcag     1260
caggggaacg tcttctcatg ctccgtgatg catgaggctc tgcacaacca ctacacgcag     1320
aagagcctct ccctgtctcc gggtaaa                                          1347

<210> SEQ ID NO 15
<211> LENGTH: 642
<212> TYPE: DNA
<213> ORGANISM: Artificial Sequence
<220> FEATURE:
<223> OTHER INFORMATION: Light chain of chHH1-HDP, chHH1-HDP-265C,
      chHH1-HDP-LALA-265C, DNA sequence

<400> SEQUENCE: 15
gacattgtga tgacccagtc tcacaaactc ttgtccacat cagtaggaga cagggtcagc       60
atcacctgca aggccagtca ggatgtgagt actgctgtag actggtatca acagaaacca      120
ggacaatctc ctaaactact gattaactgg gcatccaccc ggcacactgg agtccctgat      180
cgcttcacag gcagtggatc tgggacagat tatactctca ccatcagcag tatgcaggct      240
gaagacctgg cactttatta ctgtcgacaa cattatagca ctccattcac gttcggctcg      300
gggacaaagt tggaaataaa acgaacggtg gctgcaccat ctgtcttcat cttcccgcca      360
tctgatgagc agttgaaatc cggaactgcc tctgttgtgt gcctgctgaa taacttctat      420
cccagagagg ccaaagtaca gtggaaggtg gataacgccc tccaatcggg taactcccag      480
gagagtgtca cagagcagga cagcaaggac agcacctaca gcctcagcag caccctgacg      540
ctgagcaaag cagactacga gaaacacaaa gtctacgcct gcgaagtcac ccatcagggc      600
ctgagctcgc ccgtcacaaa gagcttcaac aggggagagt gt                         642

<210> SEQ ID NO 16
<211> LENGTH: 345
```

```
<212> TYPE: PRT
<213> ORGANISM: Macaca fascicularis
<220> FEATURE:
<223> OTHER INFORMATION: Cynomolgus CD37

<400> SEQUENCE: 16
```

| | | | | | | | | | | | | | | |
|---|---|---|---|---|---|---|---|---|---|---|---|---|---|---|
| Met | Ser | Ala | Gln | Glu | Ser | Cys | Leu | Ser | Leu | Ile | Lys | Tyr | Phe | Leu | Phe |
| 1 | | | | 5 | | | | | 10 | | | | | 15 | |
| Val | Phe | Asn | Leu | Phe | Phe | Val | Leu | Gly | Ser | Leu | Ile | Phe | Cys | Phe |
| | | | 20 | | | | | 25 | | | | | 30 | |
| Gly | Ile | Trp | Ile | Leu | Ile | Asp | Lys | Thr | Ser | Phe | Val | Ser | Phe | Val | Gly |
| | | | 35 | | | | | 40 | | | | | 45 | | |
| Leu | Ala | Phe | Val | Pro | Leu | Gln | Ile | Trp | Ser | Lys | Val | Leu | Ala | Ile | Ser |
| | 50 | | | | | 55 | | | | | 60 | | | | |
| Gly | Val | Phe | Thr | Met | Gly | Leu | Ala | Leu | Leu | Gly | Cys | Val | Gly | Ala | Leu |
| 65 | | | | | 70 | | | | | 75 | | | | | 80 |
| Lys | Glu | Leu | Arg | Cys | Leu | Leu | Gly | Leu | Tyr | Phe | Gly | Met | Leu | Leu | Leu |
| | | | | 85 | | | | | 90 | | | | | 95 | |
| Leu | Phe | Ala | Thr | Gln | Ile | Thr | Leu | Gly | Ile | Leu | Ile | Ser | Thr | Gln | Arg |
| | | | 100 | | | | | 105 | | | | | 110 | | |
| Ala | Gln | Leu | Glu | Arg | Ser | Leu | Gln | Asp | Ile | Val | Glu | Lys | Thr | Ile | Gln |
| | | | 115 | | | | | 120 | | | | | 125 | | |
| Lys | Tyr | His | Thr | Asn | Pro | Glu | Glu | Thr | Ala | Ala | Glu | Glu | Ser | Trp | Asp |
| | | | 130 | | | | | 135 | | | | | 140 | | |
| Tyr | Val | Gln | Phe | Gln | Val | Ser | Pro | Leu | Leu | Gln | Leu | Pro | Pro | Arg | Leu |
| 145 | | | | | 150 | | | | | 155 | | | | | 160 |
| Thr | Arg | Leu | Ser | Pro | Val | Leu | Arg | Gly | Asp | Ser | Thr | Pro | Thr | Trp | Pro |
| | | | | 165 | | | | | 170 | | | | | 175 | |
| Arg | Pro | Pro | Ala | Leu | His | Asp | Leu | Thr | His | Ser | Gln | Pro | Leu | Pro | Gly |
| | | | 180 | | | | | 185 | | | | | 190 | | |
| Pro | Thr | Pro | Ala | Thr | Pro | Gln | Met | Thr | Gln | Leu | Ala | Pro | Ala | Trp | Pro |
| | | | 195 | | | | | 200 | | | | | 205 | | |
| Ser | Leu | Pro | Val | Pro | Arg | Pro | Trp | His | Gly | Phe | Ala | Ile | Tyr | Leu | Gly |
| | | | 210 | | | | | 215 | | | | | 220 | | |
| Arg | Leu | Arg | Pro | Arg | Pro | Asp | Pro | Ala | Pro | Thr | Gly | Gly | Ser | Gln | Ala |
| 225 | | | | | 230 | | | | | 235 | | | | | 240 |
| Pro | Ser | Pro | Lys | Thr | Leu | Ala | Arg | His | Gly | Phe | Leu | Pro | Arg | Ser | Glu |
| | | | | 245 | | | | | 250 | | | | | 255 | |
| Ser | Gly | Phe | His | Arg | Thr | Pro | Pro | Arg | Met | Arg | Leu | Thr | Gly | Ser | Arg |
| | | | 260 | | | | | 265 | | | | | 270 | | |
| Thr | Pro | Ile | His | Leu | Ser | Gly | Ile | Arg | Gly | Ser | Ile | Ala | Pro | Pro | Thr |
| | | | 275 | | | | | 280 | | | | | 285 | | |
| Asn | Leu | Trp | Phe | Arg | Ala | Arg | Arg | Cys | Ser | Tyr | Phe | Pro | Ser | Pro | Arg |
| | | | 290 | | | | | 295 | | | | | 300 | | |
| Ser | Pro | Arg | Asp | Pro | Ser | Leu | Pro | Ala | Pro | Phe | Pro | Val | Met | Ser | Pro |
| 305 | | | | | 310 | | | | | 315 | | | | | 320 |
| Gly | Pro | Gly | Pro | Ile | Ala | Thr | Pro | Ala | His | Trp | Pro | Pro | Leu | His | Thr |
| | | | | 325 | | | | | 330 | | | | | 335 | |
| His | His | Leu | Val | Pro | Cys | Phe | Pro | Thr |
| | | | | 340 | | | | | 345 |

B-LYMPHOCYTE SPECIFIC AMATOXIN ANTIBODY CONJUGATES

CROSS-REFERENCE TO RELATED APPLICATIONS

This patent application claims the benefit of European Patent Application No. 21163784.8, filed Mar. 19, 2021, which is incorporated by reference in its entirety herein.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: one 26,021 Byte ASCII (Text) file named "SequenceListing_HD-41529.txt," created Mar. 9, 2022.

FIELD OF THE INVENTION

The present application relates to conjugates comprising an amatoxin a target-binding moiety wherein the target is CD37, i.e., a CD37-binding moiety, and optionally a linker linking said amatoxin and said CD37-binding moiety. The invention further relates to the synthesis of said conjugates. In addition, the invention relates to a pharmaceutical composition comprising such conjugate for use in the treatment of immune cell-, particularly B-cell and/or lymphoma associated diseases and/or malignancies.

BACKGROUND

The leukocyte cell surface protein CD37 is a member of the "tetraspanin" superfamily or transmembrane 4 superfamily, which is characterized by the presence of four conserved transmembrane domains. Tetraspanin family members are membrane proteins that are considered as "molecular facilitators" of signaling transduction, involved in a wide range of biological processes including cell growth, survival, adhesion, cell-cell communication, and trafficking, intercellular communication via exosomes, tumorigenesis, metastasis, and regulation of immune responses. Tetraspanin members have also been described to have functional roles in a wide array of cellular processes, including cell motility, development and differentiation, activation, proliferation, migration and tumor invasion (Hemler 2001; Xu-Monette et al. 2016).

Tetraspanin protein family members contain intracellular N- and C-termini, two extracellular domains (EC1 and EC2), and specifically four transmembrane domains (FIG. 2). The structural composition of tetraspanins is highly conserved among species, with four or more cysteine residues in a highly conserved "CCG" motif in the EC2 domain. At least 33 tetraspanins have been identified in humans (Zou et al. 2018).

Tetraspanins organize specialized membrane platforms, called "tetraspanin-enriched microdomains" (TEM) or "tetraspanins web", which integrate membrane receptors, like pattern recognition receptors (PRR) and major histocompatibility complex class II (MHC-II), adhesion proteins, and signaling molecules. Importantly, through the modulation of the function of their associated membrane partners, tetraspanins regulate different steps of the immune response. Several tetraspanins can positively or negatively regulate the activation threshold of immune receptors. They also play a role during migration of APCs by controlling the surface levels and spatial arrangement of adhesion molecules and their subsequent intracellular signaling. Finally, tetraspanins participate in antigen processing and are important for priming of naïve T cells through the control of T-cell co-stimulation and MHC-II-dependent antigen presentation (Saiz M L et al. 2018; Zou et al. 2018).

Expression of CD37 (tetraspanin TSPAN26) is restricted to cells of the immune system, with highest abundance on normal and in particular on malignant mature B cells, and downregulated in plasma cells (Hemler 2001). CD37 is highly expressed on B cells during the pre-B to peripheral mature B-cell stages, but is absent on early progenitor cells or terminally differentiated plasma cells (Schwartz-Albiez et al. 1988). Lower expression has been found on T cells and myeloid cells.

B cells can promote an immune response through presentation of antigens and production of diverse antibodies, proinflammatory cytokines, and co-stimulators. B cells can also suppress immune responses through a variety of mechanisms, such as production of IL-10, IL-35, and TGFβ1, induction of regulatory T cells, and clearance of auto antigens. Many cell surface molecules are involved in B cell development and function. Tetraspanins are one such important family of molecules (Zou et al. 2018).

CD37 is a cell surface glycoprotein that is known to complex with other transmembrane 4 superfamily proteins, major histocompatibility complex (WIC) class II molecules on B cells, and integrins; MHC-II is expressed on professional antigen-presenting cells (APCs) and associates with several tetraspanins, including CD9, CD37, CD53, CD81, and CD82, at the surface of APCs. CD37 negatively regulates MHC-II clustering, and negatively regulates WIC-dependent antigen presentation to $CD4^+$ and $CD8^+$ T cells (Saiz et al. 2018). CD37 has been shown to stabilize membrane C-type lectin receptor Dectin-1 surface expression and impair its internalization, and to inhibit Dectin-1-mediated TNF-α and IL-6 production. Other proteins that have been described to bind to CD37 include ACPA, PURL, YBTO, PG8786 084, CD19, CD53, SYK, KARS, PTPN6, LYN, PIK3CD, PIK3CG, CD81, and CR2 (Zou et al. 2018).

Alternate splicing results in multiple transcript variants encoding different isoforms of CD37. CD37 is involved in the regulation and control of both humoral and cellular immune responses.

CD37 is important for T-cell-B-cell interaction, immunoglobulin G (IgG)/IgA production, and a balance between immune responses and tolerance. Disruption of CD37 in mice yielded a relatively subtle alteration in B cell IgG production, and a T cell-dependent immune response deficiency that was especially obvious under suboptimal stimulation conditions. Thus, CD37 was concluded to regulate B cell humoral responses as well as T cell-B cell interactions (Knobeloch et al. 2000). CD37-deficiency in mice can lead to spontaneous development on B cell lymphoma. As observed with a Cd37−/− mouse model and patients with diffuse large B-cell lymphoma (DLBCL), loss of CD37 and interaction between CD37 and suppressor of cytokine signaling 3 (SOCS3) leads to constitutive activation of the interleukin 6 (IL6)-AKT-STAT3 pathway, spontaneous development of germinal center-derived lymphoma, and poorer clinical outcomes (Xu-Monette et al. 2016).

In B cells, CD37 has profound roles in proliferation and survival. CD37 regulates the plasma membrane distribution of α(4)β(1) integrins by controlling their mobility and clustering, a necessary step in activating Akt survival pathways. It is reported that the number of IgG-secreting plasma cells is reduced in lymphoid organs when CD37 is knocked out in mice, possibly due to the impaired association of VCAM-1 to the α(4)β(1) integrin for the Akt survival pathway leading to increased apoptosis of plasma cells in germinal centers. In a recent study, CD37 knockout in mice could drive B cell lymphoma progression through constitutive activation of the IL6 pathway by losing the control of suppressor of cytokine signaling 3. Although CD37 is crucial for B cells to survive and provide long lasting immune protection, it has also been found that CD37 may trigger a cascade of events resulting in apoptosis when it is tyrosine phosphorylated and binds with signaling factors. The study also found that CD37 mediates SHP1-dependent death via its N-terminal domain, whereas it antagonizes death signals through the C-terminal domain by mediating PI3K-dependent survival (Zou et al. 2018).

In addition to its role in B cell proliferation and survival, CD37 promotes IgG1 production while inhibiting IgA immune responses in vivo. CD37 deficiency causes a reduction of serum IgG1 levels and alters B cell responses to T cell-dependent antigen under suboptimal costimulatory conditions.

In T cells, Tetraspanins are implicated in T-cell receptor (TCR)-induced activation and proliferation. Interaction of peptide with the MHC activates the TCR and initiates the downstream signaling cascade of Src kinases Fyn and Lck. Lck subsequently activates the functional proteins involved in T cell activation and proliferation. Interaction of Lck with CD4/CD8 plays crucial roles in this pathway; should CD4 associate with tetraspanins CD81/82, then Lck is sequestered from the TCR signaling pathway. A regulatory role for CD37 in T cell proliferation by influencing early events of TCR signaling has been observed by Van Spriel et al. (2004). CD37 has been found to interfere with phosphorylation of Lck kinase, thus inhibiting TCR signaling. CD37 is coupled to TCR signal transduction mostly by influencing the dynamics of CD4-Lck distribution to TCR signal associated microdomains. Thus, tetraspanins regulate the T cell biologic process by influencing the TCR-CD4/CD8 cascade proximal to Lck mobilization (Zou et al. 2018).

Increased CD37 expression was found in B cell malignancies (Zou et al. 2018). Most B-cell malignancies express CD37, including B-cell non-Hodgkin lymphoma (NHL) and B-cell chronic lymphocytic leukemia (B-CLL). CD37 was detected at variable levels in 60% of Burkitt lymphoma cell lines. Although CD37 expression in neoplastic B cells correlated with the maturation stage of their corresponding B-cell counterparts, B-CLL has lower CD37 levels than do normal mature circulating B lymphocytes (Xu-Monette et al. 2016). Belov et al. (2001) reported that utilizing antibody micro-array for immunophenotyping shows CD37 to be a good discriminator between malignant CLL cells (high CD37 expression) versus normal peripheral blood lymphocytes (low CD37 expression).

CD37 was first described and characterized by the murine monoclonal antibody MB-1 in 1986 (Link et al., 1986), which also has been used for radiotherapy.

CD37 could be targeted by monoclonal antibodies (e.g. otlertuzumab) in patients with CLL and NHL expressing high levels of CD37. Upon cross-ligation with anti-CD37 antibodies, CD37 transduces both death signals (from the N-terminal domain associated with Src homology region 2 domain-containing phosphatase-1 (SHP1), LYN, and phosphatidylinositol 3-kinase γ (PI3Kγ) and opposing survival signals (from the C-terminal domain recruiting p85 and PI3Kδ) (Lapalombella et al. 2012; Xu-Monette et al. 2016).

A limited number of CD37-directed antibody therapeutic candidates have been evaluated in patients so far. Such agents might exert anti-tumoral cytotoxic effects through multiple mechanisms including apoptosis induction, antibody-dependent cellular cytotoxicity, antibody-dependent cellular phagocytosis, and complement-dependent cytotoxicity. A recent clinical study by Stilgenbauer et al. (2019) using the antibody BI 836826 in CLL patients confirmed that CD37 represents a promising therapeutic target. CD37-binding small modular immunopharmaceutical proteins have also been advanced into clinical testing as a treatment of B-cell malignancies (Zhao et al. 2007).

Antibody-drug conjugates (ADCs) have been developed that covalently link cytotoxic agents to tumor-targeting antibodies to enhance their antitumor specificity and potency. This approach is designed to allow for specific delivery of cytotoxic compounds to cells expressing the target antigen, through ADC binding, internalization, and intracellular payload release.

An ADC consisting of an anti-CD37 antibody with potent in vitro activity against B-cell lines, conjugated to the maytansinoid DM1, a potent anti-microtubule agent, via the thioether linker, N-succinimidyl-4-(N-maleimidomethyl)cyclohexane-1-carboxylate (SMCC), has been described; said ADC (IMGN529) resulted in potent and specific depletion of normal and CLL B cells (Deckert et al. 2013). In a murine CLL model that develops transplantable hCD37$^+$ leukemia, the ADC IMGN529 eliminated peripheral blood leukemia and improved overall survival; in contrast, the antibody component of IMGN529 alone could not alter the disease course (Beckwith K A et al. 2014).

These data suggest that CD37-directed therapies may be effective. However, there is still a considerable need for agents with improved potency and efficacy profile.

In chronic lymphocytic leukemia (CLL), treatment with the small-molecule Bruton's tyrosine kinase (BTK) inhibitor Ibrutinib has become standard of care. Chronic activation of B-cell receptor (BCR) signaling via Bruton's tyrosine kinase (BTK) is widely considered to be one of the primary mechanisms driving disease progression in B-cell lymphomas. Ibrutinib has demonstrated marked efficacy in CLL in clinical trials, and has been the first BTK inhibitor approved by the US Food and Drug Administration for the therapy of any CLL patient in any line of therapy. Its use has rapidly become standard of care for relapsed CLL patients, as well as for many frontline high-risk or older patients (Brown 2018).

However, although the BTK-targeting agent ibrutinib has shown promising clinical responses, the presence of primary or acquired resistance is common and often leads to dismal clinical outcomes. Resistance to ibrutinib therapy can be mediated through genetic mutations, up-regulation of alternative survival pathways, or other unknown factors that are not targeted by ibrutinib therapy (George B et al. 2020; Fuhrman et al. 2014; Pula B et al. 2019).

Antibody drug conjugates (ADCs) comprising amatoxins and tumor antigen-specific antibodies, antibody fragments or derivatives have been described (WO2010/115629A2, WO2016/142049A1, WO2017/149077A1).

SUMMARY OF THE INVENTION

The inventors surprisingly and unexpectedly found that the amatoxin-based conjugates according to the present invention, in particular comprising CD37-specific antibody, or an antibody fragment or antibody derivative, either with a non-cleavable or cleavable linker linking the anti-CD37 antibody, or antibody fragment or antibody derivative, to the amatoxin were able to overcome ibrutinib resistance and exert significant cytotoxic effects on CD37-positive ibrutinib-resistant target cells in vitro and in vivo.

In view of the prior art, it was hence one object of the present invention to provide conjugates comprising a target binding moiety binding to CD37, at least one amatoxin and optionally at least one linker connecting said target binding moiety with said at least one toxin, that mediate cytotoxic effects in target cells, as described in the present application.

It was one further object of the present invention to provide conjugates comprising a target binding moiety binding to CD37, at least one amatoxin and optionally at least one linker, wherein said target binding moieties are antibodies, or antigen-binding fragments thereof, or antigen-binding derivatives thereof, or antibody-like proteins, that specifically bind to CD37.

It was one further object of the present invention to provide a pharmaceutical composition comprising such conjugates.

It was one further object of the present invention to provide compounds for use in methods for treatment of cancer.

It was one further object of the present invention to provide conjugates comprising a target binding moiety binding to CD37, at least one amatoxin and optionally at least one linker, for use in the treatment of B lymphocyte-associated malignancies or B cell-mediated autoimmune diseases, in particular for use in the treatment of non-Hodgkin's lymphoma, follicular lymphoma, diffuse large B cell non-Hodgkin's lymphoma, chronic lymphocytic leukaemia, Richter syndrome, rheumatoid arthritis, granulomatosis with polyangiitis and microscopic polyangiitis and pemphigus vulgaris.

These and further objects are met with methods and means according to the independent claims of the present invention. The dependent claims are related to specific embodiments.

The invention and general advantages of its features will be discussed in detail below.

FIG. 12. Results of cytotoxic efficacy studies in vivo using various anti-CD37 amatoxin conjugates in a disseminated Raji-Luc tumor xenograft model over 130 days of treatment: Survival.

FIG. 13A. Results of an exploratory toxicity study in Cynomolgus monkeys (*Macaca fascicularis*). Alanine transaminase (ALT) serum levels (mean) using different anti-CD37 antibody-amatoxin conjugates as indicated at escalating doses as indicated for each group.

FIG. 13B. Results of an exploratory toxicity study in Cynomolgus monkeys (*Macaca fascicularis*). Aspartate trans-aminase (AST) serum levels (mean) using different anti-CD37 antibody-amatoxin conjugates as indicated at escalating doses as indicated for each group.

FIG. 13C. Results of an exploratory toxicity study in Cynomolgus monkeys (*Macaca fascicularis*). Lactate dehydrogenase (LDH) serum levels (mean) using different anti-CD37 antibody-amatoxin conjugates as indicated at escalating doses as indicated for each group.

FIG. 13D. Results of an exploratory toxicity study in Cynomolgus monkeys (*Macaca fascicularis*). Alanine transaminase (ALT) serum levels (median) using different anti-CD37 antibody-amatoxin conjugates as indicated at escalating doses as indicated for each group.

FIG. 13E. Results of an exploratory toxicity study in Cynomolgus monkeys (*Macaca fascicularis*). Aspartate trans-aminase (AST) serum levels (median) using different anti-CD37 antibody-amatoxin conjugates as indicated at escalating doses as indicated for each group.

FIG. 13F. Results of an exploratory toxicity study in Cynomolgus monkeys (*Macaca fascicularis*). Lactate dehydrogenase (LDH) serum levels (median) using different anti-CD37 antibody-amatoxin conjugates as indicated at escalating doses as indicated for each group.

FIG. 14A. Results of an exploratory toxicity study in Cynomolgus monkeys (*Macaca fascicularis*). Alanine transaminase (ALT) serum levels using an anti-CD37 antibody-amatoxin conjugate as indicated. Crosses indicate euthanized or animals which have died.

FIG. 14B. Results of an exploratory toxicity study in Cynomolgus monkeys (*Macaca fascicularis*). Alanine transaminase (ALT) serum levels using an anti-CD37 antibody-amatoxin conjugate as indicated. Crosses indicate euthanized or animals which have died.

FIG. 14C. Results of an exploratory toxicity study in Cynomolgus monkeys (*Macaca fascicularis*). Alanine transaminase (ALT) serum levels using an anti-CD37 antibody-amatoxin conjugate as indicated. Crosses indicate euthanized or animals which have died.

FIG. 14D. Results of an exploratory toxicity study in Cynomolgus monkeys (*Macaca fascicularis*). Aspartate transaminase (AST) serum levels using an anti-CD37 antibody-amatoxin conjugate as indicated. Crosses indicate euthanized or animals which have died.

FIG. 14E. Results of an exploratory toxicity study in Cynomolgus monkeys (*Macaca fascicularis*). Aspartate transaminase (AST) serum levels using an anti-CD37 antibody-amatoxin conjugate as indicated. Crosses indicate euthanized or animals which have died.

FIG. 14F. Results of an exploratory toxicity study in Cynomolgus monkeys (*Macaca fascicularis*). Aspartate transaminase (AST) serum levels using an anti-CD37 antibody-amatoxin conjugate as indicated. Crosses indicate euthanized or animals which have died.

FIG. 14G. Results of an exploratory toxicity study in Cynomolgus monkeys (*Macaca fascicularis*). Lactate dehydrogenase (LDH) serum levels using an anti-CD37 antibody-amatoxin conjugate as indicated. Crosses indicate euthanized or animals which have died.

FIG. 1411. Results of an exploratory toxicity study in Cynomolgus monkeys (*Macaca fascicularis*). Lactate dehydrogenase (LDH) serum levels using an anti-CD37 antibody-amatoxin conjugate as indicated. Crosses indicate euthanized or animals which have died.

FIG. 141. Results of an exploratory toxicity study in Cynomolgus monkeys (*Macaca fascicularis*). Lactate dehydrogenase (LDH) serum levels using an anti-CD37 antibody-amatoxin conjugate as indicated. Crosses indicate euthanized or animals which have died.

FIG. 15A. Results of an exploratory toxicity study in Cynomolgus monkeys (*Macaca fascicularis*). Alanine transaminase (ALT) serum levels over more than 200 days using an unspecific antibody-amatoxin conjugate at doses of between 1.0 and 20 mg/kg as indicated.

FIG. 15B. Results of an exploratory toxicity study in Cynomolgus monkeys (*Macaca fascicularis*). Aspartate transaminase (AST) serum levels over more than 200 days using an unspecific antibody-amatoxin conjugate at doses of between 1.0 and 20 mg/kg as indicated.

FIG. 15C. Results of an exploratory toxicity study in Cynomolgus monkeys (*Macaca fascicularis*). Lactate dehydrogenase (LDH) serum levels over more than 200 days using an unspecific antibody-amatoxin conjugate at doses of between 1.0 and 20 mg/kg as indicated.

FIG. 16A. Results of a Richter Syndrome patient-derived xenograft (PDX) model (RS1316) treated with anti-CD37 antibody-amatoxin conjugates of the invention. Survival plot of animals treated with amatoxin conjugates of the invention as indicated up to 75 days post treatment.

FIG. 16B. Results of a Richter Syndrome patient-derived xenograft (PDX) model (RS1316) treated with anti-CD37 antibody-amatoxin conjugates of the invention. Number of residual RS cells (CD45+, CD19+, CD20+ positive cells) in kidney (kid), liver (liv), lung, bone marrow (BM), peripheral blood (PB), brain (bra) and spleen (Spl) following the single treatment with amatoxin conjugates as indicated.

Figure 17A:
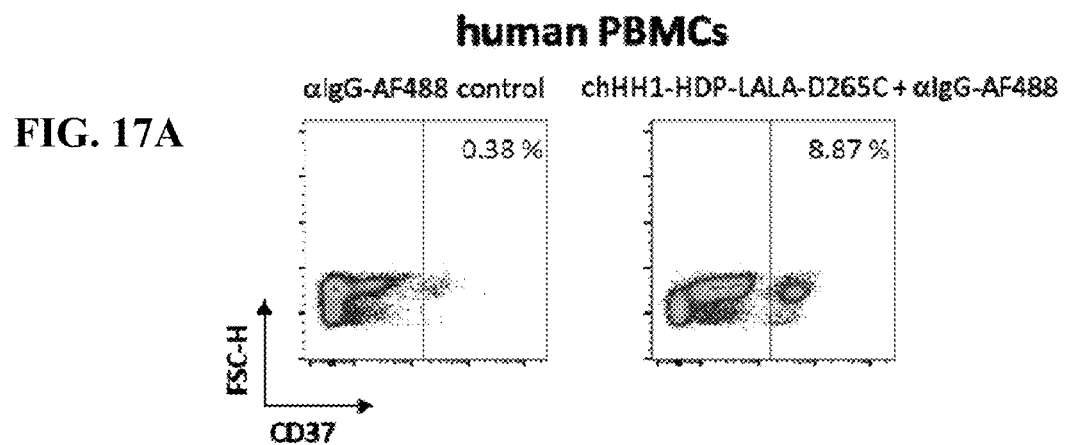

FIG. 17A. Binding of anti-CD37 chHH1-HDP-LALA-D265C antibody to human peripheral blood mononuclear cells (PBMCs) assessed by flow cytometry. Left panel: Control: human PBMCs stained with goat anti-Human IgG (Fc)-AlexaFluor488 Fab only; right panel: human PBMCs stained with anti-CD37 chHH1-HDP-LALA-D265C and Goat anti-Human IgG (Fc)-AlexaFluor488 Fab secondary antibody.

Figure 17B:
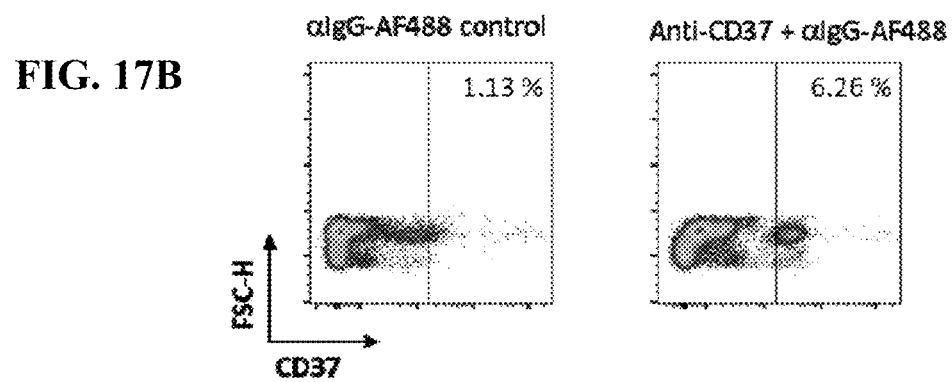

FIG. 17B. Binding of anti-CD37 chHH1-HDP-LALA-D265C antibody to human peripheral blood mononuclear cells (PBMCs) assessed by flow cytometry. Left panel: Control: human PBMCs stained with goat anti-mouse IgG (Fc)-AlexaFluor488 Fab only; right panel: human PBMCs stained with a mouse anti-human CD37 antibody and goat anti-mouse IgG (Fc)-AlexaFluor488 F(ab)2-fragment secondary antibody.

Figure 17C:
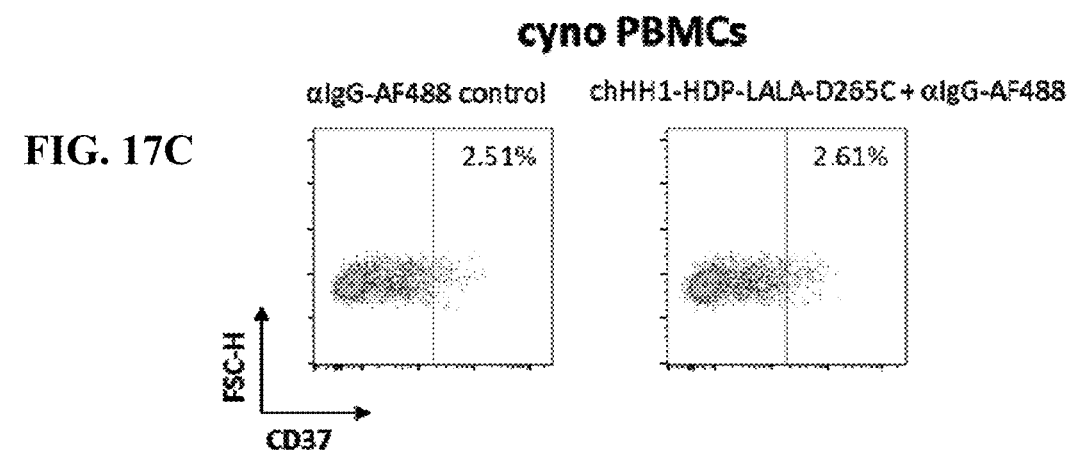

FIG. 17C. Binding of anti-CD37 chHH1-HDP-LALA-D265C antibody to cynomolgus peripheral blood mononuclear cells (PBMCs) assessed by flow cytometry. Left panel: cynomolgus PBMCs stained with goat anti-mouse IgG (Fc)-AlexaFluor488 F(ab)2-fragment only, right panel: cynomolgus PBMCs stained with anti-CD37 chHH1-HDP-LALA-D265C and goat anti-Human IgG (Fc)-AlexaFluor488 Fab secondary antibody.

Figure 17D:
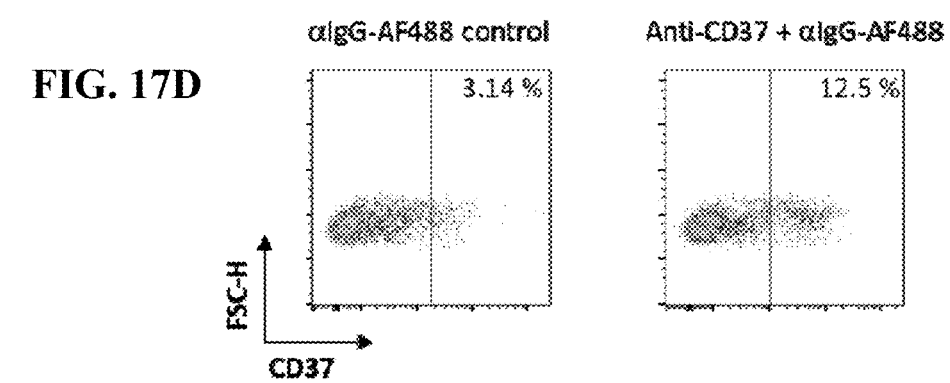

FIG. 17D. Binding of anti-CD37 chHH1-HDP-LALA-D265C antibody to cynomolgus peripheral blood mononuclear cells (PBMCs) assessed by flow cytometry. Left panel: cynomolgus PBMCs stained with goat anti-mouse IgG (Fc)-AlexaFluor488 F(ab)2-fragment only, right panel: cynomolgus PBMCs stained with mouse anti-human CD37 antibody and goat anti-mouse IgG (Fc)-AlexaFluor488 F(ab)2-fragment as secondary antibody.

Figure 18A:
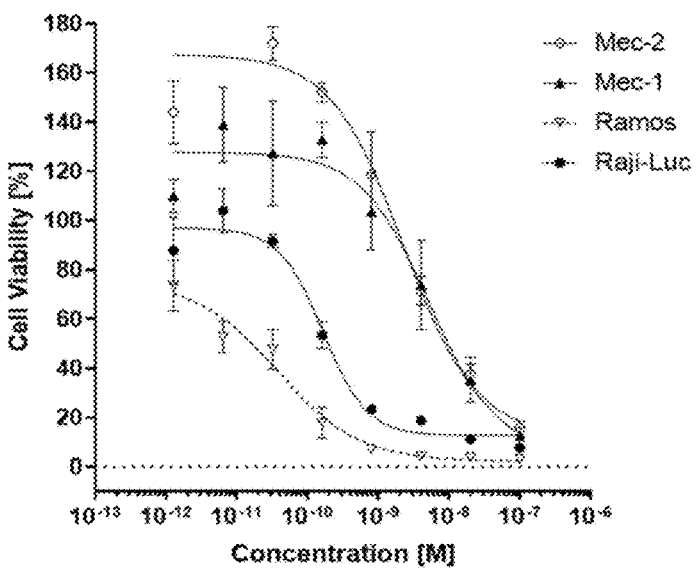

FIG. 18A. Cytotoxicity of Conjugate XXV of the invention. Dependency of cytotoxicity of the conjugate of the invention was assessed on MEC-1, MEC-2, Ramos and Raji-luc cells. The results indicate that irrespective of the number of detectable CD37 epitopes expressed on the cell surface (low expression on Ramos, or MEC-1 cells in comparison to a high expression on MEC-2 cells) the conjugate of the invention has a high cytotoxicity on the target cells as evidenced by effective cell killing. Quantification of CD37 epitopes was done using a Quantum™ MESF Kit according to the manufacturer's instructions.

Figure 18B:
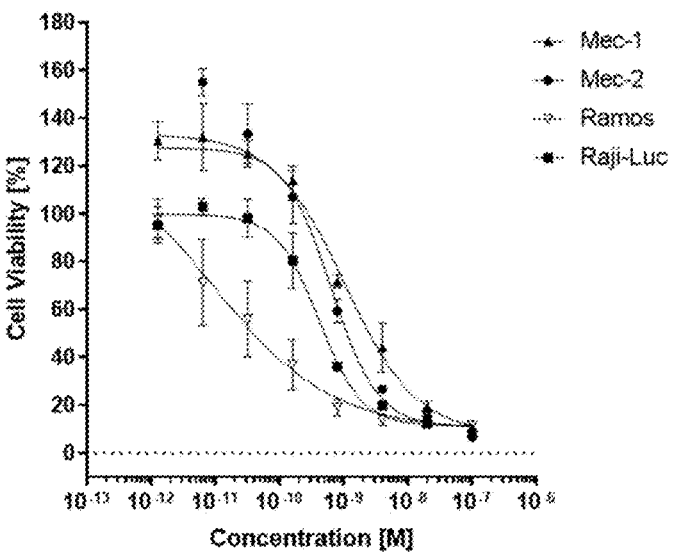

FIG. 18B. Cytotoxicity of Conjugate XIII of the invention. Dependency of cytotoxicity of the conjugate of the invention was assessed on MEC-1, MEC-2, Ramos and Raji-luc cells. The results indicate that irrespective of the number of detectable CD37 epitopes expressed on the cell surface (low expression on Ramos, or MEC-1 cells in comparison to a high expression on MEC-2 cells) the conjugate of the invention has a high cytotoxicity on the target cells as evidenced by effective cell killing. Quantification of CD37 epitopes was done using a Quantum™ MESF Kit according to the manufacturer's instructions.

Figure 19:
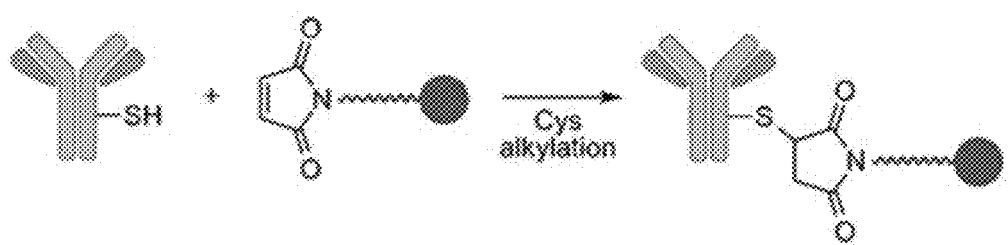

FIG. 19. Synthesis scheme of Anti-CD37 amatoxin conjugates. The conjugation takes place by coupling of the maleimide residue of the toxin linker construct to the free SH group of a cysteine residue in the antibody.

DETAILED DESCRIPTION OF THE INVENTION

Before the invention is described in detail, it is to be understood that this invention is not limited to the particular component parts of the devices described or process steps of the methods described as such devices and methods may vary. It is also to be understood that the terminology used herein is for purposes of describing particular embodiments only and is not intended to be limiting. It must be noted that, as used in the specification and the appended claims, the singular forms "a", "an", and "the" include singular and/or plural referents unless the context clearly dictates otherwise. It is moreover to be understood that, in case parameter ranges are given which are delimited by numeric values, the ranges are deemed to include these limitation values. Recitation of ranges of values herein is merely intended to serve as a shorthand method of referring individually to each separate value falling within the range. Unless otherwise indicated herein, each individual value is incorporated into the specification as if it were individually recited herein.

Throughout this specification and the claims which follow, unless the context requires otherwise, the term "comprise", and variations such as "comprises" and "comprising", will be understood to imply the inclusion of a stated member, integer or step but not the exclusion of any other non-stated member, integer or step. The term "consist of" is a particular embodiment of the term "comprise", wherein any other non-stated member, integer or step is excluded.

It is further to be understood that embodiments disclosed herein are not meant to be understood as individual embodiments which would not relate to one another. Features discussed with one embodiment are meant to be disclosed also in connection with other embodiments shown herein. If, in one case, a specific feature is not disclosed with one embodiment, but with another, the skilled person would understand that does not necessarily mean that said feature is not meant to be disclosed with said other embodiment. The skilled person would understand that it is the gist of this application to disclose said feature also for the other embodiment, but that just for purposes of clarity and to keep the specification in a manageable volume this has not been done.

Furthermore, the content of the prior art documents referred to herein is incorporated by reference. This refers, particularly, for prior art documents that disclose standard or routine methods. In that case, the incorporation by reference has mainly the purpose to provide sufficient enabling disclosure and avoid lengthy repetitions. Chemical terminology used throughout the present application shall be construed according to the "Compendium of Chemical Terminology" published by the International Union of Pure and Applied Chemistry, ISBN: 0-9678550-9-8.

Throughout this application the term "about" is used which shall refer to +/−10% of the numerical value with which it is used.

According to a first aspect of the present invention, the present invention relates to a conjugate comprising (i) a target binding moiety, (ii) at least one toxin, and (iii) optionally at least one linker connecting said target binding moiety with said at least one toxin, wherein said target binding moiety binds to CD37 and wherein said at least one toxin is an amatoxin.

Figure 1:
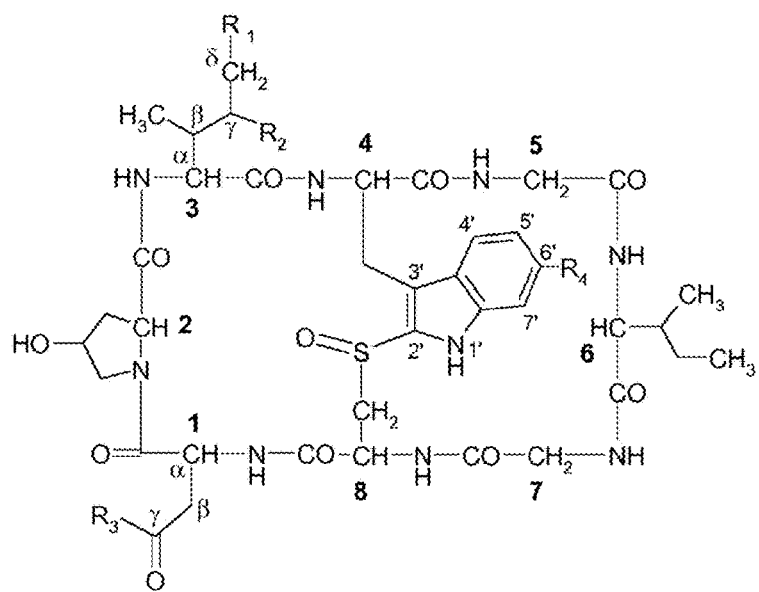
FIG. 1. Markush structure of various amatoxins. The numbers in bold type (1 to 8) designate the standard numbering of the eight amino acids forming the amatoxin. The standard designations of the atoms in amino acids 1, 3, and 4 are also shown (Greek letters α to γ, Greek letters α to δ, and numbers from 1' to 7', respectively).
Figure 2:
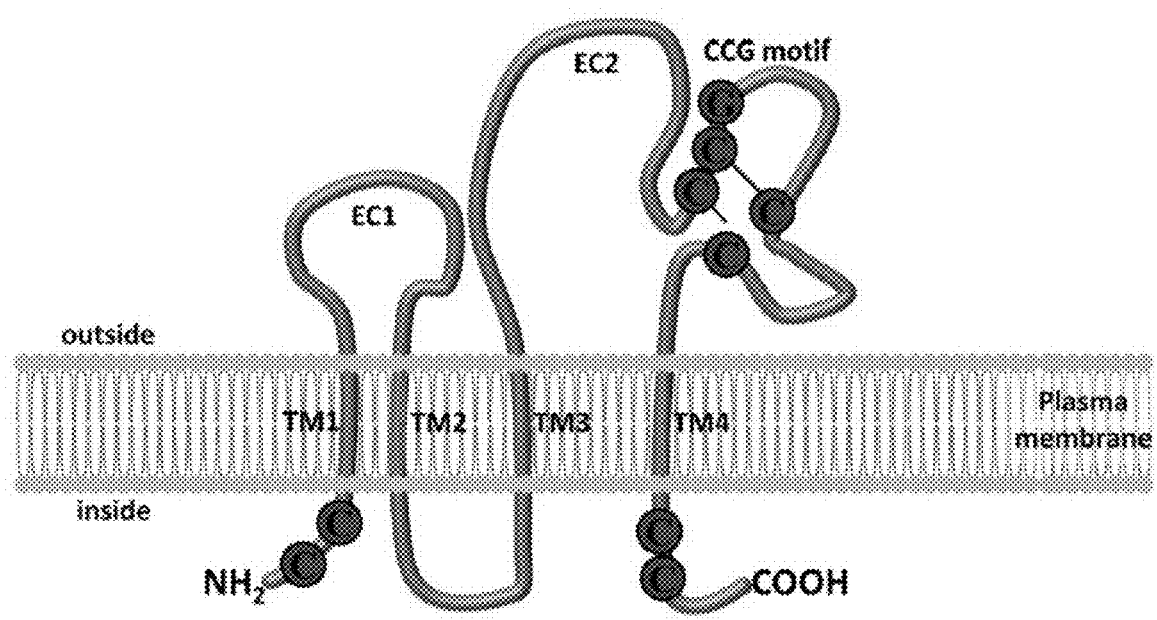
FIG. 2. Schematic diagram of tetraspanin proteins. Tetraspanins are comprising four transmembrane domains (TM1-4), intracellular N- and C-termini, and two extracellular domains (EC1 and EC2). CCG motif is formed by cysteine-cysteine-glycine and two disulfide bonds (thin lines) (from Zou et al. 2018).

Amatoxins are bicyclic peptides composed of 8 amino acids that are found in *Amanita phalloides* mushrooms (see FIG. 1). Amatoxins specifically inhibit the DNA-dependent RNA polymerase II of mammalian cells, and thereby also the transcription and protein biosynthesis of the affected cells. Inhibition of transcription in a cell causes stop of growth and proliferation. Though not covalently bound, the complex between amanitin and RNA-polymerase II is very tight (KD=3 nM). Dissociation of amanitin from the enzyme is a very slow process, thus making recovery of an affected cell unlikely. When the inhibition of transcription lasts sufficiently long, the cell will undergo programmed cell death (apoptosis).

The term "amatoxin" according to the invention includes all bicyclic peptides composed of 8 amino acids as isolated from the genus *Amanita* and described in Wieland, T. and Faulstich H. (Wieland T, Faulstich H., CRC Crit Rev Biochem. 5 (1978) 185-260), further all chemical derivatives thereof; further all semisynthetic analogs thereof; further all synthetic analogs thereof built from building blocks according to the master structure of the natural compounds (cyclic, 8 amino acids), and further all synthetic or semisynthetic analogs containing non-hydroxylated amino acids instead of the hydroxylated amino acids, further all synthetic or semisynthetic analogs, in which the sulfoxide moiety is replaced by a sulfone, thioether, or by atoms different from sulfur, e.g., a carbon atom as in a carbanalog of amanitin.

As used herein, a "derivative" of a compound refers to a species having a chemical structure that is similar to the compound, yet containing at least one chemical group not present in the compound it is derived from and/or deficient of at least one chemical group that is present in the compound it is derived from. The compound to which the derivative is compared to is known as the "parent" compound. Typically, a "derivative" may be produced from the parent compound in one or more chemical reaction steps.

As used herein, an "analogue" of a compound is structurally related but not identical to the compound and exhibits at least one activity of the compound. The compound to which the analogue is compared is known as the "parent" compound. The afore-mentioned activities include, without limitation: binding activity to another compound; inhibitory activity, e.g. enzyme inhibitory activity; toxic effects; activating activity, e.g. enzyme-activating activity. It is not required that the analogue exhibits such an activity to the same extent as the parent compound. A compound is regarded as an analogue within the context of the present application, if it exhibits the relevant activity to a degree of at least 1% (more preferably at least 5%, more preferably at least 10%, more preferably at least 20%, more preferably at least 30%, more preferably at least 40%, and more preferably at least 50%) of the activity of the parent compound. Thus, an "analogue of an amatoxin", as it is used herein, refers to a compound that is structurally related to any one of α-amanitin, β-amanitin, γ-amanitin, ε-amanitin, amanin, amaninamide, amanullin, and amanullinic acid and that exhibits at least 1% (more preferably at least 5%, more preferably at least 10%, more preferably at least 20%, more preferably at least 30%, more preferably at least 40%, 50%, 60%, and more preferably at least 70%, 80%, 90%) of the inhibitory activity against mammalian RNA polymerase II as compared to at least one of α-amanitin, β-amanitin, γ-amanitin, ε-amanitin, amanin, amaninamide, amanullin, and amanullinic acid. An "analogue of an amatoxin" suitable for use in the present invention may even exhibit a greater inhibitory activity against mammalian RNA polymerase II than any one of α-amanitin, β-amanitin, γ-amanitin, ε-amanitin, amanin, amaninamide, amanullin, or amanullinic acid. The inhibitory activity might be measured by determining the concentration at which 50% inhibition occurs ($IC_{50}$ value). The inhibitory activity against mammalian RNA polymerase II can be determined indirectly by measuring the inhibitory activity on cell proliferation, or alternatively, the inhibitory activity of the amatoxins and their respective derivatives as disclosed herein may e.g. be assessed using RNA polymerase II activity assays as disclosed in Voss et al. BMC Molecular Biology 2014, 15:7.

A "semisynthetic analogue" refers to an analogue that has been obtained by chemical synthesis using compounds from natural sources (e.g. plant materials, bacterial cultures, fungal cultures or cell cultures) as starting material. Typically, a "semisynthetic analogue" of the present invention has been synthesized starting from a compound isolated from a mushroom of the Amanitaceae family. In contrast, a "synthetic analogue" refers to an analogue synthesized by so-called total synthesis from small (typically petrochemical) building blocks. Usually, this total synthesis is carried out without the aid of biological processes.

According to some embodiments of the present invention, the amatoxin can be selected from the group consisting of α-amanitin, β-amanitin, amanin, amaninamide and analogues, derivatives and salts thereof.

Functionally, amatoxins are defined as peptides or depsipeptides that inhibit mammalian RNA polymerase II. Preferred amatoxins are those with a functional group (e.g. a carboxylic group, an amino group, a hydroxy group, a thiol or a thiol-capturing group) that can be reacted with linker molecules or target-binding moieties as defined below.

In the context of the present invention, the term "amanitins" particularly refers to bicyclic structures that are based on an aspartic acid or asparagine residue in position 1, a proline residue, particularly a hydroxyproline residue in position 2, an isoleucine, hydroxyisoleucine or dihydroxyisoleucine in position 3 (or aspartic acid for amanullic acid), a tryptophan or hydroxytryptophan residue in position 4 (or proline for proamanullin), glycine residues in positions 5 and 7 (or isoleucine residues in case of amanullic acid and proamanullin), an isoleucine residue in position 6, and a cysteine residue in position 8, particularly a derivative of cysteine that is oxidized to a sulfoxide or sulfone derivative (for the numbering and representative examples of amanitins, see FIG. 1), and furthermore includes all chemical derivatives thereof; further all semisynthetic analogues thereof; further all synthetic analogues thereof built from building blocks according to the master structure of the natural compounds (cyclic, 8 amino acids), further all synthetic or semisynthetic analogues containing non-hydroxylated amino acids instead of the hydroxylated amino acids, further all synthetic or semisynthetic analogues, in each case wherein any such derivative or analogue is functionally active by inhibiting mammalian RNA polymerase II.

The term "target-binding moiety", as used herein, refers to any molecule or part of a molecule that can specifically bind to a target molecule or target epitope. Preferred target-binding moieties in the context of the present application are (i) antibodies or antigen-binding fragments thereof; (ii) antibody-like proteins; and (iii) nucleic acid aptamers, (iv) anticalins, or (v) "target-binding moieties" suitable for use in the present invention typically have a molecular mass of 40 000 Da (40 kDa) or more.

A "linker" in the context of the present application refers to a molecule that increases the distance between two components, e.g. to alleviate steric interference between the target binding moiety and the amatoxin which may otherwise decrease the ability of the amatoxin to interact with RNA polymerase II. The linker may serve another purpose as it may facilitate the release of the amatoxin specifically in the cell being targeted by the target binding moiety. It is preferred that the linker and preferably the bond between the linker and the amatoxin on one side and the bond between the linker and the target binding moiety or antibody on the other side is stable under the physiological conditions out-side the cell, e.g. the blood, while it can be cleaved inside the cell, in particular inside the target cell, e.g. cancer cell. To provide this selective stability, the linker may comprise functionalities that are preferably pH-sensitive or protease sensitive. Alternatively, the bond linking the linker to the target binding moiety may provide the selective stability. Preferably a linker has a length of at least 1, preferably of 1-30 atoms length (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 atoms), wherein one side of the linker has been reacted with the amatoxin and, the other side with a target-binding moiety. In the context of the present invention, a linker preferably is a $C_{1-30}$-alkyl, $C_{1-30}$-heteroalkyl, $C_{2-30}$-alkenyl, $C_{2-30}$-heteroalkenyl, $C_{2-30}$-alkynyl, $C_{2-30}$-heteroalkynyl, cycloalkyl, heterocycloalkyl, aryl, heteroaryl, aralkyl, or a heteroaralkyl group, optionally substituted. The linker may contain one or more structural elements such as amide, ester, ether, thioether, disulfide, hydrocarbon moieties and the like. The linker may also contain combinations of two or more of these structural elements. Each one of these structural elements may be present in the linker more than once, e.g. twice, three times, four times, five times, or six times. In some embodiments the linker may comprise a disulfide bond. It is understood that the linker has to be attached either in a single step or in two or more subsequent steps to the amatoxin and the target binding moiety. To that end the linker to be will carry two groups, preferably at a proximal and distal end, which can (i) form a covalent bond to a group, preferably an activated group on an amatoxin or the target binding-peptide or (ii) which is or can be activated to form a covalent bond with a group on an amatoxin. Accordingly, if the linker is present, it is preferred that chemical groups are at the distal and proximal end of the linker, which are the result of such a coupling reaction, e.g. an ester, an ether, a urethane, a peptide bond etc. The presence of a "linker" is optional, i.e. the amatoxin may be directly linked to a residue of the target-binding moiety in some embodiments of the target-binding moiety toxin conjugate, however, in preferred embodiments of the invention the amatoxin is coupled to the target binding moiety via a linker.

The present invention further relates to a conjugate comprising a target binding moiety binding to CD37, at least one amatoxin and optionally a linker, wherein said target binding moiety is selected from the group consisting of
  (i) an antibody, preferably a monoclonal antibody,
  (ii) an antigen-binding fragment thereof, preferably a variable domain (Fv), a Fab fragment or an F(ab)2 fragment,
  (iii) an antigen-binding derivative thereof, preferably a single-chain Fv (scFv), and
  (iv) an antibody-like protein,
each binding to CD37, respectively.

In a preferred embodiment, said CD37 is human CD37 (SEQ ID No. 13); in the most preferred embodiment, it is the extracellular domain of human CD37 to which said target-binding moiety specifically binds to. The term "specifically binding" as used herein, refers to the binding of a targeting moiety of the invention, such as e.g. the anti-CD37 antibodies as disclosed herein, having a $K_D$ of at least about $10^{-6}$M, $10^{-7}$ M, $10^{-8}$M, or from about $10^{-8}$M to about $10^{-9}$M,
  $10^{-10}$M, $10^{-11}$M, $10^{-12}$M, or of about $5\times10^{-9}$M, $5\times10^{-10}$M to about $2.5\times10^{-11}$M, $5\times10^{-11}$M, $2.5\times10^{-12}$M, $5\times10^{-12}$M to its antigen, such as e.g. an epitope of human CD37, preferably an extracellular epitope of human CD37. The determination of the $K_D$ of the binding of a target-binding moiety of the invention, e.g. the antibodies as disclosed herein, may be determined according to the methodology disclosed in Kamat et al. Analytical Biochemistry 536 (2017) 16-31, or e.g. as disclosed in Noy-Porat et al. STAR Protoc. 2021 Sep. 15; 2(4):100836.

Said antibody, or antigen-binding fragment thereof or antigen-binding derivative thereof, can be a murine, a chimeric, a humanized or a human antibody, or antigen-binding fragment or antigen-binding derivative thereof, respectively.

As used herein, the term "antibody" shall refer to a protein consisting of one or more polypeptide chains encoded by immunoglobulin genes or fragments of immunoglobulin genes or cDNAs derived from the same. Said immunoglobulin genes include the light chain kappa, lambda and heavy chain alpha, delta, epsilon, gamma and mu constant region genes as well as any of the many different variable region genes.

The basic immunoglobulin (antibody) structural unit is usually a tetramer composed of two identical pairs of polypeptide chains, the light chains (L, having a molecular weight of about 25 kDa) and the heavy chains (H, having a molecular weight of about 50-70 kDa). Each heavy chain is comprised of a heavy chain variable region (abbreviated as VH or VH) and a heavy chain constant region (abbreviated as CH or CH). The heavy chain constant region is comprised of three domains, namely CH1, CH2 and CH3. Each light chain contains a light chain variable region (abbreviated as VL or VL) and a light chain constant region (abbreviated as CL or CL). The VH and VL regions can be further subdivided into regions of hypervariability, which are also called complementarity determining regions (CDRs) interspersed with regions that are more conserved called framework regions (FR). Each VH and VL region is composed of three CDRs and four FRs arranged from the amino terminus to the carboxy terminus in the order of FR1, CDR1, FR2, CDR2, FR3, CDR3, FR4. The variable regions of the heavy and light chains form a binding domain that interacts with an antigen.

The CDR and framework regions of an antibody may be defined according to different numbering schemes known in the art such as Kabat (E A Kabat, T T Wu, H. Bilofsky, M. Reid-Miller and H. Perry, Sequence of Proteins of Immunological Interest, National Institutes of Health, Bethesda (1983)), Chothia (Cothia & Lesk, J Mol Biol. 1987 Aug. 20; 196(4):901-17), or IMGT® (ImMunoGeneTics information, Lefranc et al. Dev Comp Immunol. (2003) 27:55-77.). In the context of the present invention, reference to CDRs is given according to Kabat.

The CDRs are most important for binding of the antibody or the antigen binding portion thereof. The FRs can be replaced by other sequences, provided the three-dimensional structure which is required for binding of the antigen is retained. Structural changes of the construct most often lead to a loss of sufficient binding to the antigen.

The term "antigen binding portion" of the (monoclonal) antibody refers to one or more fragments of an antibody which retain the ability to specifically bind to the CD20 antigen in its native form. Examples of antigen binding portions of the antibody include a Fab fragment, a monovalent fragment consisting of the VL, VH, CL and CH1 domains, an F(ab')2 fragment, a bivalent fragment comprising two Fab fragments linked by a disulfid bridge at the hinge region, an Fd fragment consisting of the VH and CH1 domain, an Fv fragment consisting of the VL and VH domains of a single arm of an antibody, and a dAb fragment which consists of a VH domain and an isolated complementarity determining region (CDR).

The antibody, or antibody fragment or antibody derivative thereof, according to the present invention can be a monoclonal antibody. As used herein, the term "monoclonal antibody" ("mAb") refers to a preparation of antibody molecules of single binding specificity and affinity for a particular epitope, representing a homogenous antibody population, i.e., a homogeneous population consisting of a whole immunoglobulin, or a fragment or derivative thereof. Preferably, such antibody is selected from the group consisting of IgG, IgD, IgE, IgA and/or IgM, or a fragment or derivative thereof, preferably the monoclonal antibody of the invention is of the IgG isotype, e.g. IgG1, or IgG4, more preferably of the IgG1 isotype.

As used herein, the term "fragment" or "antigen-binding fragment" shall refer to fragments of such antibody retaining target binding capacities, e.g., a CDR (complementarity determining region), a hypervariable region, a variable domain (Fv), an IgG heavy chain (consisting of VH, CH1, hinge, CH2 and CH3 regions), an IgG light chain (consisting of VL and CL regions), and/or a Fab and/or F(ab)2.

As used herein, the term "derivative" or "antigen-binding derivative" shall refer to protein constructs being structurally different from, but still having some structural relationship to, the common antibody concept, e.g., scFv, Fab and/or F(ab)2, as well as bi-, tri- or higher specific antibody constructs, all of which have about the same target-binding specificity as the monoclonal antibodies of the invention All these items are explained below.

Other antibody derivatives known to the skilled person are Diabodies, Camelid Antibodies, Domain Antibodies, bivalent homodimers with two chains consisting of scFvs, IgAs (two IgG structures joined by a J chain and a secretory component), shark antibodies (IgNAR), antibodies consisting of new world primate framework plus non-new world primate CDR, dimerised constructs comprising CH3+VL+VH, other scaffold protein formats comprising CDRs, and antibody conjugates (e.g., antibody, or fragments or derivatives thereof, linked to a drug, a toxin, a cytokine, an aptamer, a nucleic acid such as a desoxyribonucleic acid (DNA) or ribonucleic acid (RNA), a therapeutic polypeptide, a radioisotope or a label).

As used herein, the term "antibody-like protein" refers to a protein that has been engineered (e.g. by mutagenesis of Ig loops) to specifically bind to a target molecule. Typically, such an antibody-like protein comprises at least one variable peptide loop attached at both ends to a protein scaffold. This double structural constraint greatly increases the binding affinity of the antibody-like protein to levels comparable to that of an antibody. The length of the variable peptide loop typically consists of 10 to 20 amino acids. The scaffold protein may be any protein having good solubility properties. Preferably, the scaffold protein is a small globular protein. Antibody-like proteins include without limitation affilin proteins, affibodies, anti-calins, and designed ankyrin repeat proteins (Binz et al., 2005). Antibody-like proteins can be derived from large libraries of mutants, e.g. by panning from large phage display libraries, and can be isolated in analogy to regular antibodies. Also, antibody-like binding proteins can be obtained by combinatorial mutagenesis of surface-exposed residues in globular proteins.

Antibody-like proteins according to the invention may e.g. also include single-domain antibody fragments (dAbs), also known as nanobodies which consist of VH or VL domains of 12-15 kDa and are the smallest functional antibody fragments that retain full antigen-binding specificity such as for example the camelid VH domains (VHH) and the shark VH domains called V-NAR, the antigen-binding domain of IgNARs (see e.g. English et al. Antibody Therapeutics, 2020, Vol. 3, No. 11-9).

As used herein, the term "Fab" relates to an IgG fragment comprising the antigen binding region, said fragment being composed of one constant and one variable domain from each heavy and light chain of the antibody.

As used herein, the term "F(ab)2" relates to an IgG fragment consisting of two Fab fragments connected to one another by disulfide bonds.

As used herein, the term "scFv" relates to a single-chain variable fragment being a fusion of the variable regions of the heavy and light chains of immunoglobulins, linked together with a short linker, usually comprising serine (S) and/or glycine (G) residues. This chimeric molecule retains the specificity of the original immunoglobulin, despite removal of the constant regions and the introduction of a linker peptide.

Modified antibody formats are for example bi- or trispecific antibody constructs, antibody-based fusion proteins, immunoconjugates and the like.

IgG, scFv, Fab and/or F(ab)2 are antibody formats which are well known to the skilled person. Related enabling techniques are available from respective textbooks.

According to preferred embodiments of the present invention, said antibody, or antigen-binding fragment thereof or antigen-binding derivative thereof, is a murine, a chimeric, a humanized or a human antibody, or antigen-binding fragment or antigen-binding derivative thereof, respectively, more preferably, said antibody or antigen-binding fragment thereof is a humanized or a human antibody.

Monoclonal antibodies (mAb) derived from mouse may cause unwanted immunological side-effects due to the fact that they contain a protein from another species which may elicit anti-drug antibodies. In order to overcome this problem, antibody humanization and maturation methods have been designed to generate antibody molecules with minimal immunogenicity when applied to humans, while ideally still retaining specificity and affinity of the non-human parental antibody (for review see Almagro and Fransson 2008). Using these methods, e.g., the framework regions of a mouse mAb are replaced by corresponding human framework regions (so-called CDR grafting). WO200907861 discloses the generation of humanized forms of mouse antibodies by linking the CDR regions of non-human antibodies to human constant regions by recombinant DNA technology. U.S. Pat. No. 6,548,640 by Medical Research Council describes CDR grafting techniques, and U.S. Pat. No. 5,859,205 by Celltech describes the production of humanised antibodies.

As used herein, the term "chimeric antibody" relates to an antibody consisting of the antibody's original antigen-binding variable domains with the constant domains being derived from a different species. Since antibodies, in particular monoclonal antibodies, originally most often have been derived from mouse, typically chimeric antibodies are containing human constant domains and mouse variable domains, in order to reduce immunogenicity in humans. Examples of chimeric antibodies used in clinical therapy include infliximab, rituximab and abciximab.

As used herein, the term "humanized antibody" relates to an antibody, a fragment or a derivative thereof, in which at least a portion of the constant regions and/or the framework regions, and optionally a portion of CDR regions, of the antibody is derived from or adjusted to human immunoglobulin sequences.

The antibodies, the antibody fragments or antibody derivatives thereof, disclosed herein can comprise humanized sequences, in particular of the preferred VH- and VL-based antigen-binding region which maintain appropriate ligand affinity. The amino acid sequence modifications to obtain said humanized sequences may occur in the CDR regions and/or in the framework regions of the original antibody and/or in antibody constant region sequences.

Said antibody, or antibody fragment or antibody derivative thereof, can be glycosylated. The glycan can be an N-linked oligosaccharide chain at asparagin 297 of the heavy chain.

The antibodies or fragments or derivatives of the present invention may be produced by transfection of a host cell with an expression vector comprising the coding sequence for the antibody according to the invention. The expression vector or recombinant plasmid is produced by placing the coding antibody sequences under control of suitable regulatory genetic elements, including promoter and enhancer sequences like, e.g., a CMV promoter. Heavy and light chain sequences might be expressed from individual expression vectors which are co-transfected, or from dual expression vectors. Said transfection may be a transient transfection or a stabile transfection. The transfected cells are subsequently cultivated to produce the transfected antibody construct. When stabile transfection is performed, then stable clones secreting antibodies with properly associated heavy and light chains are selected by screening with an appropriate assay, such as, e.g., ELISA, subcloned, and propagated for future production. Corresponding methods for the transient or stable transfection of mammalian cells for the expression of monoclonal antibodies have been described in prior art. For example, Jager et al. BMC Biotechnology 2013, 13:52 discloses a method for the transient production of recombinant antibodies in HEK293 cells, Kamle et al Advances in Protein Molecular and Structural Biology Methods (2022) p. 31-39 discloses alternative methods for transient expression and purification of antibodies. Methods for generating stable cell clones are e.g. disclosed in US 2010/0311116 A1, or U.S. Pat. No. 7,491,532 B2. Guidelines to cell engineering for monoclonal antibody production are e.g. reported by Costa, R. A., et al. Eur. J. Pharmaceut. Biopharmaceut. 74 (2010) 127-138. Kim, D. W., et al., report the use of the human elongation factor 1 alpha promoter as a versatile and efficient expression system (Gene 91 (1990) 217-223). Comparison of intron-dependent and intron independent gene expression is reported by Buchman, A. R., et al. (Mol. Cell. Biol. 8 (1988) 4395-4405).

According to embodiments of the present invention, said antibody, or antigen-binding fragment thereof, or antigen-binding derivative thereof, respectively, can be selected from the group consisting of or can be derived from, respectively, Tetulomab (Lilotomab), Otlertuzumab (TRU-016), and Naratuximab, BI 836826, or Gen3009.

In a preferred embodiment of the present invention, in the conjugate comprising an antibody, or antigen-binding fragment thereof, or antigen-binding derivative thereof, or an antibody-like protein, at least one amatoxin and optionally a linker, said antibody, or fragment or derivative thereof, or antibody-like protein, comprises the following complementarity-determining regions (CDRs):

CDRH1 according to SEQ ID No. 1 (DYNMY),
CDRH2 according to SEQ ID No. 2 (YIDPYNGDT-TYNQKFKG),
CDRH3 according to SEQ ID No. 3 (SPYGHYAMDY),
CDRL1 according to SEQ ID No. 4 (KASQDVSTAVD),
CDRL2 according to SEQ ID No. 5 (WASTRHT),
CDRL3 according to SEQ ID No. 6 (RQHYSTPFT), wherein said CDRs are comprised in a suitable protein or amino acid framework so as to be capable of binding to CD37, preferably to human CD37, most preferably to the extracellular domain of human CD37, particularly preferably to an epitope comprised in or formed by EC1 and/or EC2 of human CD37, wherein EC1 comprises or consist of amino acids 39-59 of SEQ ID NO. 13, and EC2 comprises or consists of amino acids 112-241 of SEQ ID No. 13. The term "epitope" as used herein refers to the part of a macromolecule, preferably a polypeptide, that is recognized by antigen-binding molecules, such as the antibody, or antigen-binding fragment thereof, or antigen-binding derivative thereof of the invention as disclosed herein, and more particularly by the antigen-binding site of said molecules. Epitopes define the minimum binding site for an antibody molecule, and thus represent the target of specificity of an antibody molecule. Epitopes can be further defined as structural epitopes or functional epitopes. A "structural epitope" consists of amino acids or other molecules in a region that is in close contact with the antibody usually revealed by a structure. A "functional epitope" is defined, as those parts of a molecule that make an energetic contribution to binding such that when they are changed there is a decrease in binding affinity. Structural epitopes may e.g. be a linear continuous sequence of about 5 amino acids to about 10, 15, 20, 25, 30, 40, 45, 50, 100 amino acids in length, or of about 6, 7, 8, 9, 10, 15, 20, 25, 30, 35, 40, 45 to about 50, 75, 100 amino acids, or a conformational epitope which is formed by the three dimensional structure of the polypeptide and which may comprise discontinuous amino acids of the polypeptide.

In one embodiment, the antibody, or antigen-binding fragment thereof, or antigen-binding derivative thereof comprised in the conjugate according to the invention as disclosed above specifically binds to a conformational epitope which is formed by amino acids 39-59 of SEQ ID NO. 13, and/or by amino acids 112-241 of SEQ ID No. 13. Said conformational epitope may be formed by more than one CD37 protein, e.g. by two, three or four CD37 molecules which form a multimer.

In one embodiment, the antibody, or antigen-binding fragment thereof, or antigen-binding derivative thereof of the invention comprised in the conjugate according to the invention as disclosed above does not specifically bind to cynomolgous CD37 comprising the amino acid sequence according to SEQ ID NO: 13. Accordingly, the antibody, or antigen-binding fragment thereof, or antigen-binding derivative thereof comprised in the conjugate according to the invention does not specifically bind to cynomolgus CD37 comprising or consisting of the amino acid sequence according to SEQ ID NO: 16. The term "no specific binding" or any grammatical equivalent thereof as used herein shall indicate that the antibody, or antigen-binding fragment thereof, or antigen-binding derivative thereof of the invention comprised in the conjugate according to the invention has a $K_D$ of $>10^{-6}$M, $10^{-5}$M. $10^{-4}$ M.

In a further preferred embodiment of the present invention, said antibody, or antigen-binding fragment thereof, or antigen-binding derivative thereof, or antibody-like protein, respectively, comprises a heavy chain variable region having at least 90% sequence similarity to an amino acid sequence according to SEQ ID No. 7, preferably at least 95% sequence similarity to an amino acid sequence according to SEQ ID No. 7, most preferably consisting of an amino acid sequence according to SEQ ID No. 7, and a light chain variable region having at least 90% sequence similarity to an amino acid sequence according to SEQ ID No. 8, preferably at least 95% sequence similarity to an amino acid sequence according to SEQ ID No. 8, most preferably consisting of an amino acid sequence according to SEQ ID No. 8. The term "sequence similarity" or "sequence identity" both of which are used interchangeably throughout the present invention refer to the similarity or identity of two or more amino acid or polynucleotide sequences to each other or to a reference sequence.

Sequence identity according to the invention may e.g. be determined over the whole length of each of the sequences being compared to a respective reference sequence (so-called "global alignment"), that is particularly suitable for sequences of the same or similar length, or over shorter, defined lengths (so-called "local alignment"), that is more suitable for sequences of unequal length. In the above context, an amino acid sequence having a "sequence identity" of at least, for example, 95% to a query amino acid sequence, is intended to mean that the sequence of the subject amino acid sequence is identical to the query sequence except that the subject amino acid sequence may include up to five amino acid alterations per each 100 amino acids of the query amino acid sequence. In other words, to obtain an amino acid sequence having a sequence of at least 95% identity to a query amino acid sequence, up to 5% (5 of 100) of the amino acid residues in the subject sequence may be inserted or substituted with another amino acid or deleted. Sequence identity may e.g. be calculated over the entire length of SEQ ID No. 7, or SEQ ID No. 8, according to one embodiments, sequence identity to SEQ ID No. 7, or SEQ ID No. 8 is calculated over the length of the framework regions of SEQ ID No. 7, or SEQ ID No. 8, excluding the amino acid sequences of SEQ ID NO: 1, SEQ ID NO: 2, SEQ ID NO: 3 in SEQ ID NO: 7 for the calculation of sequence identity and/or excluding the amino acid sequences of SEQ ID NO: 4, SEQ ID NO: 5, SEQ ID NO: 6 in SEQ ID NO: 8 for the calculation of sequence identity.

Methods for comparing the identity and sequence similarity of two or more sequences are well known in the art. The percentage to which two sequences are identical can for example be determined by using a mathematical algorithm. A preferred, but not limiting, example of a mathematical algorithm which can be used is the algorithm of Karlin et al. (1993), PNAS USA, 90:5873-5877. Such an algorithm is integrated in the BLAST family of programs (see also Altschul et al., 1990, J. Mol. Biol. 215, 403-410 or Altschul et al. (1997), Nucleic Acids Res, 25:3389-3402), accessible through the home page of the NCBI at world wide web site ncbi.nlm.nih.gov) and FASTA (Pearson (1990), Methods Enzymol. 83, 63-98; Pearson and Lipman (1988), Proc. Natl. Acad. Sci. U.S.A 85, 2444-2448.). Sequences which are identical to other sequences to a certain extent can be identified by these programs. Furthermore, programs available in the Wisconsin Sequence Analysis Package (Devereux et al, 1984, Nucleic Acids Res., 387-395; Womble Methods Mol Biol. 2000; 132:3-22), for example the programs BESTFIT and GAP, may be used to determine the % identity between two polypeptide sequences. BESTFIT uses the "local sequence similarity" algorithm of (Smith and Waterman (1981), J. Mol. Biol. 147, 195-197.) and finds the best single region of similarity between two sequences. For example "gapped BLAST" may be utilized as described in Altschul et al., 1997, Nucleic Acids Res. 25:3389-3402. Alternatively, PSI-Blast can be used to perform an iterated search which detects distant relationships between molecules. When using any of the above BLAST, Gapped BLAST programs, the default parameters of the respective programs (e.g.,)(BLAST and NBLAST) may be used.

In a further preferred embodiment of the present invention, said antibody as described above comprises a heavy chain having at least 90% sequence similarity to an amino acid sequence according to SEQ ID No. 9, preferably at least 95% sequence similarity to an amino acid sequence according to SEQ ID No. 9, most preferably consisting of an amino acid sequence according to SEQ ID No. 9, and a light chain having at least 90% sequence similarity to an amino acid sequence according to SEQ ID No. 12, preferably at least 95% sequence similarity to an amino acid sequence according to SEQ ID No. 12, most preferably consisting of an amino acid sequence according to SEQ ID No. 12.

The antibody of the invention comprising a heavy chain consisting of an amino acid sequence according to SEQ ID No. 9 and a light chain consisting of an amino acid sequence according to SEQ ID No. 12 is termed "chHH1-HDP" herein.

According to preferred embodiments of the present invention, said antibodies as described above have been genetically engineered to comprise a heavy chain 118Cys, a heavy chain 239Cys, and/or heavy chain 265Cys according to the EU numbering system (Edelman, G. M. et al., Proc. Natl. Acad. USA, 63, 78-85 (1969), preferably a heavy chain 265Cys according to the EU numbering system, and wherein said linker, if present, or said amatoxin is connected to said antibody via said heavy chain 118Cys, or said heavy chain 239Cys, or heavy chain 265Cys residue, respectively, more preferably said amatoxin is connected to said antibody via said heavy chain 265Cys Accordingly, said genetically engineered heavy chain 118Cys, heavy chain 239Cys, and/or heavy chain 265Cys residues can be used for coupling the antibody to said linker, if present, or said amatoxin.

As used herein, the term "genetically engineered" or "genetic engineering" relates to the modification of the amino acid sequence or part thereof of a given or natural polypeptide or protein in the sense of nucleotide and/or amino acid substitution, insertion, deletion or reversion, or any combinations thereof, by gene technological methods, such as, e.g., site-directed mutagenesis as described in Biochem. J. (1986) Vol. 237: 1-7, or J Biol Chem. (2015) Vol. 290(5): 2577-2592.

As used herein, the term "amino acid substitution" relates to modifications of the amino acid sequence of the protein, wherein one or more amino acids are replaced with the same number of different amino acids, producing a protein which contains a different amino acid sequence than the original protein. A conservative amino acid substitution is understood to relate to a substitution which due to similar size, charge, polarity and/or conformation does not significantly affect the structure and function of the protein. Groups of conservative amino acids in that sense represent, e.g., the non-polar amino acids Gly, Ala, Val, Ile and Leu; the aromatic amino acids Phe, Trp and Tyr; the positively charged amino acids Lys, Arg and His; and the negatively charged amino acids Asp and Glu. Exemplary amino acid substitutions are presented in Table 1 below:

| Original residues | Examples of substitutions |
| --- | --- |
| Ala (A) | Val, Leu, Ile, Gly |
| Arg (R) | His, Lys |
| Asn (N) | Gln |
| Asp (D) | Glu |
| Cys (C) | Ser |
| Gln (Q) | Asn |
| Glu (E) | Asp |
| Gly (G) | Pro, Ala |

-continued

| Original residues | Examples of substitutions |
|---|---|
| His (H) | Lys, Arg |
| Ile (I) | Leu, Val, Met, Ala, Phe |
| Leu (L) | Ile, Val, Met, Ala, Phe |
| Lys (K) | Arg, His |
| Met (M) | Leu, Ile, Phe |
| Phe (F) | Leu, Val, Ile, Tyr, Trp, Met |
| Pro (P) | Ala, Gly |
| Ser (S) | Thr |
| Thr (T) | Ser |
| Trp (W) | Tyr, Phe |
| Tyr (Y) | Trp, Phe |
| Val (V) | Ile, Met, Leu, Phe, Ala |

According to preferred embodiments of the present invention, the antibody of said conjugate as described above has been genetically engineered to comprise a heavy chain 234Ala and/or 235Ala according to the EU numbering system.

According to even more preferred embodiments of the present invention, the antibody of said conjugate as described above has been genetically engineered to comprise a heavy chain 265Cys, 234Ala and 235Ala according to the EU numbering system, and said linker, if present, or said amatoxin is connected to said antibody via said heavy chain 265Cys residue.

According to particularly preferred embodiments of the present invention, the antibody of said conjugate as described above comprises a heavy chain having at least 90% sequence similarity to an amino acid sequence according to SEQ ID No. 10 or 11, preferably at least 95% sequence similarity to an amino acid sequence according to SEQ ID No. 10 or 11, most preferably consisting of an amino acid sequence according to SEQ ID No. 10 or 11, and a light chain having at least 90% sequence similarity to an amino acid sequence according to SEQ ID No. 12, preferably at least 95% sequence similarity to an amino acid sequence according to SEQ ID No. 12, most preferably consisting of an amino acid sequence according to SEQ ID No. 12.

The antibody comprising a heavy chain consisting of an amino acid sequence according to SEQ ID No. 10 and a light chain consisting of an amino acid sequence according to SEQ ID No. 12 is termed "chHH1-HDP-D265C" herein. The heavy chains of this antibody comprise genetically engineered 265Cys residues according to the EU numbering system.

The antibody comprising a heavy chain consisting of an amino acid sequence according to SEQ ID No. 11 and a light chain consisting of an amino acid sequence according to SEQ ID No. 12 is termed "chHH1-HDP-LALA-D265C" herein. The heavy chains of this antibody are comprising genetically engineered 234Ala and 235Ala residues and 265Cys residues according to the EU numbering system.

In a preferred embodiment of the present invention, the antibody, or antibody fragment or antibody derivative thereof, of said conjugate binds to an extracellular domain of the CD37 molecule.

In a preferred embodiment, the invention relates to a conjugate comprising an antibody, or antibody fragment or antibody derivative thereof as described above, which binds to the extracellular domain of CD37.

Furthermore, the conjugate according to the present invention can have a cytotoxic activity of an $IC_{50}$ better than $10 \times 10^{-9}$ M, $9 \times 10^{-9}$ M, $8 \times 10^{-9}$ M, $7 \times 10^{-9}$ M, $6 \times 10^{-9}$ M, $5 \times 10^{-9}$ M, $4 \times 10^{-9}$ M, $3 \times 10^{-9}$ M, $2 \times 10^{-9}$ M, preferably better than $10 \times 10^{-m}$ M, $9 \times 10^{-1o}$ M, $8 \times 10^{-1o}$ M, $7 \times 10^{-1o}$ M, $6 \times 10^{-1o}$ M, $5 \times 10^{-1o}$ M, $4 \times 10^{-1o}$ M, $3 \times 10^{-1o}$ M, $2 \times 10^{-1o}$ M, and more preferably better than $10 \times 10^{-11}$ M, $9 \times 10^{-11}$ M, $8 \times 10^{-11}$ M, $7 \times 10^{-11}$ M, $6 \times 10^{-11}$ M, $5 \times 10^{-11}$ M, $4 \times 10^{-11}$ M, $3 \times 10^{-11}$ M, $2 \times 10^{-11}$ M, or $1 \times 10^{-11}$ M.

According to an embodiment of the present invention, said linker, if present, or said amatoxin is connected to said antibody via any of the naturally occurring Cys residues of said antibody, preferably via any of the naturally occurring Cys residues which form the interchain disulfide bonds of said antibody, and/or via a disulfide linkage and may e.g. be done as disclosed in Behrens et al. Mol Pharm. 2015 Nov. 2; 12(11): 3986-3998.

According to a preferred embodiment of the present invention, said linker, if present, is connected or coupled to said antibody via one or more of the engineered cysteine residues heavy chain 118Cys, a heavy chain 239Cys, and/or heavy chain 265Cys. The conjugation of the linker to said cysteine-engineered antibody may e.g. be done as disclosed in WO 2016/142049 A1.

According to preferred embodiments of the present invention, said conjugate as described comprises a linker, wherein said linker can be a non-cleavable or a cleavable linker.

In some embodiments, the linker conjugating the antibody or antigen binding fragment thereof and the amatoxin is non-cleavable. Non-cleavable linkers comprise stable chemical bonds that are resistant to degradation (e.g., proteolysis). Generally, non-cleavable linkers require proteolytic degradation inside the target cell, and exhibit high extracellular stability. Non-cleavable linkers suitable for use herein further may include one or more groups selected from a bond, —(C═O)—, $C_1$-$C_6$ alkylene, $C_1$-$C_6$ heteroalkylene, $C_2$-$C_6$ alkenylene, $C_2$-$C_6$ heteroalkenylene, $C_2$-$C_6$ alkynylene, $C_2$-$C_6$ heteroalkynylene, $C_3$-$C_6$ cycloalkylene, heterocycloalkylene, arylene, heteroarylene, and combinations thereof, each of which may be optionally substituted, and/or may include one or more heteroatoms (e.g., S, N, or O) in place of one or more carbon atoms. Non-limiting examples of such groups include $(CH2)_p$, $(C═O)(CH2)_p$, and polyethyleneglycol (PEG; $(CH2CH2O)_p$), units, wherein p is an integer from 1-6, independently selected for each occasion.

In some embodiments, the non-cleavable linker according to the invention comprises one or more of a bond, —(C═O)—, a —C(O)NH— group, an —OC(O)NH— group, $C_1$-$C_6$ alkylene, $C_1$-$C_6$ heteroalkylene, $C_2$-$C_6$ alkenylene, $C_2$-$C_6$ heteroalkenylene, $C_2$-$C_6$ alkynylene, $C_2$-$C_6$ heteroalkynylene, $C_3$-$C_6$ cycloalkylene, heterocycloalkylene, arylene, heteroarylene, a —$(CH2CH2O)_p$— group where p is an integer from 1-6.

In some embodiments, each $C_1$-$C_6$ alkylene, $C_1$-$C_6$ heteroalkylene, $C_2$-$C_6$ alkenylene, $C_2$-$C_6$ heteroalkenylene, $C_2$-$C_6$ alkynylene, $C_2$-$C_6$ heteroalkynylene, $C_3$-$C_6$ cycloalkylene, heterocycloalkylene, arylene, or heteroarylene may optionally be interrupted by one or more heteroatoms selected from O, S and N and may be optionally substituted with from 1 to 5 substituents independently selected for each occasion from the group consisting of alkyl, alkenyl, alkynyl, cycloalkyl, heterocycloalkyl, alkaryl, alkyl heteroaryl, amino, ammonium, acyl, acyloxy, acylamino, aminocarbonyl, alkoxycarbonyl, ureido, carbamate, aryl, heteroaryl, sulfinyl, sulfonyl, hydroxyl, alkoxy, sulfanyl, halogen, carboxy, trihalomethyl, cyano, hydroxy, mercapto, and nitro.

In one embodiment, the non-cleavable linker of the invention comprises a —$(CH2)_n$- unit, wherein n is an integer from 2-12, or from 2-6, or from 6-12, e.g. 2, 3, 4, 5, 6, 7, 8, 9, 10, 11, 12.

In a preferred embodiment, the non-cleavable linker of the invention comprises a —(CH2)$_n$ unit, wherein n is 4, 5, or 6, more preferably, wherein n is 6.

In particularly preferred embodiments, the non-cleavable linker of the invention is —(CH2)$_n$- wherein n=6, represented by the formula:

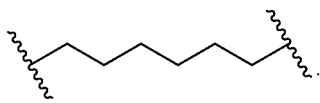 [SMILES: *CCCCCC*]

According to some embodiments, the non-cleavable linkers of the invention as disclosed herein comprise a thiol reactive group, selected from bromo acetamide, iodo acetamide, methylsulfonylbenzothiazole, 4,6-dichloro-1,3,5-triazin-2-ylamino group methyl-sulfonyl phenyltetrazole or methyl sulfonyl phenyloxadiazole, pyridine-2-thiol, 5-nitro-pyridine-2-thiol, methanethiosulfonate, or a maleimide.

According to a preferred embodiment the thiol reactive group is a maleimide (meleimidyl moiety) as depicted below:

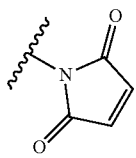 [SMILES: *N1C(=O)C=CC1=O]

According to a preferred embodiment, the non-cleavable linker of the invention comprising the thiol reactive group maleimide (meleimidyl moiety) has the structure prior to coupling to the amatoxin of the invention as disclosed herein:

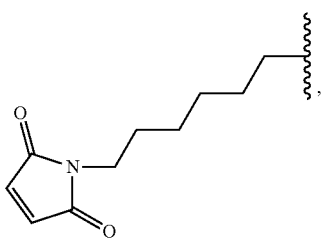 [SMILES: *CCCCCCN1C(=O)C=CC1=O]

and may also be referred to as 1-n-hexyl-maleimide, which is a non-cleavable linker. The wavy line at the linker terminus indicates the point of attachment to the amatoxin. Following the conjugation of the linker-amatoxin to a reactive cysteine of an antibody of the invention as disclosed herein, e.g. Cys265 of the heavy chain of cysteine engineered antibodies of the invention as disclosed herein, the said linker has the structure:

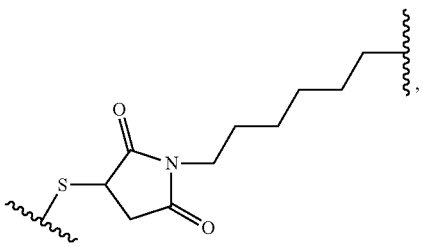

where S is a sulfur atom which represents the reactive substituent present within an antibody, or antigen-binding fragment thereof, that specifically binds to human CD37. The wavy line at the linker terminus indicates the point of attachment to the amatoxin. The foregoing linker moieties and amatoxin-linker conjugates, among others useful in conjunction with the compositions and methods described herein, are described, for example, in patent application publication WO 2014/043403 A1 and Patent Application Publication No. WO2017/149077, the disclosure of each of which is incorporated herein by reference in its entirety.

A "cleavable linker" according to the invention is understood as comprising at least one cleavage site. As used herein, the term "cleavage site" shall refer to a moiety that is susceptible to specific cleavage at a defined position under particular conditions. Said conditions are, e.g., specific enzymes or a reductive environment in specific body or cell compartments. For example, linkers that cleaved under reducing conditions may include N-acyl hydrazone-based linkers as e.g. disclosed in Bargh et al. Chem Soc Rev. 2019 Aug. 12; 48(16):4361-4374. Linkers cleavable under reducing conditions include, for example, a disulfide. A variety of disulfide linkers are known in the art, including, for example, those that can be formed using SATA (N-succinimidyl-S-acetylthioacetate), SPDP (N-succinimidyl-3-(2-pyridyldithio)propionate), SPDB (N-succinimidyl-3-(2-pyridyldithio)butyrate) and SMPT (N-succinimidyl-oxycarbonyl-alpha-methyl-alpha-(2-pyridyl-dithio) toluene), SPDB and SMPT (See, e.g., Thorpe et al., 1987, Cancer Res. 47:5924-5931; Wawrzynczak et al., In Immunoconjugates: Antibody Conjugates in Radioimagery and Therapy of Cancer (C. W. Vogel ed., Oxford U. Press, 1987. See also U.S. Pat. No. 4,880,935, the disclosure of each of which is incorporated herein by reference in its entirety as it pertains to linkers suitable for covalent conjugation.

According to one embodiment, the cleavable linker according to the invention is cleaved under high Fe(II) concentration and includes e.g. Fe(II)-reactive 1,2,4-trioxolane scaffold (TRX). Such linkers may be particularly useful for the treatment of tumors which are characterized by a higher Fe(II) concentration within the tumor cells. Corresponding linkers are e.g. disclosed in Spangler et al. Mol Pharm. 2018 May 7; 15(5):2054-2059. Linkers that may e.g. be used in case a lysosomal release of the ADC payload is desired include disulfide conjugates as disclosed in Pillow et al. Chem. Sci., 2017, 8, 366-370. Alternative linkers which are hydrolysable under acidic conditions include e.g. hydrazones, semicarbazones, thiosemicarbazones, cis-aconitic amides, orthoesters, acetals, ketals, or the like. (See, e.g., U.S. Pat. Nos. 5,122,368; 5,824,805; 5,622,929; Dubowchik and Walker, 1999, Pharm. Therapeutics 83:67-123; Neville et al., 1989, Biol. Chem. 264:14653-14661, the disclosure of each of which is incorporated herein by reference in its entirety as it pertains to linkers suitable for covalent conjugation. Such linkers are not cleaved under neutral pH conditions, such as those in the blood, but are cleavable or undergo self-cleavage at below pH 5.5 or 5.0, the approximate pH of the lysosome.

An enzymatically cleavable moiety according to the invention may also be referred to as "cleavable by an enzyme". Enzymatic cleavage of the linker results in the intracellular release of the toxin cargo conjugated to the targeting moiety or antibody as disclosed herein, or a metabolite thereof after internalization (see Dubowchik et al., Bioconjug Chem. 13 (2002) 855-69).

Said cleavable linker can be selected from the group consisting of an enzymatically cleavable linker, preferably a protease-cleavable linker, and a chemically cleavable linker, preferably a linker comprising a disulfide bridge.

According to preferred embodiments of the present invention, the cleavage site is an enzymatically cleavable moiety comprising two or more amino acids. Preferably, said enzymatically cleavable moiety comprises a valine-alanine (Val-Ala), valine-citrulline (Val-Cit), valine-lysine (Val-Lys), valine-arginine (Val-Arg) dipeptide, a phenylalanine-lysine-glycine-proline-leucin-glycine (Phe Lys Gly Pro Leu Gly) or alanine-alanine-proline-valine (Ala Ala Pro Val) peptide, or a β-glucuronide or β-galactoside.

According to some embodiments, said cleavage site can be cleavable by at least one protease selected from the group consisting of cysteine protease, metalloprotease, serine protease, threonine protease, and aspartic protease.

Cysteine proteases, also known as thiol proteases, are proteases that share a common catalytic mechanism that involves a nucleophilic cysteine thiol in a catalytic triad or dyad.

Metalloproteases are proteases whose catalytic mechanism involves a metal. Most metalloproteases require zinc, but some use cobalt. The metal ion is coordinated to the protein via three ligands. The ligands co-ordinating the metal ion can vary with histidine, glutamate, aspartate, lysine, and arginine. The fourth coordination position is taken up by a labile water molecule.

Serine proteases are enzymes that cleave peptide bonds in proteins; serine serves as the nucleophilic amino acid at the enzyme's active site. Serine proteases fall into two broad categories based on their structure: chymotrypsin-like (trypsin-like) or subtilisin-like.

Threonine proteases are a family of proteolytic enzymes harbouring a threonine (Thr) residue within the active site. The prototype members of this class of enzymes are the catalytic subunits of the proteasome, however, the acyltransferases convergently evolved the same active site geometry and mechanism.

Aspartic proteases are a catalytic type of protease enzymes that use an activated water molecule bound to one or more aspartate residues for catalysis of their peptide substrates. In general, they have two highly conserved aspartates in the active site and are optimally active at acidic pH. Nearly all known aspartyl proteases are inhibited by pepstatin.

In particular embodiments of the present invention, the cleavable site is cleavable by at least one agent selected from the group consisting of Cathepsin A or B, matrix metalloproteinases (MMPs), elastases, β-glucuronidase and β-galactosidase, preferably Cathepsin B.

In particularly preferred embodiments, the enzymatically cleavable linker according to the invention comprises a dipeptide selected from Phe-Lys, Val-Lys, Phe-Ala, Val-Ala, Phe-Cit and Val-Cit, particularly wherein the cleavable linker further comprises a p-aminobenzyl (PAB) spacer between the dipeptides and the amatoxin:

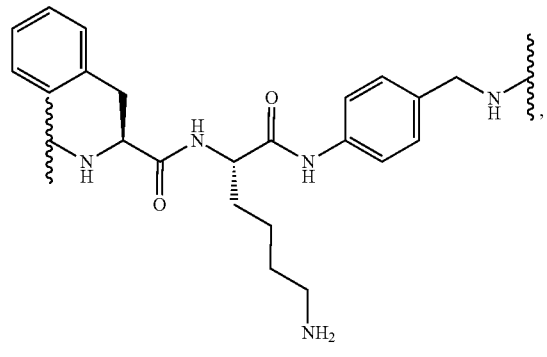

Phe-Lys-PAB

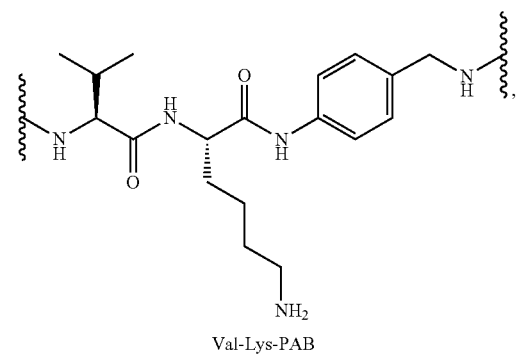

Val-Lys-PAB

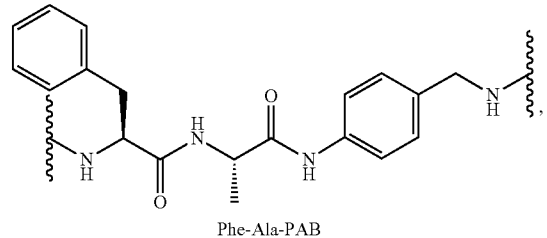

Phe-Ala-PAB

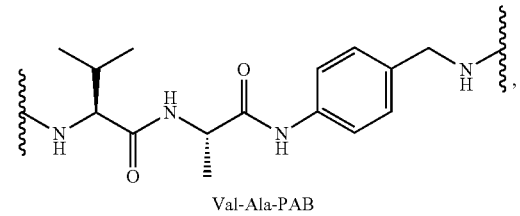

Val-Ala-PAB

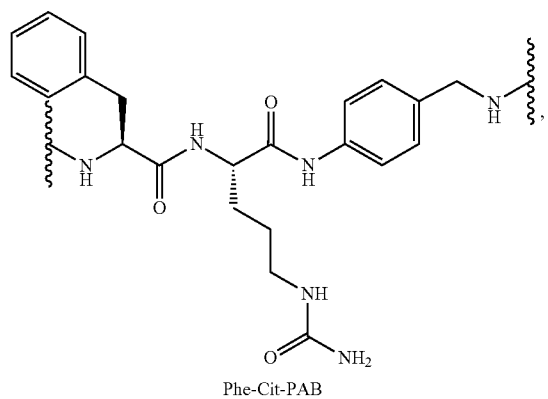

Phe-Cit-PAB

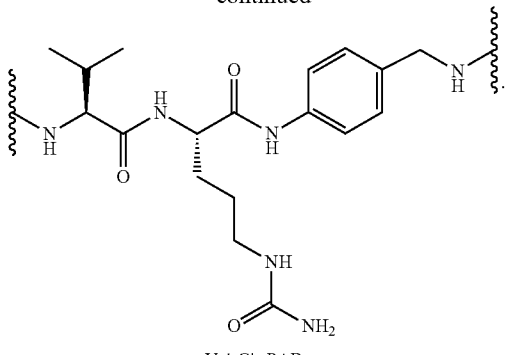

Val-Cit-PAB

Accordingly, the conjugates of the invention as disclosed herein can comprise an enzymatically cleavable linker which comprises any one of the dipeptides-PAB moieties Phe-Lys-PAB, Val-LysPAB, Phe-Ala-PAB, Val-Ala-PAB, Phe-Cit-PAB, or Val-Cit-PAB as disclosed above. Preferably, the cleavable linker of the conjugates of the invention comprises the dipeptide-PAB moiety Val-Ala-PAB.

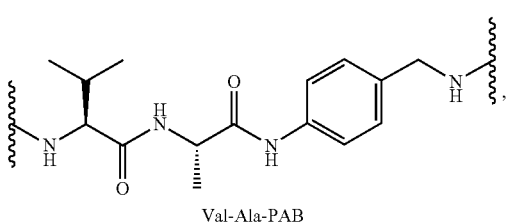 [SMILES: *NCc1ccc(NC(=O)[C@H](C)NC(=O)[C@@H](N*)C(C)C)cc1]

Val-Ala-PAB whereby the PAB moiety is linked to the amatoxin.

According to some embodiments, the linkers of the invention as disclosed above comprise a thiol reactive group, selected from bromo acetamide, iodo acetamide, methyl-sulfonylbenzothiazole, 4,6-dichloro-1,3,5-triazin-2-ylamino group methyl-sulfonyl phenyltetrazole or methyl sulfonyl phenyloxadiazole, pyridine-2-thiol, 5-nitropyridine-2-thiol, methanethiosulfonate, or a maleimide.

According to a preferred embodiment the thiol reactive group is a maleimide (meleimidyl moiety) as depicted below:

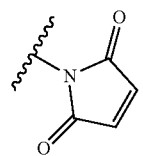 [SMILES: *N1C(=O)C=CC1=O]

According to a particularly preferred embodiment, the linker of the invention comprises the structure

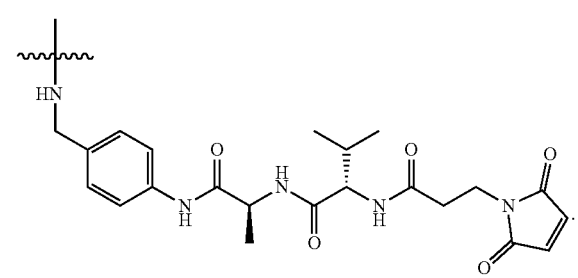 [SMILES: *NCc1ccc(NC(=O)[C@H](C)NC(=O)[C@@H](NC(=O)CCN2C(=O)C=CC2=O)C(C)C)cc1]

In particular embodiments of the present invention, the cleavage site is a disulfide bond and specific cleavage is conducted by a reductive environment, e.g., an intracellular reductive environment, such as, e.g., acidic pH conditions.

According to preferred embodiments of the present invention, in said conjugate as described, said linker, if present, or said target binding moiety is connected to said amatoxin via (i) the γ C-atom of amatoxin amino acid 1, or (ii) the δ C-atom of amatoxin amino acid 3, or (iii) the 6'-C-atom of amatoxin amino acid 4.

In a preferred embodiment of the present invention, said conjugate as described comprises an amatoxin comprising (i) an amino acid 4 with a 6'-deoxy position and (ii) an amino acid 8 with an S-deoxy position.

According to particularly preferred embodiments of the present invention, said conjugate comprises any of the following compounds of formulae (I) to (XI), respectively, as linker-amatoxin moieties:

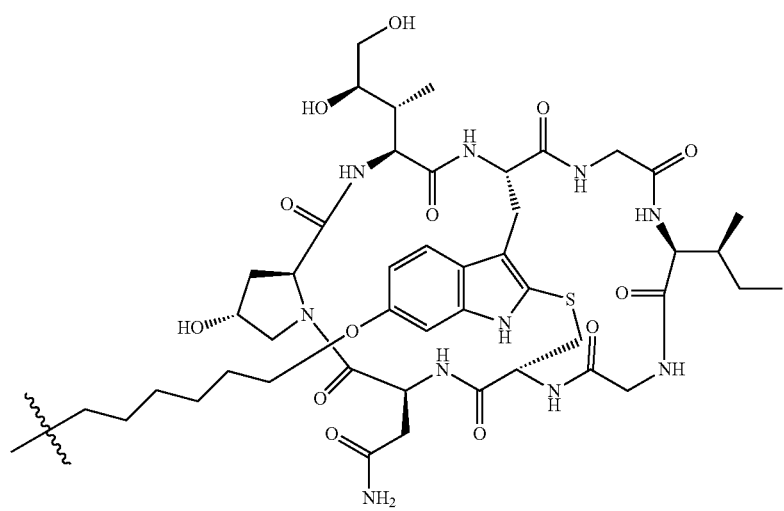

(I)

-continued
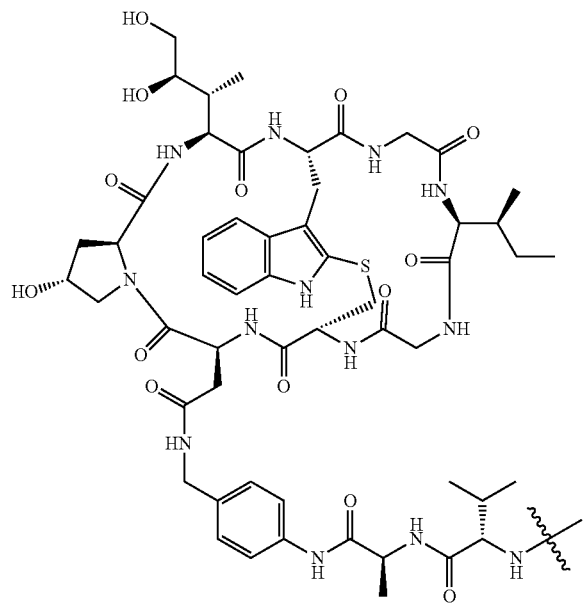
(II)
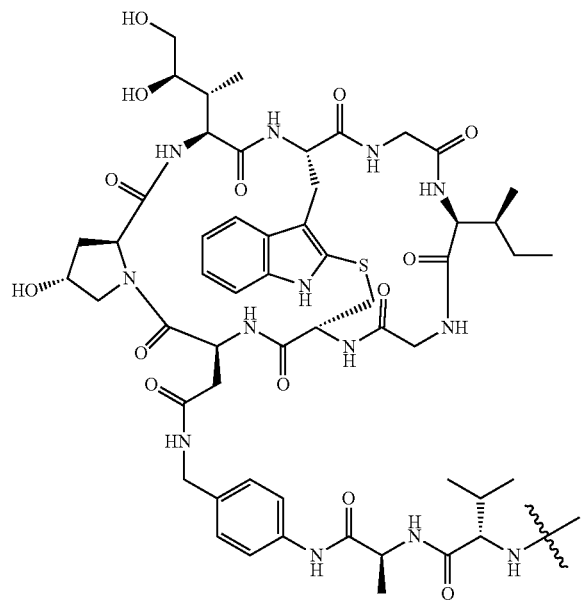
(III)
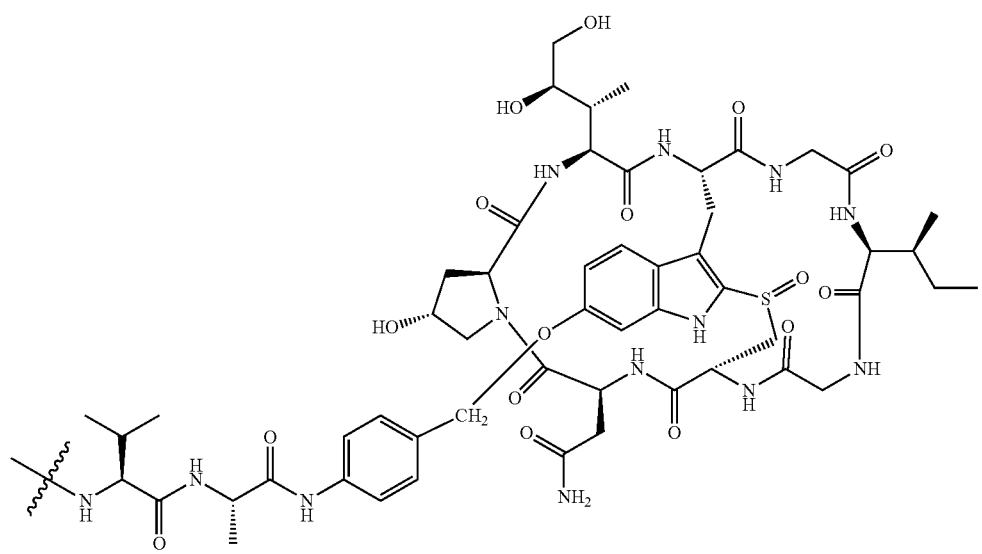
(IV)

-continued
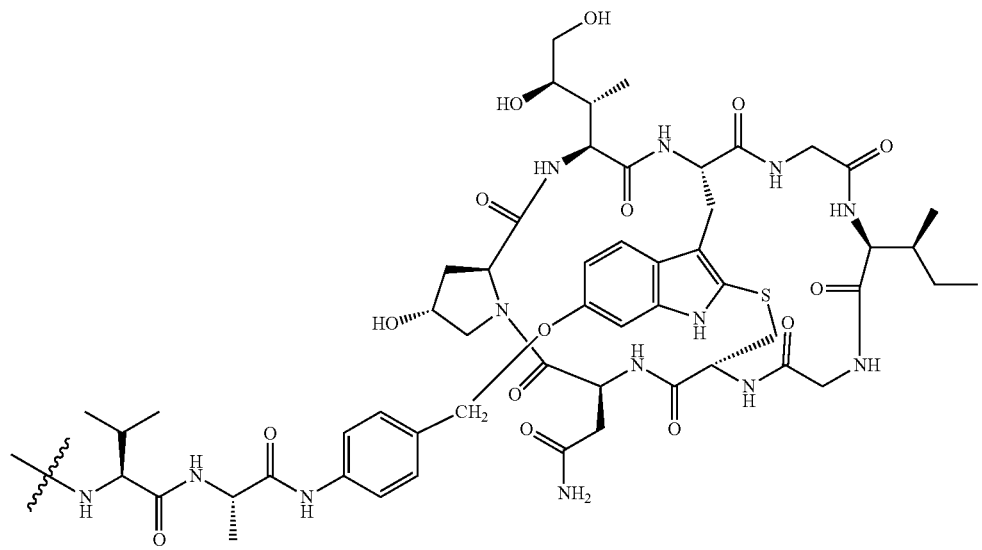
(V)
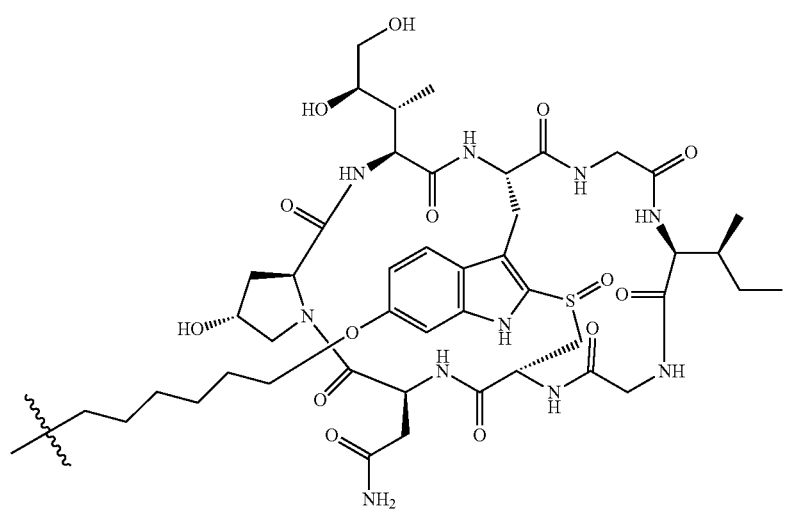
(VI)
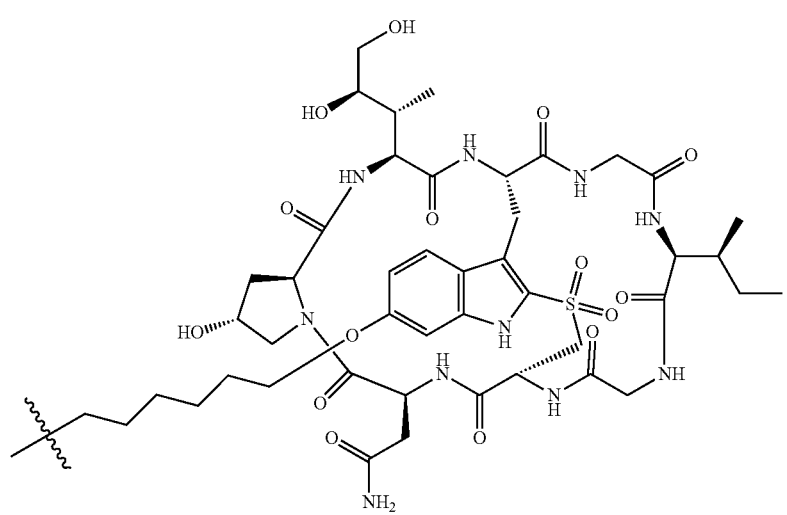
(VII)

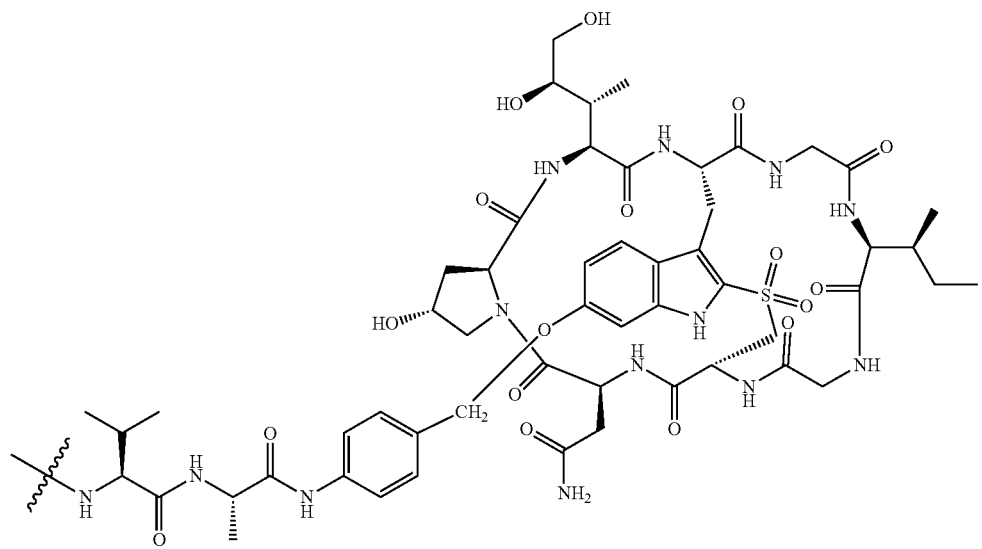
(VIII)
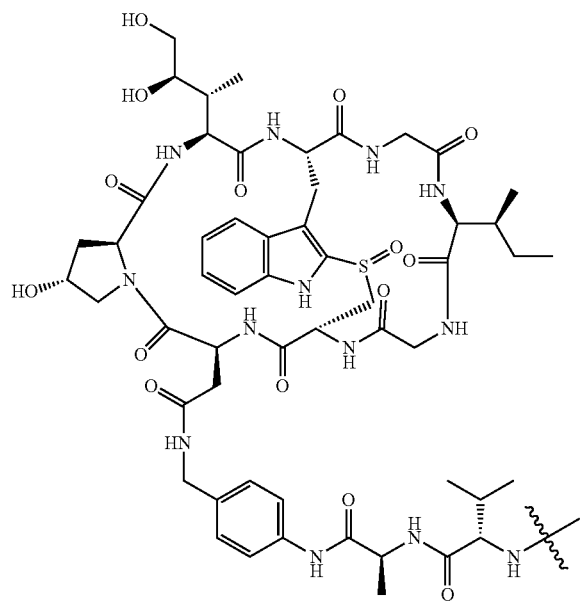
(IX)
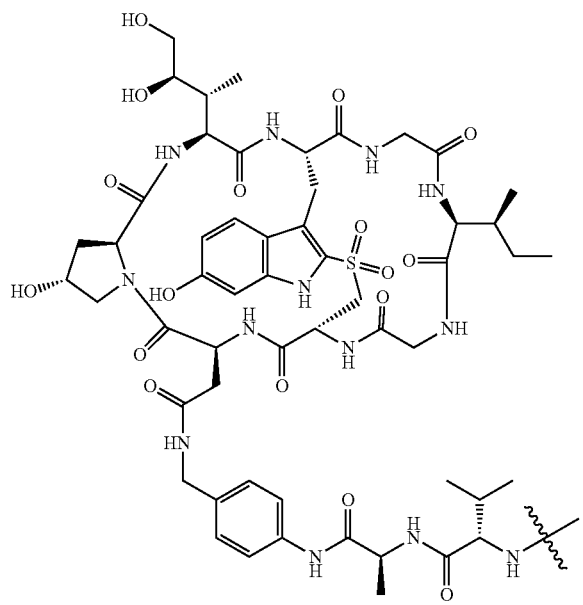
(X)

(XI)
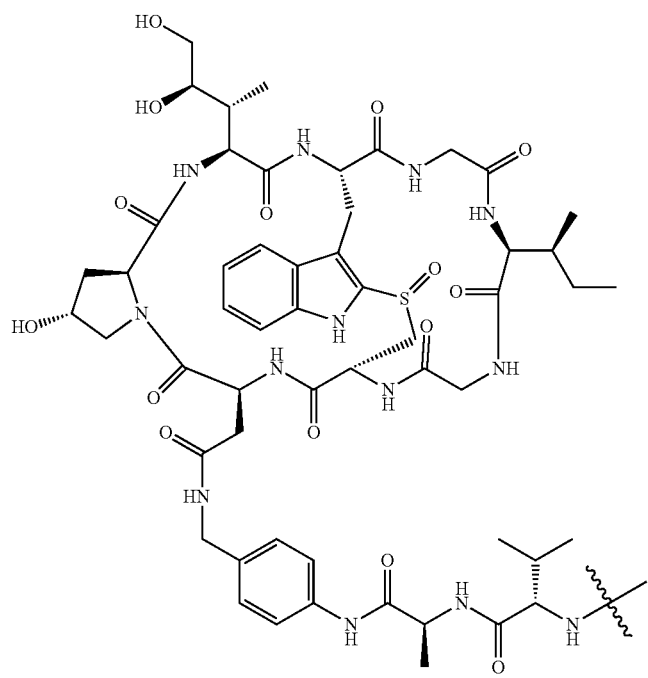
Furthermore, according to particularly preferred embodiments of the present invention, said conjugate comprises an antibody as target binding moiety conjugated to at least one amatoxin linker moiety according to any one of formulae (XII) to (XXII):
(XII)
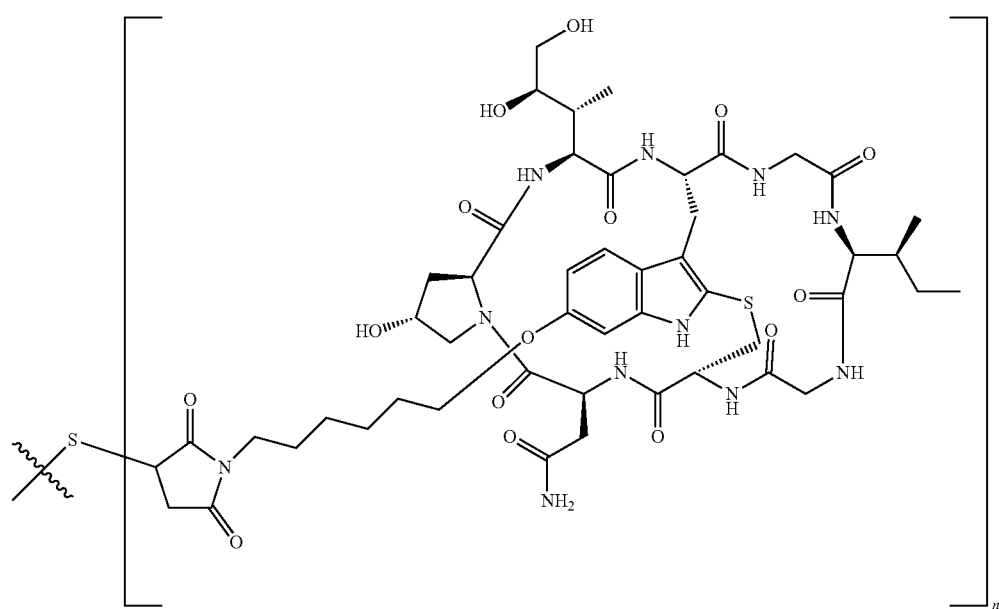

-continued
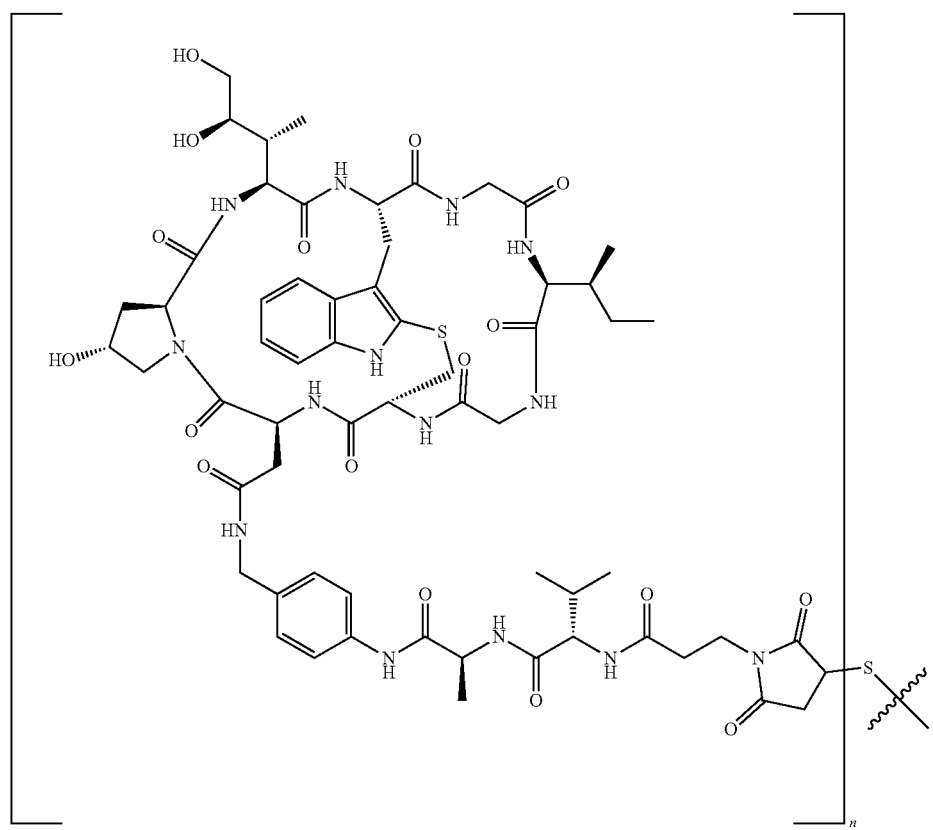
(XIII)
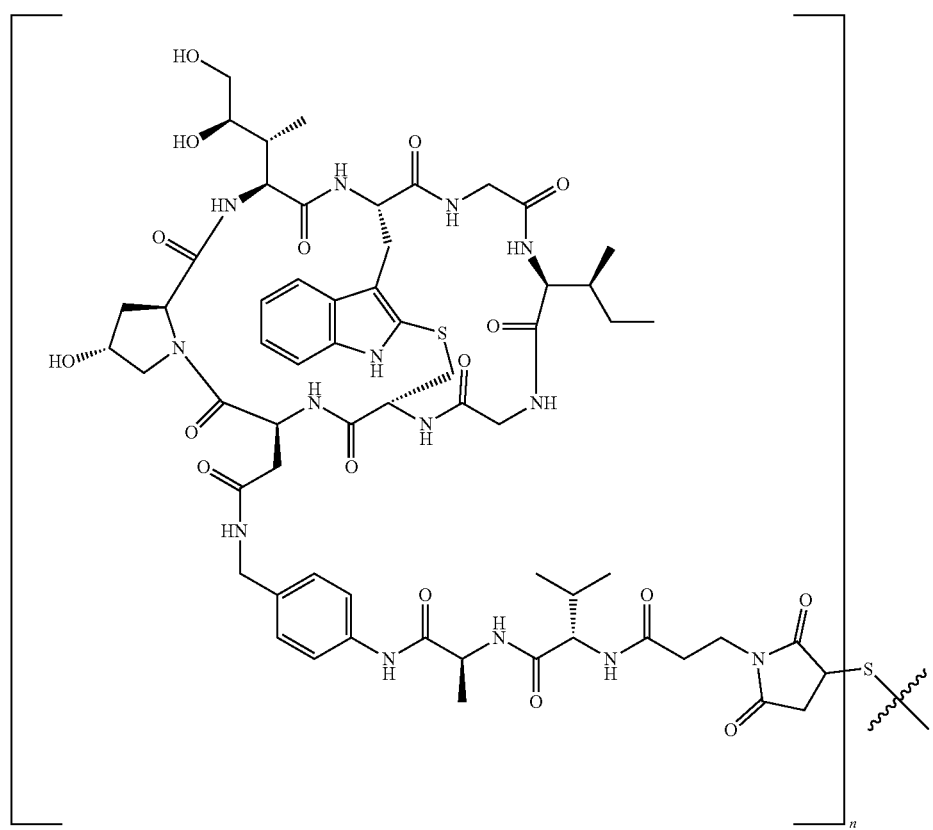
(XIV)

-continued
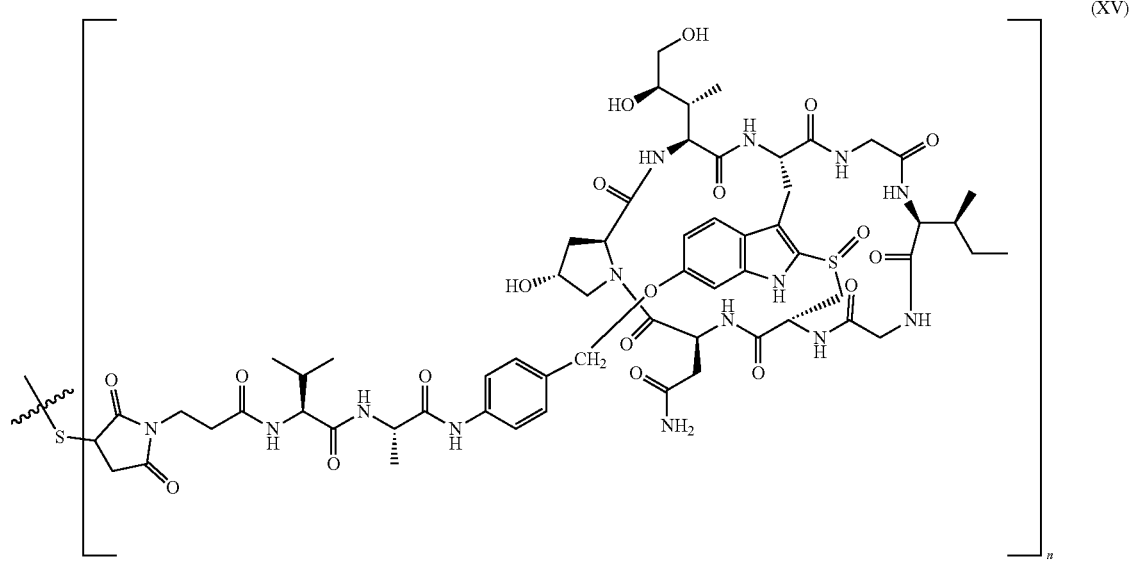
(XV)
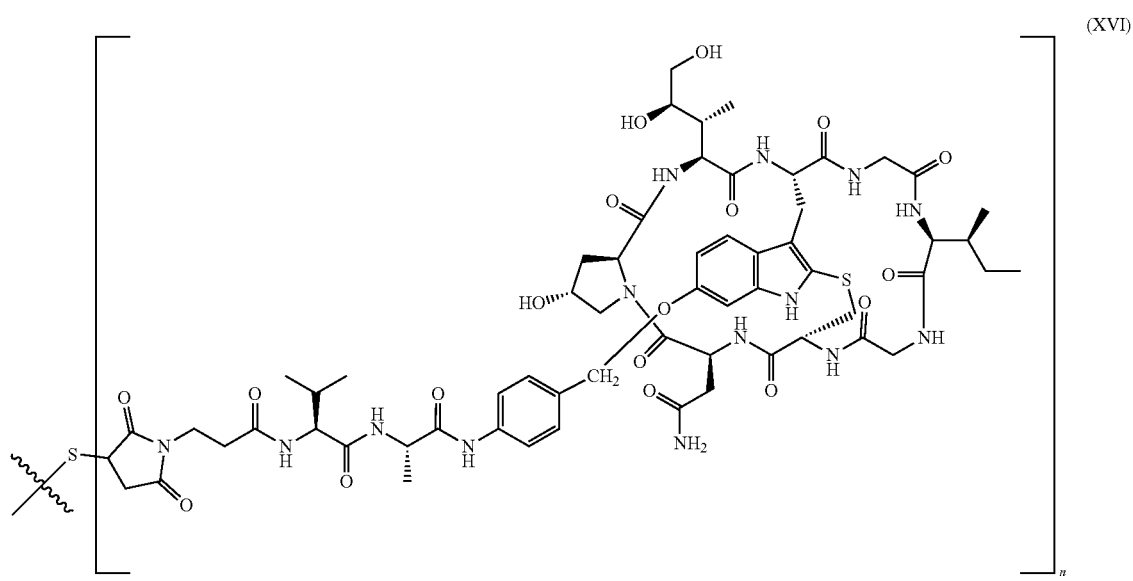
(XVI)

-continued
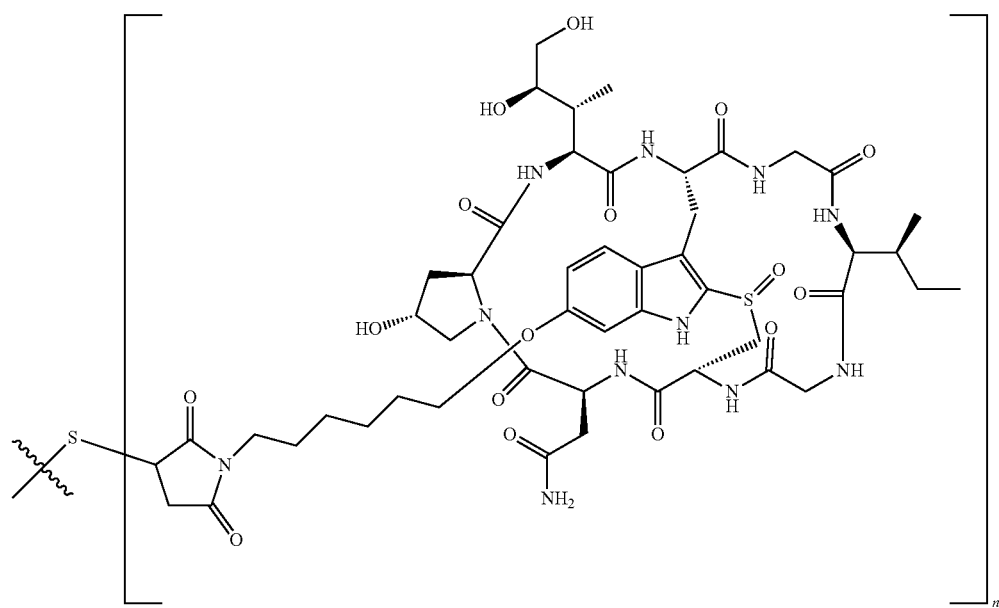
(XVII)
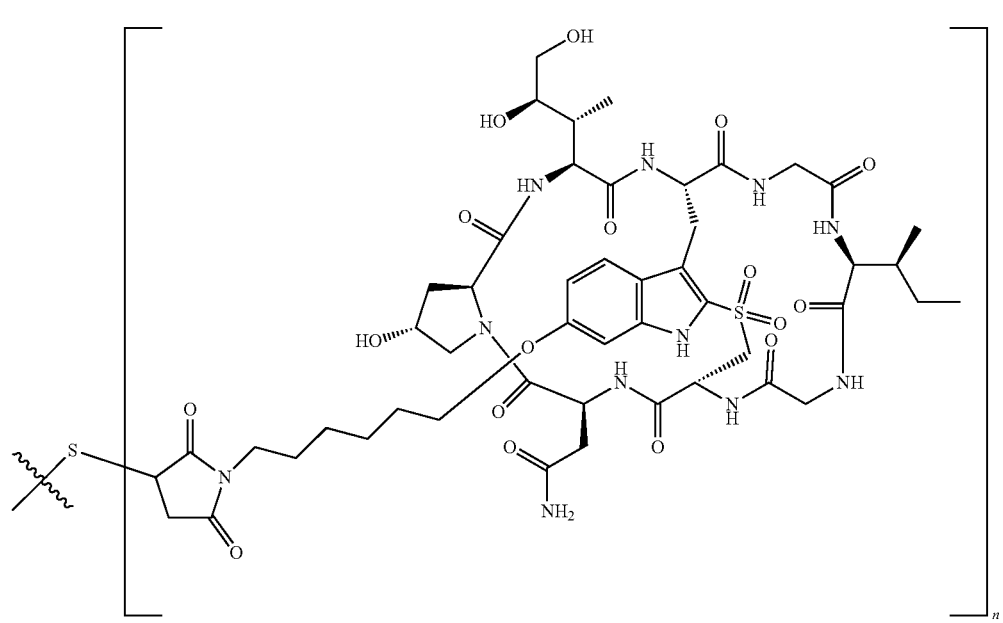
(XVIII)

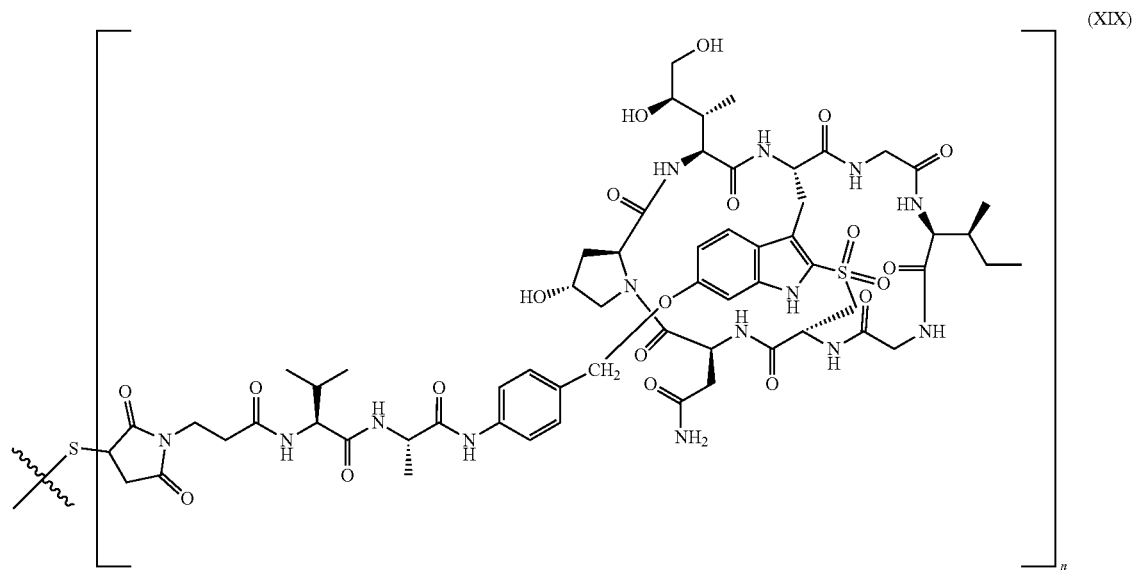
(XIX)
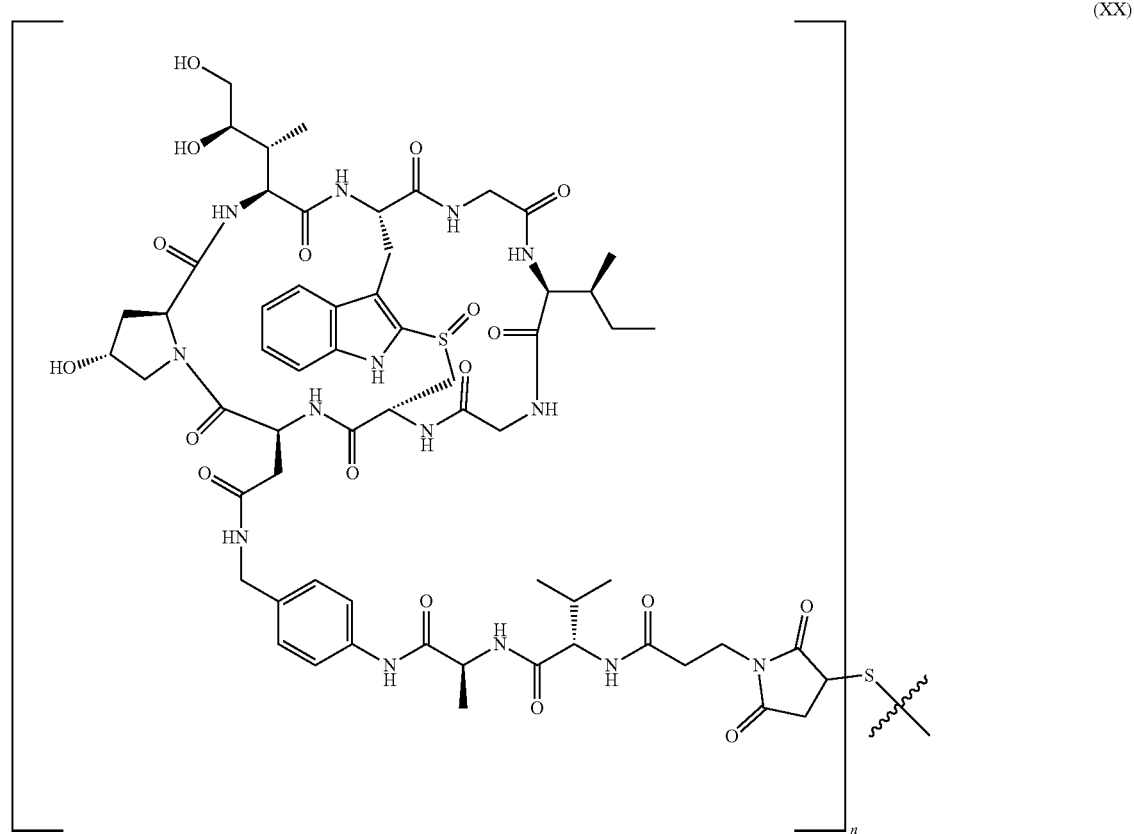
(XX)

-continued
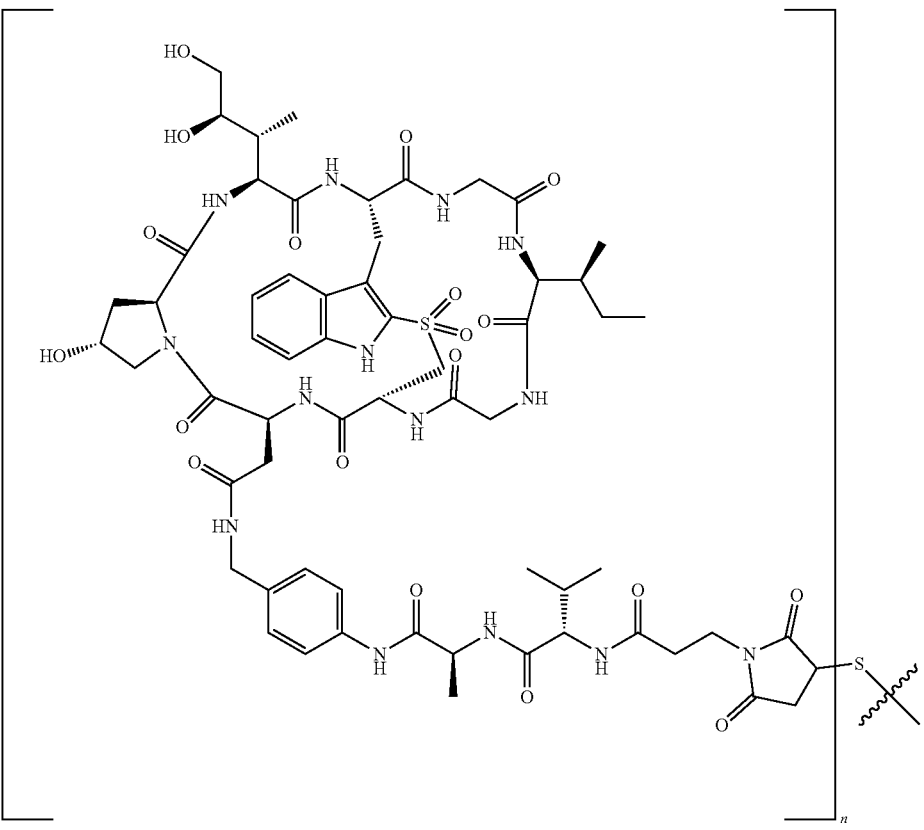
(XXI)
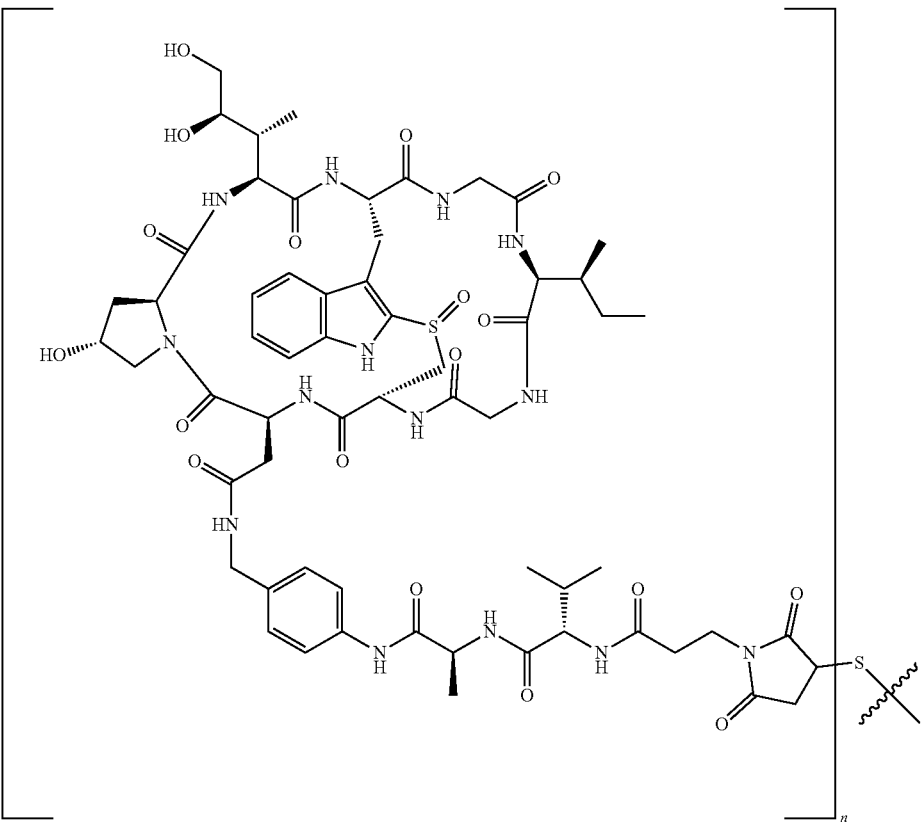
(XXII), wherein said amatoxin linker moieties are coupled via a thioether to the thiol groups of cysteine residues of the antibody, and wherein n is preferably from 1 to 7, e.g. 1, 2, 3, 4, 5, 6, or 7, preferably wherein n is 1, 2, or 4, whereby n indicates the number of amatoxin-linker moieties linked to said antibody. The conjugation of the corresponding amatoxin linker moieties comprising a reactive maleimidyl-residue to a sulfhydryl group of a cysteine residue of an antibody may e.g. be done according to the method as described in Juntula et al. Nat Biotechnol. 2008 August; 26(8):925-32.

According to most particularly preferred embodiments of the present invention, said conjugate is selected from the group consisting of:

(i) conjugate (XXIII) consisting of an antibody consisting of two heavy chains, each heavy chain consisting of or comprising an amino acid sequence according to SEQ ID No. 11, and two light chains, each light chain consisting or comprising an amino acid sequence according to SEQ ID No. 12, as target binding moiety, conjugated to at least one amatoxin-linker moiety of formula (XII) via thioether linkage of the linker with the sulfhydryl group of heavy chain 265Cys residue according to the EU numbering system of said antibody, (ii) conjugate (XXIV) consisting of an antibody consisting of two heavy chains, each heavy chain having an amino acid sequence according to SEQ ID No. 11, and two light chains, each light chain having an amino acid sequence according to SEQ ID No. 12 as target binding moiety, conjugated to at least one amatoxin-linker moiety of formula (XIII) via thioether linkage of the linker with the sulfhydryl group of heavy chain 265Cys residue according to the EU numbering system of said antibody, (iii) conjugate (XXV) consisting of an antibody consisting of two heavy chains, each heavy chain having an amino acid sequence according to SEQ ID No. 11, and two light chains, each light chain having an amino acid sequence according to SEQ ID No. 12 as target binding moiety, conjugated to at least one amatoxin-linker moiety of formula (XIV) via thioether linkage of the linker with the sulfhydryl group of heavy chain 265Cys residue according to the EU numbering system of said antibody, (iv) conjugate (XXVI) consisting of an antibody consisting of two heavy chains, each heavy chain having an amino acid sequence according to SEQ ID No. 11, and two light chains, each light chain having an amino acid sequence according to SEQ ID No. 12 as target binding moiety, conjugated to at least one amatoxin-linker moiety of formula (XV) via thioether linkage of the linker with the sulfhydryl group of heavy chain 265Cys residue according to the EU numbering system of said antibody, (v) conjugate (XXVII) consisting of an antibody consisting of two heavy chains, each heavy chain having an amino acid sequence according to SEQ ID No. 11, and two light chains, each light chain having an amino acid sequence according to SEQ ID No. 12 as target binding moiety, conjugated to at least one amatoxin-linker moiety of formula (XVI) via thioether linkage of the linker with the sulfhydryl group of heavy chain 265Cys residue according to the EU numbering system of said antibody, (vi) conjugate (XXVIII) consisting of an antibody consisting of two heavy chains, each heavy chain having an amino acid sequence according to SEQ ID No. 11, and two light chains, each light chain having an amino acid sequence according to SEQ ID No. 12 as target binding moiety, conjugated to at least one amatoxin-linker moiety of formula (XVII) via thioether linkage of the linker with the sulfhydryl group of heavy chain 265Cys residue according to the EU numbering system of said antibody, (vii) conjugate (XXIX) consisting of an antibody consisting of two heavy chains, each heavy chain having an amino acid sequence according to SEQ ID No. 11, and two light chains, each light chain having an amino acid sequence according to SEQ ID No. 12 as target binding moiety, conjugated to at least one amatoxin-linker moiety of formula (XVIII) via thioether linkage of the linker with the sulfhydryl group of heavy chain 265Cys residue according to the EU numbering system of said antibody, (viii) a conjugate (XXX) consisting of an antibody consisting of two heavy chains, each heavy chain having an amino acid sequence according to SEQ ID No. 11, and two light chains, each light chain having an amino acid sequence according to SEQ ID No. 12 as target binding moiety, conjugated to at least one amatoxin-linker moiety of formula (XIX) via thioether linkage of the linker with the sulfhydryl group of heavy chain 265Cys residue according to the EU numbering system of said antibody, (ix) conjugate (XXXI) consisting of an antibody consisting of two heavy chains, each heavy chain having an amino acid sequence according to SEQ ID No. 11, and two light chains, each light chain having an amino acid sequence according to SEQ ID No. 12 as target binding moiety, conjugated to at least one amatoxin-linker moiety of formula (XX) via thioether linkage of the linker with the sulfhydryl group of heavy chain 265Cys residue according to the EU numbering system of said antibody, (x) conjugate (XXXII) consisting of an antibody consisting of two heavy chains, each heavy chain having an amino acid sequence according to SEQ ID No. 11, and two light chains, each light chain having an amino acid sequence according to SEQ ID No. 12 as target binding moiety, conjugated to at least one amatoxin-linker moiety of formula (XXI) via thioether linkage of the linker with the sulfhydryl group of heavy chain 265Cys residue according to the EU numbering system of said antibody, (xi) conjugate (XXXIII) consisting of an antibody consisting of two heavy chains, each heavy chain having an amino acid sequence according to SEQ ID No. 11, and two light chains, each light chain having an amino acid sequence according to SEQ ID No. 12 as target binding moiety, conjugated to at least one amatoxin-linker moiety of formula (XXII) via thioether linkage of the linker with the sulfhydryl group of heavy chain 265Cys residue according to the EU numbering system of said antibody, wherein n is 1 to 2 for conjugates (XXIII) to (XXXIII). For example, the conjugates (XXIII)-(XXXIII) may comprise one (n=1), or two (n=2) of any one of amatoxin-linker moieties (XII)-(XXII) as disclosed herein linked via a thioether linkage to the sulfhydryl group of heavy chain 265Cys residue. Accordingly, a conjugate of the invention as disclosed above may have a drug-to-antibody ratio (DAR) of DAR=1 for n=1, or a DAR=2 for n=2.

According to one embodiment, the present invention provides an antibody for use in the manufacture of an antibody-drug-conjugate, wherein the antibody comprises two heavy chains, each heavy chain consisting or comprising an amino acid sequence which corresponds to SEQ ID NO: 7 or which is at least 90%, 95% similar thereto, and comprises two light chains each light chain consisting or comprising an amino acid sequence which corresponds to SEQ ID NO: 8 or which is at least 90%, 95% similar thereto.

According to a preferred embodiment, the antibody for use in the manufacture of an antibody-drug-conjugate according to the invention as disclosed above comprises two heavy chains, each heavy chain consisting or comprising preferably an amino acid sequence according to SEQ ID NO. 9, more preferably an amino acid sequence according to SEQ ID NO. 10, or SEQ ID NO: 11, and two light chains, each light chain consisting of or comprising an amino acid sequence according to SEQ ID No. 12.

The use of the inventive antibody in the manufacture of an antibody-drug-conjugate, such as those e.g. as disclosed herein, is particularly advantageous to achieve a site specific conjugation of the linker-toxin conjugate, such as the linker-amatoxin conjugates disclosed herein, via the malimide-sulfhydryl linkage to Cys265 of the antibody to achieve site-specific antibody-drug conjugates at high yield and purity. In addition, the amino acid substitutions L234A, L235A decrease the binding of the antibody of the invention to FcγRI, II, II thereby reducing the effector functions said antibody which are antibody-dependent cellular cytotoxicity (ADCC) and antibody-dependent cellular phagocytosis (ADCP), as well as Complement-Dependent Cytotoxicity (CDC)). Both, higher purity and/or homogeneity of the resulting conjugates, e.g. conjugates with a controlled of about DAR=1, or of about DAR=2 and the reduction in effector function result in a greater therapeutic index (TI) of antibody-drug-conjugates of the invention. The term "therapeutic index" as used herein refers to the ratio of toxic dose at which 50% of the individuals show toxic effects of a drug to the minimal concentration or amount of a drug at which 50% of the individuals show therapeutic effect. The TI may e.g. also be expressed as TI=TD50:ED50 and is a quantitative measurement of the relative safety of a drug. It is a comparison of the amount of a therapeutic agent that causes the therapeutic effect to the amount that causes toxicity. Accordingly, a greater TI corresponds to an increased relative safety of a given drug.

According to another aspect, the present invention provides a pharmaceutical composition comprising said conjugate as described above.

Said pharmaceutical composition may further comprise one or more pharmaceutically acceptable buffers, surfactants, diluents, carriers, excipients, fillers, binders, lubricants, glidants, disintegrants, adsorbents, and/or preservatives.

In aqueous form, said pharmaceutical formulation may be ready for administration, while in lyophilised form said formulation can be transferred into liquid form prior to administration, e.g., by addition of water for injection which may or may not comprise a preservative such as for example, but not limited to, benzyl alcohol, antioxidants like vitamin A, vitamin E, vitamin C, retinyl palmitate, and selenium, the amino acids cysteine and methionine, citric acid and sodium citrate, synthetic preservatives like the parabens methyl paraben and propyl paraben.

Said pharmaceutical formulation may further comprise one or more stabilizer, which may be, e.g., an amino acid, a sugar polyol, a disaccharide and/or a polysaccharide. Said pharmaceutical formulation may further comprise one or more surfactant, one or more isotonizing agents, and/or one or more metal ion chelator, and/or one or more preservative.

The pharmaceutical formulation as described herein can be suitable for at least intravenous, intramuscular or subcutaneous administration. Alternatively, said conjugate according to the present invention may be provided in a depot formulation which allows the sustained release of the biologically active agent over a certain period of time.

In still another aspect of the present invention, a primary packaging, such as a prefilled syringe or pen, a vial, or an infusion bag is provided, which comprises said formulation according to the previous aspect of the invention.

The prefilled syringe or pen may contain the formulation either in lyophilised form (which has then to be solubilised, e.g., with water for injection, prior to administration), or in aqueous form. Said syringe or pen is often a disposable article for single use only, and may have a volume between 0.1 and 20 ml. However, the syringe or pen may also be a multi-use or multi-dose syringe or pen.

Said vial may also contain the formulation in lyophilised form or in aqueous form and may serve as a single or multiple use device. As a multiple use device, said vial can have a bigger volume.

The pharmaceutical composition according to the invention as disclosed herein may e.g. be provided for administration via an infusion bag. Infusion bags typically usually contains the formulation in aqueous form and may have a volume between 20 ml, 50 ml, 75 ml, 100 ml and 125 ml, 250 ml, 300 ml, 500 ml, 750 ml, 1000 ml, 2500 ml, 5000 ml, or between 125 ml, 250 ml and 500 ml, 600 ml, 750 ml According to another aspect of the present invention, the present invention relates to said conjugate or pharmaceutical composition as disclosed herein for use in the treatment of B lymphocyte-associated malignancies or B cell-mediated autoimmune diseases, in particular for use in the treatment of non-Hodgkin's lymphoma (NHL), follicular lymphoma, diffuse large B cell non-Hodgkin's lymphoma (DBNHL), subtypes of non-Hodgkin's lymphoma including mantle cell lymphoma (MCL), chronic lymphocytic leukaemia (CLL), Richter syndrome, primary cutaneous marginal zone lymphoma (PCMZL), hairy cell leukemia, acute myeloid leukemia (AML), rheumatoid arthritis, granulomatosis with polyangiitis and microscopic polyangiitis and pemphigus vulgaris.

According to one embodiment, the B lymphocyte-associated malignancies or B cell-mediated autoimmune diseases as disclosed herein are characterized by a deletion of chromosome 17 p13.1, whereby the deletion is hemizygous or homozygous (nullizygous).

Accordingly, the B-cells of the B lymphocyte-associated malignancies or B cell-mediated autoimmune diseases as disclosed herein to be treated with the conjugate or pharmaceutical composition of the invention as disclosed herein are characterized by a deletion of chromosome 17 p13.1, whereby the deletion is hemizygous or homozygous. The term "deletion" as used herein refers to a loss of the entire genomic locus of chromosome 17p13.1, or a loss of at least 1, 2, 3, 4, 5, 6, 7 Mb encompassing the TP53 gene and the POLR2A gene. Said B lymphocyte-associated malignancies or B cell-mediated autoimmune diseases may e.g. harbor additional cytogenetic abnormalities, such as translocations such as t(11; 14), t(4; 14), t(14; 16) or t(14; 20).

Standard of care treatment options for multiple myeloma may e.g. include those as described in Rajkumar and Kumar Blood Cancer Journal (2020) 10:94.

According to one embodiment, the B-cells of the B lymphocyte-associated malignancies or B cell-mediated autoimmune diseases as disclosed herein which may e.g. be treated with the conjugate or pharmaceutical composition of the invention as disclosed herein, are characterized by a hemizygous loss of the POLR2A gene, or of the TP53 and POLR2A genes. The term "hemizygous" as used according to the invention refers to an individual or cell which has only one full allele of a gene or chromosome segment rather than the usual two. A hemizygote refers to a cell or organism whose genome includes only one full allele at a given locus, whether the allele is wildtype or mutant, e.g. the cells of the B lymphocyte-associated malignancies or B cell-mediated autoimmune diseases as disclosed herein are hemizygotes for chromosome locus 17p13, preferably the cells of the B lymphocyte-associated malignancies or B cell-mediated autoimmune diseases as disclosed above are hemizygotes for the genes TP53 and POLR2A. "TP53" as used herein refers "tumor protein 53" gene which encodes a tumor suppressor protein (P53) which comprises transcriptional activation, DNA binding, and oligomerization domains. The encoded protein responds to diverse cellular stresses to regulate expression of target genes, thereby inducing cell cycle arrest, apoptosis, senescence, DNA repair, or changes in metabolism. Mutations in this gene are associated with a variety of human cancers, including hereditary cancers such as Li-Fraumeni syndrome.

The tumour suppressor gene TP53 is frequently inactivated by mutation or deletion in a majority of human tumors. "POLR2A" as used herein refers to the POLR2A gene which encodes the largest subunit of the human RNA polymerase II complex and which is indispensable for the polymerase activity in mRNA synthesis. Hemizygous loss of chromosome 17p13, e.g. del(17p13.1), may be detected by fluorescence in situ hybridization (FISH) as disclosed in Merz et al. Am J Hematol. 2016 November; 91(11):E473-E477.

The cells of the B lymphocyte-associated malignancies or B cell-mediated autoimmune diseases as disclosed above may e.g. not be a homogenous group of cells with regard to the loss of TP53 and/or POLR2A. For example, from about 5%, 7.5%, 10%, 15%, 20%, 25%, 30%, 40% 50%, 60% to about 70%, 75%, 80%, 85%, 90%, 95%, 100, or from about 70%, 75%, 80, 85% to about 90%, 92.5%, 95%, 97.5%, 100% of the cells of the B lymphocyte-associated malignancies or B cell-mediated autoimmune diseases as disclosed above may be hemizygous for the del(17p13.1), TP53 and/or POLR2A, or e.g. at least 5%, 10%, 15%, 20%, 25%, 30%, 40%, 45%, 50%, 60%, 70%, 75%, 80%, 90%, 95% of the cells of the B lymphocyte-associated malignancies or B cell-mediated autoimmune diseases as disclosed herein are hemizygous for del(17p13), or for TP53 and/or POLR2A. The conjugate or pharmaceutical composition of the invention for use in the treatment of B lymphocyte-associated malignancies which are characterized by a hemizygous loss of chromosome 17p13.1, or TP53 and/or POLR2A is particularly advantageous, since cells characterized by a hemizygous loss of chromosome 17p13.1, TP53 and/or POLR2A are at least 10-fold, 25-fold, 50-fold, 100-fold, 250-fold, 500-fold 1000-fold more sensitive to the conjugate or pharmaceutical composition of the invention as disclosed herein. Accordingly, it may e.g. be beneficial to determine whether the B lymphocyte-associated malignancies or B cell-mediated autoimmune diseases as disclosed herein comprise or consist of cells which are hemizygous for the loss of TP53 and/or POLR2A, since at least 10-fold, 25-fold, 50-fold, 100-fold, 250-fold, 500-fold or 1000-fold less of the conjugate or pharmaceutical composition of the invention as disclosed herein may be used to achieve the desired therapeutic effect. Assays to assess the sensitivity to the conjugate or pharmaceutical composition of the invention as disclosed herein can e.g. be done as described in Nature. 2015 Apr. 30; 520(7549): 697-701.

According to one aspect the invention the conjugate or pharmaceutical composition as disclosed herein is used in combination with immune checkpoint inhibitors in the treatment of B lymphocyte-associated malignancies or B cell-mediated autoimmune diseases as disclosed above. In the context of the present invention, the term "immune checkpoint inhibitor" or simply "checkpoint inhibitor" or "ICI" refers to any agent or compound that, either directly or indirectly, decreases the level of or inhibits the function of an immune checkpoint receptor protein or molecule found on the surface of an immune cell (for example, a T cell), or to any agent or compound that, either directly or indirectly, decreases the level of or inhibits the function of a ligand that binds to said immune checkpoint receptor protein or molecule, either as a soluble compound or on the surface of an immune cell-inhibitory cell. Such an inhibitory cell can be, for example, a cancer cell, a regulatory T cell, a tolerogenic antigen presenting cell, a myeloid-derived suppressor cells, a tumor-associated macrophage, or a cancer-associated fibroblast. Said ligand is typically capable of binding the immune checkpoint receptor protein or molecule on the immune cell. A non-limiting example of an immune checkpoint receptor protein-ligand pair is PD-1, PD-L1. PD-1 is an immune checkpoint receptor protein found on T-cells. PD-L1, which can be over-expressed by cancer cells, binds to PD-1 and helps the cancer cells to evade the host immune system attack. Accordingly, an immune checkpoint inhibitor prevents the PD-1/PD-L1 interaction by either blocking the PD-1 on the T cell (i.e. acts as a PD-I inhibitor) or the PD-L1 on the cancer cell (i.e., acts as a PD-L1 inhibitor), thereby maintaining or restoring anti-tumor T-cell activity or blocking inhibitory cancer cell activity.

Immune checkpoint receptors or molecules include, without limitation, e.g., PD-1, CTLA-4, LAG-3, TIM-3, TIGIT, VISTA, OX40, GITR, ICOS, CD276 (B7-H3), B7-H4 (VTCN1), IDO, KIR, CD122, CD137, CD94/NKG2A, CD80, CD86, Galectin-3, LSECtin, CD112, Ceacam-1, Gal-9, PtdSer, HMGB1, HVEM, CD155 and BTLA (CD272).

Immune checkpoint inhibitors comprise antagonists of an immune inhibitory receptor, such as those disclosed above, e.g. PD-1, which inhibit, in this case, the PD-1 or PD-L1 in the PD-1/PD-L1 pathway. Examples of PD-1 or PD-L1 inhibitors include, without limitation, humanized or human antibodies antagonizing or blocking human PD-1 function such as pembrolizumab, pidilizumab, cemiplimab, JTX-4014, spartalizumab, sintilimab (IBI308), dostarlimab (TSR-042, WBP-285), INCMGA00012 (MGA012), AMP-224, PD1-1, PD1-2, PD1-3, PD1-4, PD1-5, BCD-100, AGEN-2034, Toripalimab (TAB001, JS001), or AMP-514 (MEDI0680), as well as fully human antibodies such as the PD-1 blocking nivolumab or blocking PD-L1 such as avelumab, durvalumab, Cosibelimab (CK-301), WBP-3155 (CS1001) and atezolizumab or the recombinant anti-PD-L1 probody CX-072.

Pembrolizumab (formerly also known as lambrolizumab; trade name Keytruda; also known as MK-3475) disclosed e.g. in Hamid, O. et al. (2013) New England Journal of Medicine 369(2):134-44, is a humanized IgG4 monoclonal antibody that binds to PD-1; it contains a mutation at C228P designed to prevent Fc-mediated cytotoxicity. Pembrolizumab is e.g. disclosed in U.S. Pat. No. 8,354,509 and WO2009/114335. It is approved by the FDA for the treatment of patients suffering from unresectable or metastatic melanoma and patients with metastatic NSCLC.

Nivolumab (CAS Registry Number: 946414-94-4; BMS-936558 or MDX1106b) is a fully human IgG4 monoclonal antibody which specifically blocks PD-1, lacking detectable antibody-dependent cellular toxicity (ADCC). Nivolumab is e.g. disclosed in U.S. Pat. No. 8,008,449 and WO2006/121168. It has been approved by the FDA for the treatment of patients suffering from unresectable or metastatic melanoma, metastatic NSCLC and advanced renal cell carcinoma.

Pidilizumab (CT-011; Cure Tech) is a humanized IgG1k monoclonal antibody that binds to PD-1. Pidilizumab is e.g. disclosed in WO2009/101611.

PD1-1 to PD1-5 refer to anti-PD-1 antibodies as disclosed in WO2018/220169.

The INNs as used herein are meant to also encompass all biosimilar antibodies of the corresponding originator antibody as disclosed herein, including but not limited to those biosimilar antibodies authorized under 42 USC § 262 subsection (k) in the US and equivalent regulations in other jurisdictions.

Immune checkpoint inhibitors for use according to the invention in combination with the conjugate or pharmaceutical composition of the invention as disclosed herein may e.g. also be a small molecule (organic) compound or a large molecule such as a peptide or a nucleic acid. For example, small molecule immune checkpoint inhibitors according to the invention include CA-170, including its precursor AUNP-12, as disclosed in WO15033301 A1; or e.g. BMS-8 (CAS number 1675201-90-7). In at least one embodiment of the present invention, an immune checkpoint inhibitor is an antibody, or an antigen binding fragment thereof, or an antigen binding derivative thereof. In a preferred embodiment, the immune checkpoint inhibitor is a monoclonal antibody, or an antigen binding fragment thereof, or an antigen binding derivative thereof.

In some embodiments of the invention, the conjugate or pharmaceutical composition of the invention for use in the treatment of B lymphocyte-associated malignancies or B cell-mediated autoimmune diseases as disclosed herein may be combined with or comprise two immune checkpoint inhibitors as disclosed herein. For example, it is preferred that the conjugate or pharmaceutical composition as disclosed herein is combined with or comprises two or more immune checkpoint inhibitors that target different immune checkpoints, e.g. CTLA-4 and PD-1/PD-L1, PD-1/PD-L1 and TIGIT, PD-1/PD-L1 and OX40, PD-1/PD-L1 and VISTA, CTLA4 and TIGIT, CTLA4 and OX40. Accordingly, the conjugate or pharmaceutical composition according to the invention may e.g. be combined with or comprise one of the following combinations of immune checkpoint inhibitors:

CTLA4-PD-1/PD-L1:

Ipilimumab in combination with one of nivolumab, avelumab, pembrolizumab, pidilizumab, PD1-1, PD1-2, PD1-3, PD1-4, PD1-5, durvalumab, atezolizumab PD-1/PD-L1 and TIGIT:

Tiragolumab in combination with one of nivolumab, avelumab, pembrolizumab, pidilizumab, PD1-1, PD1-2, PD1-3, PD1-4, PD1-5, durvalumab, atezolizumab; or BMS986207 in combination with one of nivolumab, avelumab, pembrolizumab, pidilizumab, PD1-1, PD1-2, PD1-3, PD1-4, PD1-5, durvalumab, atezolizumab;

PD-1/PD-L1 and OX40:

BMS986178 in combination with one of nivolumab, avelumab, pembrolizumab, pidilizumab, PD1-1, PD1-2, PD1-3, PD1-4, PD1-5, durvalumab, atezolizumab PD-1/PD-L1 and VISTA CI-8993 in combination with one of nivolumab, avelumab, pembrolizumab, pidilizumab, PD1-1, PD1-2, PD1-3, PD1-4, PD1-5, durvalumab, atezolizumab OX40 and PD-1/PD-L1:

MEDI0562 in combination with one of nivolumab, avelumab, pembrolizumab, pidilizumab, PD1-1, PD1-2, PD1-3, PD1-4, PD1-5, durvalumab, atezolizumab, or PF04518600 in combination with one of nivolumab, avelumab, pembrolizumab, pidilizumab, PD1-1, PD1-2, PD1-3, PD1-4, PD1-5, durvalumab, atezolizumab TIM-3 and PD-1/PD-L1:

MBG453 in combination with one of nivolumab, avelumab, pembrolizumab, pidilizumab, PD1-1, PD1-2, PD1-3, PD1-4, PD1-5, durvalumab, atezolizumab CTLA4 and TIGIT:

Ipilimumab in combination with one of tiragolumab, or BMS986207.

CTLA4 and OX40:

Ipilimumab in combination with one of MEDI0562, or PF04518600.

Checkpoint inhibitors selected from the group of PD-1, PD-L1 and CTLA4 inhibitors as disclosed above are preferred immune checkpoint inhibitors if the conjugate or pharmaceutical composition according to the invention is combined with or comprises only one immune checkpoint inhibitor. Accordingly, in one embodiment, the conjugate according to the invention as disclosed herein is preferably combined with one of pembrolizumab, pidilizumab, cemiplimab, JTX-4014, spartalizumab, sintilimab (IBI308), dostarlimab (TSR-042, WBP-285), INCMGA00012 (MGA012), AMP-224, PD1-1, PD1-2, PD1-3, PD1-4, PD1-5, BCD-100, AGEN-2034, Toripalimab (TAB001, JS001), or AMP-514 (MEDI0680), avelumab, durvalumab, Cosibelimab (CK-301), WBP-3155 (CS1001) and atezolizumab, CX-072, ipilimumab for use in the treatment of B lymphocyte-associated malignancies or B cell-mediated autoimmune diseases as disclosed herein.

According to one embodiment, the pharmaceutical composition of the invention is preferably combined with one of pembrolizumab, pidilizumab, cemiplimab, JTX-4014, spartalizumab, sintilimab (IBI308), dostarlimab (TSR-042, WBP-285), INCMGA00012 (MGA012), AMP-224, PD1-1, PD1-2, PD1-3, PD1-4, PD1-5, BCD-100, AGEN-2034, Toripalimab (TAB001, JS001), or AMP-514 (MEDI0680), avelumab, durvalumab, Cosibelimab (CK-301), WBP-3155 (CS1001) and atezolizumab, CX-072, ipilimumab for use in the treatment of B lymphocyte-associated malignancies or B cell-mediated autoimmune diseases as disclosed herein.

According to one embodiment, the pharmaceutical composition of the invention as disclosed herein is combined with pembrolizumab for use in the treatment of diffuse large B-cell lymphoma, follicular lymphoma; primary mediastinal B-cell lymphoma, classical Hodgkin lymphoma; multiple myeloma.

According to one embodiment, the pharmaceutical composition of the invention as disclosed herein is combined with nivolumab for use in the treatment of diffuse large B-cell lymphoma, B-cell non-Hodgkin lymphoma, or follicular lymphoma.

According to one embodiment, the pharmaceutical composition of the invention as disclosed herein is combined with ipilimumab for use in the treatment of diffuse large B-cell lymphoma, follicular lymphoma, or mantle cell lymphoma.

According to one embodiment, the pharmaceutical composition of the invention as disclosed herein is combined with ipilimumab and nivolumab for use in the treatment of classical Hodgkin lymphoma; B-cell non-Hodgkin lymphoma, non-Hodgkin lymphoma; multiple myeloma.

According to one embodiment, the pharmaceutical composition of the invention as disclosed herein is combined with atezolizumab for use in the treatment of diffuse large B-cell lymphoma, follicular lymphoma, mantle cell lymphoma.

According to one embodiment, the pharmaceutical composition of the invention as disclosed herein is combined with avelumab for use in the treatment of diffuse large B-cell lymphoma, follicular lymphoma, mantle cell lymphoma.

According to one embodiment, the pharmaceutical composition of the invention as disclosed herein is combined with durvalumab for use in the treatment of diffuse large B-cell lymphoma, follicular lymphoma, mantle cell lymphoma.

In one embodiment, the present invention pertains to the pharmaceutical compositions of the invention as disclosed herein for use in the treatment of B lymphocyte-associated malignancies or B cell-mediated autoimmune diseases in a patient as disclosed herein, optionally comprising the administration of immune checkpoint inhibitors as disclosed herein, wherein the patients have undergone a prior standard of care treatment with one of the treatment regimens R-CHOP, CHOP, Hyper-CVAD, or CVD.

For example, standard of care treatments may include the standard regimen, R-CHOP (rituximab plus cyclophosphamide, doxorubicin, vincristine, and prednisone) for use in the treatment of diffuse large B cell lymphoma (DLBCL). Standard of care treatment for Mantle cell lymphoma may e.g. include 1) the "Hyper-CVAD" treatment regime comprising cyclophosphamide, vincristine, doxorubicin (Adriamycin), and dexamethasone, alternating with high-dose methotrexate plus cytarabine, or 2) "dose-intensified" R-CHOP (rituximab, cyclophosphamide, doxorubicin, vincristine, and prednisone), alternating with rituximab and cytarabine, or 3) RDHAP (rituximab, dexamethasone, cytarabine, cisplatin). Standard of care for the treatment of follicular lymphoma (FC) can e.g. comprise treatment with rituximab, or obinutuzumab in combination with CHOP (cyclophosphamide, doxorubicin, vincristine, prednisone) or CVP (cyclophosphamide, vincristine, prednisone) regimens.

Standard of care treatment for non-Hodgkin lymphoma can e.g. comprise treatment with rituximab, obinutuzumab, ofatumumab, or ibritumomab tiuxetan alone, or in combination with chemotherapy according to the CHOP treatment regiment cyclophosphamide, doxorubicin, vincristine and prednisone, or CVP (cyclophosphamide, vincristine and prednisone).

The term "combine" or "combination" and any grammatical equivalent thereof as used with the treatment options disclosed herein refers to the serial or concomitant application of the pharmaceutical composition of the invention as disclosed herein and the immune checkpoint inhibitors as disclosed herein. For example, the pharmaceutical composition of the invention as disclosed herein may be administered first, followed by subsequent administration of an immune checkpoint inhibitor as disclosed herein, or the immune checkpoint inhibitor as disclosed herein may be administered first, followed by a subsequent administration of the pharmaceutical composition of the invention. Serial administration of the pharmaceutical composition of the invention and of the immune checkpoint inhibitor as disclosed herein shall refer to an administration regiment of said pharmaceutical composition and said immune checkpoint inhibitor 15 min, 30 min, 45 min, 1 hour, 2 hours, 3 hours, 4 hours, 5 hours, 6 hours, 12 hours, 24 hours, 48 hours, 72 hours apart from each other irrespective of the order which of the two is administered first, said pharmaceutical composition and said immune checkpoint inhibitor can also e.g. be administered within the same treatment regimen or treatment cycle. Concomitant administration shall refer to an administration regiment in which both the pharmaceutical composition of the invention and the immune checkpoint inhibitor both as disclosed herein are administered at the same time, or within 1, 2, 3, 4, 5, 6, 7, 8, 9, 10 minutes apart from each other. All of the aforementioned administration regimens are considered a "combination" according to the invention.

The invention relates to the use of said conjugate or pharmaceutical composition as described above in the manufacture of a medicament for treatment of B lymphocyte-associated malignancies or B cell-mediated autoimmune diseases, in particular for treatment of non-Hodgkin's lymphoma (NHL), follicular lymphoma, diffuse large B cell non-Hodgkin's lymphoma (DBNHL), subtypes of non-Hodgkin's lymphoma including mantle cell lymphoma (MCL), chronic lymphocytic leukaemia (CLL), Richter syndrome, primary cutaneous marginal zone lymphoma (PCMZL), hairy cell leukemia, acute myeloid leukemia (AML), rheumatoid arthritis, granulomatosis with polyangiitis and microscopic polyangiitis and pemphigus vulgaris.

According to one embodiment, the conjugate of the invention or the pharmaceutical composition of the invention as disclosed above may be used in the treatment of Richter Syndrome. Richter syndrome which is defined as the transformation of chronic lymphocytic leukemia (CLL)/small lymphocytic lymphoma into an aggressive lymphoma, most commonly a diffuse large B-cell lymphoma (DLBCL). Occurring in approximately 2%-10% of patients with CLL, Richter syndrome is highly aggressive, often refractory to treatment, with a poor outcome of approximately 8-14 months of survival following diagnosis. Approximately 80% of cases are clonally related to the underlying CLL, while the remaining 20% of patients have a clonally unrelated DLBCL, and have a better prognosis similar to that of de novo DLBCL (Vaisitti et al 2018). A combination of germline genetic characteristics, clinical features, biologic and somatic genetic characteristics of CLL B cells, and certain CLL therapies are associated with higher risk of Richter syndrome.

In one embodiment, the present invention pertains to the pharmaceutical compositions of the invention as disclosed herein for use in the treatment of Richter Syndrome in a patient, optionally comprising the administration of immune checkpoint inhibitors as disclosed herein. For example, the pharmaceutical compositions of the invention as disclosed herein may be optionally combined with immune checkpoint inhibitors that have been used in the treatment of diffuse large B-cell lymphoma (DLBCL) as disclosed herein, e.g. ipilimumab, atezolizumab, avelumab, durvalumab or nivolumab.

In one embodiment, the present invention pertains to the pharmaceutical compositions of the invention as disclosed herein for use in the treatment of Richter Syndrome in a patient, optionally comprising the administration of immune checkpoint inhibitors as disclosed herein, wherein the patient has undergone a prior standard of care treatment with one of the treatment regimens R-CHOP, Hyper-CVXD, a combination of: Rituximab and GM-CSF with alternating hyper CVXD and MTX/cytarabine; or OFAR, or radioimmunotherapy with e.g. $^{90}$Y, ibritumomab, tiuxetan. "Hyper-CVXD" as used herein refers to a treatment regimen comprising fractionated administration of cyclophosphamide, vincristine, liposomal daunorubicin, and dexamethasone. "OFAR" refers to a treatment regime comprising the administration of oxaliplatin, fludarabine, cytarabine and rituximab (e.g. as disclosed in Tsimberidou et al. J Clin Oncol. 2008 Jan. 10; 26(2):196-203).

In one embodiment, the present invention pertains to the pharmaceutical compositions of the invention as disclosed herein for use in the treatment of B lymphocyte-associated malignancies or B cell-mediated autoimmune diseases in a patient as disclosed herein, optionally comprising the administration of immune checkpoint inhibitors as disclosed herein, wherein the B-cells of said B lymphocyte-associated malignancies or B cell-mediated autoimmune diseases express less than 130.000 CD37 epitopes on their cell surface, or from about 32.500, 35.000, 40.000, 45.000, 50.000, 60.000, 75.000, 100.000 to about 110.00, 120.000, 125.000, 130.000, or from about 110.00, 120.000, 125.000 to about 130.000 CD37 epitopes on their cell surface. For example, cell surface expression of CD37 may be done according to methods disclosed in E Cabral Filho et al. Int J Nanomedicine. 2015; 10: 4393-4404, or as disclosed herein using a Quantum™ MESF kit.

In one embodiment, the invention also relates to a method of treating a patient suffering from a B lymphocyte-associated malignancy or B cell-mediated autoimmune disease as disclosed herein, wherein the methods comprises administering a therapeutically effective amount of said conjugate or pharmaceutical composition as described herein to the patient.

In one embodiment, the inventive method of treating a patient suffering from a B lymphocyte-associated malignancy or B cell-mediated autoimmune disease as disclosed herein, further comprises administering a therapeutically effective amount of said conjugate or pharmaceutical composition as described herein to the patient in combination with one or more immune checkpoint inhibitors as disclosed herein. The conjugate or pharmaceutical composition of the invention and the one or more immune checkpoint inhibitors as disclosed herein can be administered sequentially, or concomitantly. For example, the conjugate or pharmaceutical composition as described herein may be adminstered first followed by the administration of the one or more checkpoint inhibitors, or the one or more checkpoint inhibitors may be administered prior to the administration of the conjugate or pharmaceutical composition as described herein. Depending on the one or more immune checkpoint inhibitors used in the method of treatment which are administered to said patient it can be advantageous if said one or more checkpoint inhibitors are administered sequentially.

In one embodiment, the present invention pertains to a method of treating a patient suffering from a B lymphocyte-associated malignancy or B cell-mediated autoimmune disease as disclosed herein, wherein the method comprises administering a therapeutically effective amount of said conjugate or pharmaceutical composition as described herein to the patient optionally in combination with one or more immune checkpoint inhibitors as disclosed herein, wherein the patient has undergone a prior standard of care treatment comprising one of the treatment regiments R-CHOP, CHOP, Hyper-CVAD, or CVD.

In one embodiment, the present invention pertains to a method of treating a patient afflicted with B lymphocyte-associated malignancy or B cell-mediated autoimmune disease as disclosed herein, wherein the method comprises (step 1) producing a conjugate according to any of formulae (II), (III), (IX), (X), (XI) by process A), or producing a conjugate according to any of formulae (I), (IV), (V), (VI), (VII), (XIII) by process B), whereby process A and process B comprise the below process steps:

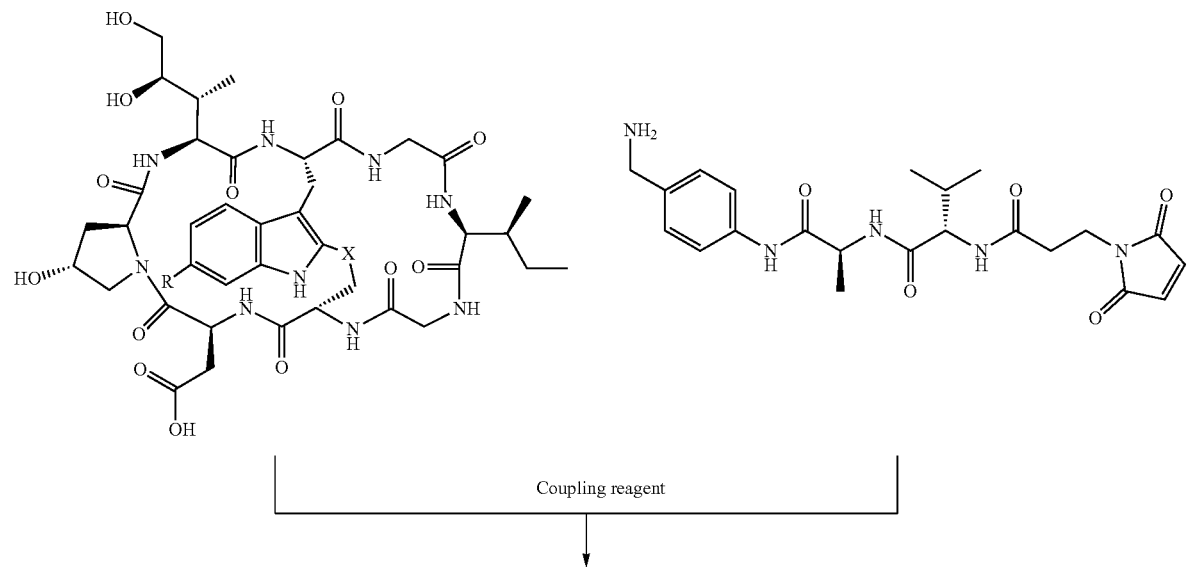

A)

-continued
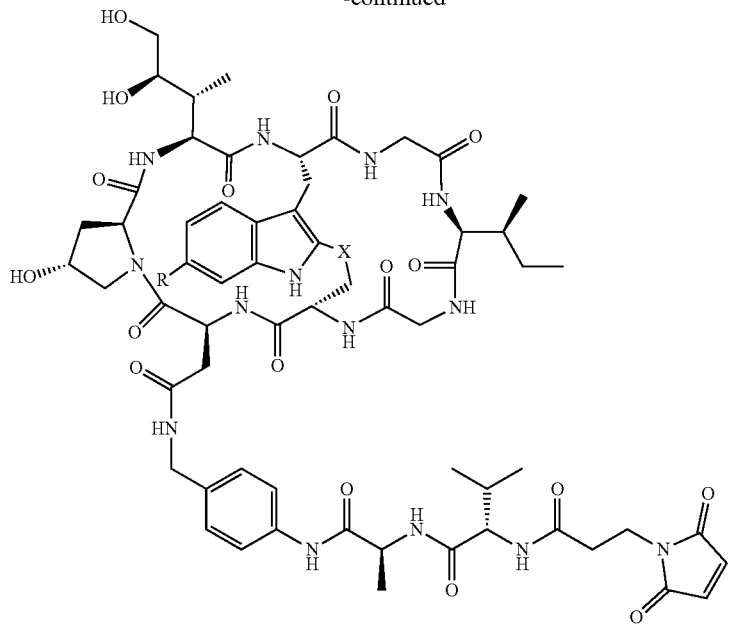
X = S, (R)—SO, SO$_2$
R = H, OH
using one of the coupling reagents 2-(1H-Benzotriazole-1-yl)-1,1,3,3-tetramethylaminium tetrafluoroborate (TBTU), N,N-Diisopropylethylamine (DIPEA), or N,N-Dimethylformamide (DMF) as disclosed in WO 2018/115466 A1, or
B)
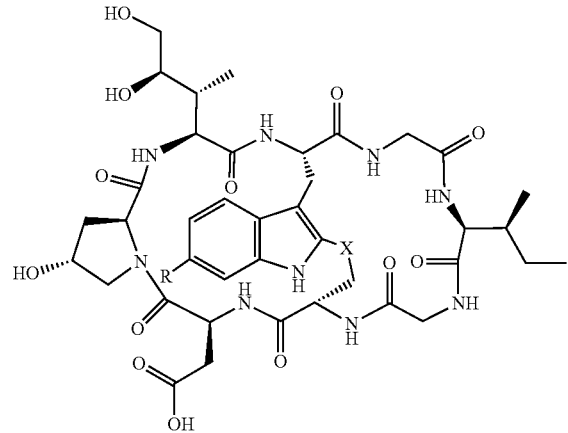

-continued

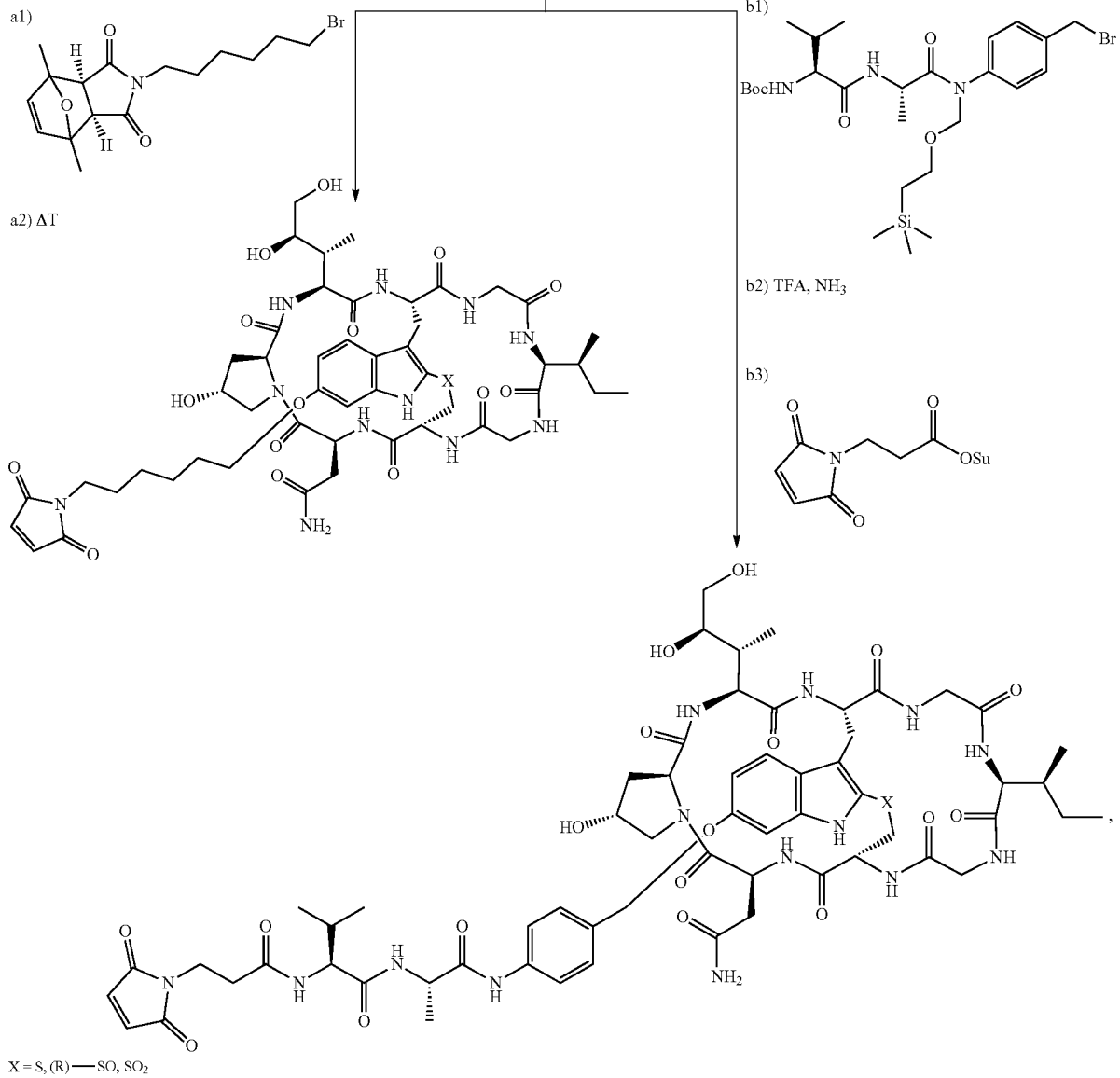

X = S, (R)—SO, SO₂ whereby a1), a2), b1), B2) and b3) refer to
- a1) linker bromide, 1M NaOH, DMSO; a2) 100° C., DMSO
- a1)-a2) are as disclosed in Example 2 of WO 2016/142049 A1
- b1) linker bromide, N,N-dimethylacetamide (DMA), 0.2 M cesium carbonate in water; b2) 1.) TFA, 2.) aqueous ammonia; b3) 3-(maleimido)propionic acid N-hydroxysuccinimide ester, DIPEA, DMF and b1)-b3) are as described in WO 2019/030173 A1
- (step 2) Conjugating the compounds according to any of formulae (II), (III), (IX), (X), (XI), (I), (IV), (V), (VI), (VII), (XIII) to a target-binding moiety according to the invention as described which specifically binds to human CD37 expressed by B lymphocyte-associated malignancy or B cell-mediated autoimmune, whereby the coupling is done as disclosed in WO2016/142049 A1
- (step 3) administering a pharmaceutical composition comprising the conjugate obtained in step 2 to a patient afflicted with B lymphocyte-associated malignancy or B cell-mediated autoimmune disease as disclosed herein.

In one embodiment, the invention pertains to a method of treating a patient suffering from Richter syndrome, wherein the method comprises administering a therapeutically effective amount of the conjugate or pharmaceutical composition of the invention as disclosed above to said patient, wherein the conjugate or pharmaceutical composition may e.g. be administered as monotherapy, or in combination with an immune checkpoint inhibitor as disclosed above.

According to one embodiment, the present invention pertains to a polynucleotide which encodes an amino acid sequence according to SEQ ID NO: 11 and/or SEQ ID NO: 12.

In one embodiment, the present invention pertains to a polynucleotide which comprises SEQ ID NO: 14 and/or SEQ ID NO: 15.

According to one embodiment, the present invention pertains to a host cell which comprises at least one polynucleotide which encodes at least one amino acid sequence according to SEQ ID NO: 11 or SEQ ID NO: 12. The term "host" cell as used herein refers to a prokaryotic or eukaryotic cell that comprises the polynucleotide of the invention, whereby the polynucleotide may be an expression vector. It is preferred that the host cell of the invention is eukaryotic cell, such as a yeast cell (e.g. *Saccharomyces cerevisiae, Hansenula polymorpha, Schizosaccharomyces pombe, Schwanniomyces occidentals, Kluyveromyces lactis, Yarrowia lipolytica* and *Pichia pastoris*), insect cell (e.g. Sf9, Sf21, S2, Hi5, or BTI-TN-5B1-4), more preferably, the host cell of the invention is a mammalian cell selected from HEK293, HEK293T, HEK293E, HEK 293F, NS0, per.C6, MCF-7, HeLa, Cos-1, Cos-7, PC-12, 3T3, Vero, vero-76, PC3, U87, SAOS-2, LNCAP, DU145, A431, A549, B35, H1299, HUVEC, Jurkat, MDA-MB-231, MDA-MB-468, MDA-MB-435, Caco-2, CHO, CHO-K1, CHO-B11, CHO-DG44, BHK, AGE1.HN, Namalwa, WI-38, MRC-5, HepG2, L-929, RAB-9, SIRC, RK13, 11B11, 1D3, 2.4G2, A-10, B-35, C-6, F4/80, IEC-18, L2, MH1C1, NRK, NRK-49F, NRK-52E, RMC, CV-1, BT, MDBK, CPAE, MDCK.1, MDCK.2, and D-17.

Sequences

TABLE 1

| | Amino acid sequences and DNA sequences of the invention | |
|---|---|---|
| SEQ ID No. | Sequence | Description |
| SEQ ID No. 1 | DYNMY | CDRH1 of chHH1-HDP |
| SEQ ID No. 2 | YIDPYNGDTTYNQKFKG | CDRH2 of chHH1-HDP |
| SEQ ID No. 3 | SPYGHYAMDY | CDRH3 of chHH1-HDP |
| SEQ ID No. 4 | KASQDVSTAVD | CDRL1 of chHH1-HDP |
| SEQ ID No. 5 | WASTRHT | CDRL2 of chHH1-HDP |
| SEQ ID No. 6 | RQHYSTPFT | CDRL3 of chHH1-HDP |
| SEQ ID No. 7 | EIQLQQSGPELVKPGASVKVSCKASGYSFT DYNMYWVKQSHGKSLEWIGYIDPYNGDTTY NQKFKGKATLTVDKSSSTAFIHLNSLTSED SAVYYCARSPYGHYAMDYWGQGTSVTVSS | Heavy chain variable region of chHH1-HDP |
| SEQ ID No. 8 | DIVMTQSHKLLSTSVGDRVSITCKASQDVS TAVDWYQQKPGQS PKLLINWASTRHTGVPD RFTGSGSGTDYTLTISSMQAEDLALYYCRQ HYSTPFTFGSGTKLEIKR | Light chain variable region of chHH1-HDP |
| SEQ ID No. 9 | EIQLQQSGPELVKPGASVKVSCKASGYSFT DYNMYWVKQSHGKSLEWIGYIDPYNGDTTY NQKFKGKATLTVDKSSSTAFIHLNSLTSED SAVYYCARSPYGHYAMDYWGQGTSVTVSSA STKGPSVFPLAPSSKSTSGGTAALGCLVKD YFPEPVTVSWNSGALTSGVHTFPAVLQSSG LYSLSSVVTVPSSSLGTQTYICNVNHKPSN TKVDKKVEPKSCDKTHTCPPCPAPE<u>LL</u>GGP SVFLFPPKPKDTLMISRTPEVTCVVV<u>D</u>VSH EDPEVKFNWYVDGVEVHNAKTKPREE<u>QY</u>NS TYRVVSVLTVLHQDWLNGKEYKCKVSNKAL PAPIEKTISKAKGQPREPQVYTLPPSREEM TKNQVSLTCLVKGFYPSDIAVEWESNGQPE NNYKTTPPVLDSDGSFFLYSKLTVDKSRWQ QGNVFSCSVMHEALHNHYTQKSLSLSPGK | Heavy chain of chHH1-HDP |
| SEQ ID No. 10 | EIQLQQSGPELVKPGASVKVSCKASGYSFT DYNMYWVKQSHGKSLEWIGYIDPYNGDTTY NQKFKGKATLTVDKSSSTAFIHLNSLTSED SAVYYCARSPYGHYAMDYWGQGTSVTVSSA STKGPSVFPLAPSSKSTSGGTAALGCLVKD YFPEPVTVSWNSGALTSGVHTFPAVLQSSG LYSLSSVVTVPSSSLGTQTYICNVNHKPSN TKVDKKVEPKSCDKTHTCPPCPAPE<u>LL</u>GGP SVFLFPPKPKDTLMISRTPEVTCVVV<u>C</u>VSH EDPEVKFNWYVDGVEVHNAKTKPREE<u>QY</u>NS TYRVVSVLTVLHQDWLNGKEYKCKVSNKAL PAPIEKTISKAKGQPREPQVYTLPPSREEM TKNQVSLTCLVKGFYPSDIAVEWESNGQPE NNYKTTPPVLDSDGSFFLYSKLTVDKSRWQ QGNVFSCSVMHEALHNHYTQKSLSLSPGK | Heavy chain of chHH1-HDP-D265C comprising amino acid substitution D265C |

TABLE 1-continued

Amino acid sequences and DNA sequences of the invention

| SEQ ID No. | Sequence | Description |
| --- | --- | --- |
| SEQ ID No. 11 | EIQLQQSGPELVKPGASVKVSCKASGYSFT DYNMYWVKQSHGKSLEWIGYIDPYNGDTTY NQKFKGKATLTVDKSSSTAFIHLNSLTSED SAVYYCARSPYGHYAMDYWGQGTSVTVSSA STKGPSVFPLAPSSKSTSGGTAALGCLVKD YFPEPVTVSWNSGALTSGVHTFPAVLQSSG LYSLSSVVTVPSSSLGTQTYICNVNHKPSN TKVDKKVEPKSCDKTHTCPPCPAPEAAGGP SVFLFPPKPKDTLMISRTPEVTCVVVCVSH EDPEVKFNWYVDGVEVHNAKTKPREEQYNS TYRVVSVLTVLHQDWLNGKEYKCKVSNKAL PAPIEKTISKAKGQPREPQVYTLPPSREEM TKNQVSLTCLVKGFYPSDIAVEWESNGQPE NNYKTTPPVLDSDGSFFLYSKLTVDKSRWQ QGNVFSCSVMHEALHNHYTQKSLSLSPGK | Heavy chain of chHH1-HDP-LALA-D265C comprising amino acid substitutions L235A, L235A and D265C |
| SEQ ID No. 12 | DIVMTQSHKLLSTSVGDRVSITCKASQDVS TAVDWYQQKPGQS PKLLINWASTRHTGVPD RFTGSGSGTDYTLTISSMQAEDLALYYCRQ HYSTPFTFGSGTKLEIKRTVAAPSVFIFPP SDEQLKSGTASVVCLLNNFYPREAKVQWKV DNALQSGNSQESVTEQDSKDSTYSLSSTLT LSKADYEKHKVYACEVTHQGLSSPVTKSFN RGEC | Light chain of chHH1-HDP, chHH1-HDP-265C, chHH1-HDP-LALA-D265C, respectively |
| SEQ ID No. 13 | MSAQESCLSLIKYFLFVFNLFFFVLGSLIF CFGIWILIDKTSFVSFVGLAFVPLQIWSKV LAISGIFTMGIALLGCVGALKELRCLLGLY FGMLLLLFATQITLGILISTQRAQLERSLR DVVEKTIQKYGTNPEETAAEESWDYVQFQL RCCGWHYPQDWFQVLILRGNGSEAHRVPCS CYNLSATNDSTILDKVILPQLSRLGHLARS RHSADICAVPAESHIYREGCAQGLQKWLHN NLISIVGICLGVGLLELGFMTLSIFLCRNL DHVYNRLARYR | CD37 human (UniProt-Identifer P11049-1) |
| SEQ ID No. 14 | GAGATCCAGCTGCAGCAGTCTGGACCTGAG CTGGTGAAGCCTGGGGCTTCAGTGAAGGTA TCCTGCAAGGCTTCTGGTTACTCATTCACT GACTACAACATGTACTGGGTGAAGCAGAGC CATGGAAAGAGCCTTGAGTGGATTGGATAT ATTGATCCTTACAATGGTGATACTACCTAC AAC CAGAAGTTCAAGGGCAAGGC CACATTG ACTGTTGACAAGTCCTCCAGCACAGCCTTC ATCCATCTCAACAGCCTGACATCTGAGGAC TCTGCAGTCTATTACTGTGCAAGATCCCCT TATGGTCACTATGCTATGGACTACTGGGGT CAAGGAACCTCAGTCACCGTCTCCTCAGCT AGCACCAAGGGCCCATCGGTCTTCCCCCTG GCACCCTCCTCCAAGAGCACCTCTGGGGGC ACAGCGGCCCTGGGCTGCCTGGTCAAGGAC TACTTCCCCGAACCGGTGACGGTGTCGTGG AACTCAGGCGCCCTGACCAGCGGCGTGCAC ACCTTCCCGGCTGTCCTACAGTCCTCAGGA CTCTACTCCCTCAGCAGCGTGGTGACCGTG CCCTCCAGCAGCTTGGGCACCCAGACCTAC ATCTGCAACGTGAATCACAAGCCCAGCAAC ACCAAGGTGGACAAGAAAGTTGAGCCCAAA TCTTGTGACAAAACTCACACATGCCCACCG TGCCCAGCACCTGAAGCCGCCGGGGGACCG TCAGTCTTCCTCTTCCCCCCAAAACCCAAG GACACCCTCATGATCTCCCGGACCCCTGAG GTCACATGCGTGGTGGTGTGCGTGAGCCAC GAAGACCCTGAGGTCAAGTTCAACTGGTAC GTGGACGGCGTGGAGGTGCATAATGCCAAG ACAAAGCCGCGGGAGGAGCAGTACAACAGC ACGTACCGTGTGGTCAGCGTCCTCACCGTC CTGCACCAGGACTGGCTGAATGGCAAGGAG TACAAGTGCAAGGTCTCCAACAAAGCCCTC CCAGCCCCCATCGAGAAAACCATCTCCAAA GCCAAAGGGCAGCCCCGAGAACCACAGGTG TACACCCTGCCCCCATCCCGGGAGGAGATG ACCAAGAACCAGGTCAGCCTGACCTGCCTG GTCAAAGGCTTCTATCCCAGCGACATCGCC GTGGAGTGGGAGAGCAATGGGCAGCCGGAG AACAACTACAAGACCACGCCTCCCGTGCTG | Heavy chain of chHH1-HDP-LALA-265C, DNA sequence |

TABLE 1-continued

Amino acid sequences and DNA sequences of the invention

| SEQ ID No. | Sequence | Description |
|---|---|---|
| | GACTCCGACGGCTCCTTCTTCCTCTACAGC<br>AAGCTCACCGTGGACAAGAGCAGGTGGCAG<br>CAGGGGAACGTCTTCTCATGCTCCGTGATG<br>CATGAGGCTCTGCACAACCACTACACGCAG<br>AAGAGCCTCTCCCTGTCTCCGGGTAAA | |
| SEQ ID No. 15 | GACATTGTGATGACCCAGTCTCACAAACTC<br>TTGTCCACATCAGTAGGAGACAGGGTCAGC<br>ATCACCTGCAAGGCCAGTCAGGATGTGAGT<br>ACTGCTGTAGACTGGTATCAACAGAAACCA<br>GGACAATCTCCTAAACTACTGATTAACTGG<br>GCATCCACCCGGCACACTGGAGTCCCTGAT<br>CGCTTCACAGGCAGTGGATCTGGGACAGAT<br>TATACTCTCACCATCAGCAGTATGCAGGCT<br>GAAGACCTGGCACTTTATTACTGTCGACAA<br>CATTATAGCACTCCATTCACGTTCGGCTCG<br>GGGACAAAGTTGGAAATAAAACGAACGGTG<br>GCTGCACCATCTGTCTTCATCTTCCCGCCA<br>TCTGATGAGCAGTTGAAATCCGGAACTGCC<br>TCTGTTGTGTGCCTGCTGAATAACTTCTAT<br>CCCAGAGAGGCCAAAGTACAGTGGAAGGTG<br>GATAACGCCCTCCAATCGGGTAACTCCCAG<br>GAGAGTGTCACAGAGCAGGACAGCAAGGAC<br>AGCACCTACAGCCTCAGCAGCACCCTGACG<br>CTGAGCAAAGCAGACTACGAGAAACACAAA<br>GTCTACGCCTGCGAAGTCACCCATCAGGGC<br>CTGAGCTCGCCCGTCACAAAGAGCTTCAAC<br>AGGGGAGAGTGT | Light chain of chHH1-HDP,<br>chHH1-HDP-265C, chHH1-<br>HDP-LALA-265C, DNA<br>sequence |
| SEQ ID NO: 16 | MSAQESCLSLIKYFLFVFNLFFFVLGSLIFCFG<br>IWILIDKTSFVSFVGLAFVPLQIWSKVLAISGV<br>FTMGLALLGCVGALKELRCLLGLYFGMLLLLFA<br>TQITLGILISTQRAQLERSLQDIVEKTIQKYHT<br>NPEETAAEESWDYVQFQVSPLLQLPPRLTRLSP<br>VLRGDSTPTWPRPPALHDLTHSQPLPGPTPATP<br>QMTQLAPAWPSLPVPRPWHGFAIYLGRLRPRPD<br>PAPTGGSQAPSPKTLARHGFLPRSESGFHRTPP<br>RMRLTGSRTPIHLSGIRGSIAPPTNLWFRARRC<br>SYFPSPRSPRDPSLPAPFPVMSPGPGPIATPAH<br>WPPLHTHHLVPCFPT | Cynomolgus CD37<br>UniProt identifier A0A7N9CZJ5 |

EXAMPLES

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

All amino acid sequences disclosed herein are shown from N-terminus to C-terminus; all nucleic acid sequences disclosed herein are shown 5'->3'.

Example 1: Synthesis and Characterization of Amatoxin Antibody Conjugates

Example 1.1: Expression of CD37-Specific Antibodies

CD37-specific monoclonal antibodies used in the examples (chHH1-HDP, chHH1-HDP-D265C, and chHH1-HDP-LALA-D265C) were expressed in CHO cells and purified by protein A chromatography. Yields achieved were ca. 58 mg/Liter. The preparation was determined to contain 93.90% antibody monomers, and only 1.54% to 1.88% high molecular weight aggregates.

CD37-specific monoclonal antibodies used in the examples (chHH1-HDP, chHH1-HDP-D265C, and chHH1-HDP-LALA-D265C) were also expressed in HEK293 cells and purified by protein A chromatography and size exclusion chromatography (SEC). Yields achieved were ca. 50 mg/Liter. The preparation was determined to contain 95.26% antibody monomers, and only 2.38% high molecular weight aggregates.

Example 1.2: Synthesis of Amatoxin-Linker Constructs

Example 1.3: Synthesis of Anti-CD37 Amatoxin Conjugates

Antibodies were conjugated to the amatoxin linker conjugates by means of the so-called Thiomab technology. In this approach, the conjugation takes place by coupling of the maleimide residue of the toxin linker construct to the free SH group of a cysteine residue in the antibody, as shown in the reaction scheme of FIG. 19.

The principles of this conjugation method are disclosed in Junutula et al. (2008), the content of which is incorporated herein by reference.

The antibodies used in the present experiments comprise a D265C substitution in both Fc domains, in order to provide a cystein residue that has a free SH group. The respective technology is disclosed in WO2016/142049 A1, the content of which is incorporated herein by reference, and which results in a homogenous product with a fixed drug to antibody ratio ("DAR") of about 2 and a site specific conjugation.

Example 2: Binding of CD37-Specific Antibody chHH1-HDP to Lymphoma Cell Lines

Example 2.1: Cell Cytometry Binding Assay

Figure 3:
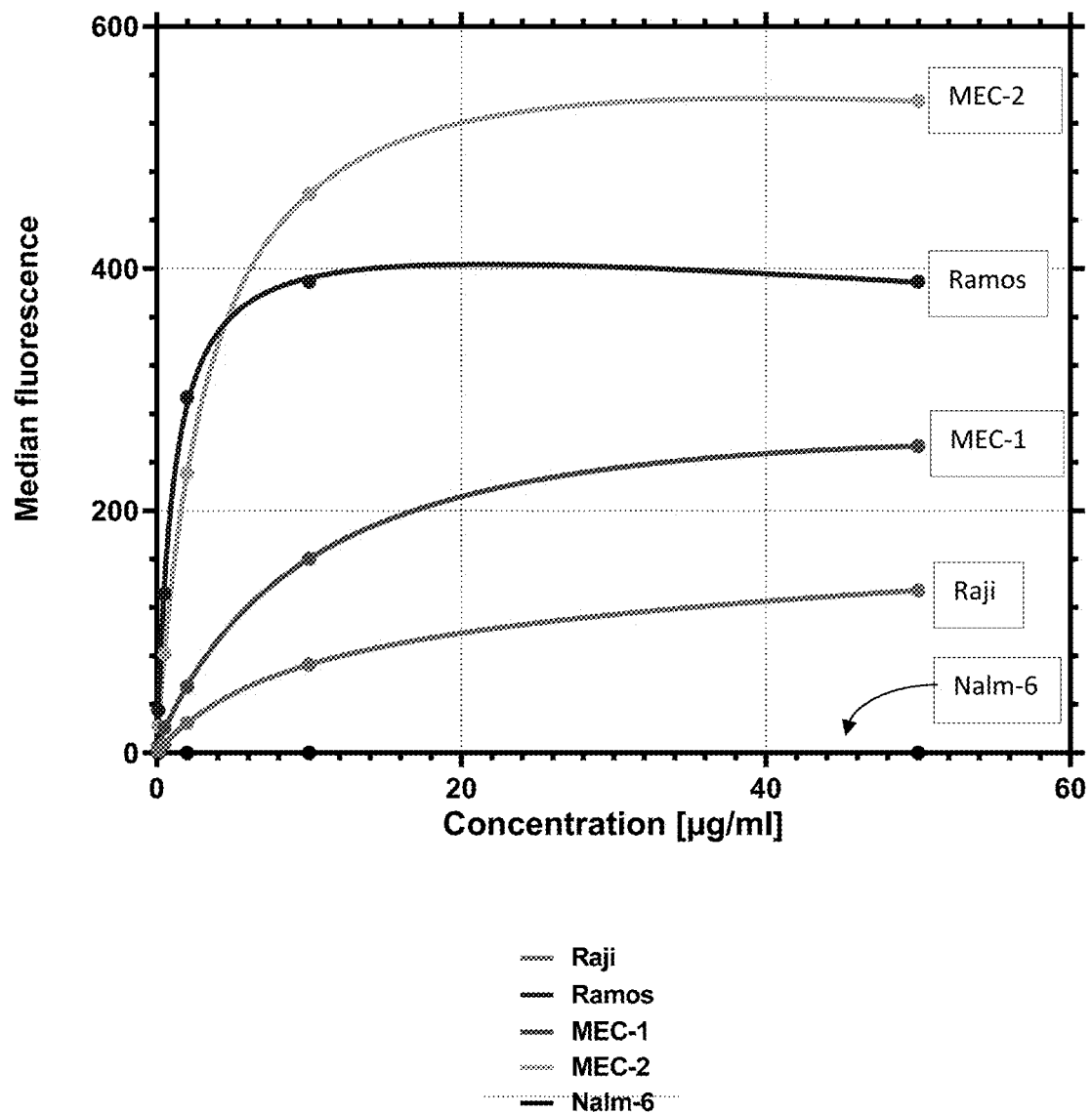
FIG. 3. Binding of the anti-CD37 monoclonal antibody chHH1-LALA-D265C to the B-cell leukemia (B-CLL) cell lines MEC-1 and MEC-2, to the human Burkitt lymphoma cell lines Raji and Ramos, respectively, and to the human B-cell precursor leukemia cell line Nalm-6, by fluorescence-activated cell sorting (FACS) analysis.

Binding of the anti-CD37 monoclonal antibody chHH1-HDP-LALA-D265C to the CD37-positive B-cell leukemia (B-CLL) cell lines MEC-1 and MEC-2 as well as to the human Burkitt lymphoma cell lines Raji and Ramos and to the human B-cell precursor leukemia cell line Nalm-6, which is known to be CD37-negative, were tested by fluorescence-activated cell sorting (FACS) analysis. The antibody chHH1-HDP-LALA-D265C was shown to bind strongly to the CD37-positive MEC-1, MEC-2, Raji and Ramos cell lines (FIG. 3). No binding was detected with Nalm-6 cells.

In order to estimate antibodies bound per cell (ABC) by flow cytometry, BD Quantibrite PE tubes (Becton Dickinson) were used, which were run at the same instrument settings as the assay, so that the FL2 axis can be converted into the number of PE molecules bound per cell. By using known ratios of PE to antibodies, PE molecules per cell can then be converted to the number of antibodies per cell (Iyer et al. 1997). Results are shown in Table 2.

TABLE 2

Estimation of anti-CD37 antibody molecules bound per cell by flow cytometry

| Cell Line | chHH1-HDP-LALA-D265C antibodies bound per cell (ABC) value |
|---|---|
| Raji | 32,500 |
| MEC-1 | 33,004 |
| MEC-2 | 137,200 |
| Ramos | 31,500 |
| Nalm-6 | 42 |

Example 2.2: Biacore Binding Assay

Binding of the monoclonal antibody chHH1-HDP-LALA-D265C to CD37 was confirmed by surface-plasmon resonance (Biacore) interaction analysis. 0.1 µM chHH1-HDP-LALA-D265C was captured using anti-Fab capture (FAB2G) biosensors. Alternatively, biotinylated monoclonal antibody chHH1-HDP-LALA-D265C was captured by streptavidin (SA) sensors. A CD37 construct comprising amino acids Ala 113 to Asn 240, expressed in HEK293 cells with an Fc fusion tag moiety (Thr 106 to Lys 330), was added to the sensor at concentrations of 31.25 nM to 500 nM (1:2 dilution steps), and binding of the CD37 construct was assessed.

Alternatively, CD37 constructs comprising amino acids 1 to 281 expressed in insect cells were used for confirming of binding of the monoclonal antibody chHH1-HDP-LALA-D265C to CD37.

Example 3: Cytotoxicity of Anti-CD37 Amatoxin Conjugates In Vitro

Figure 4A:
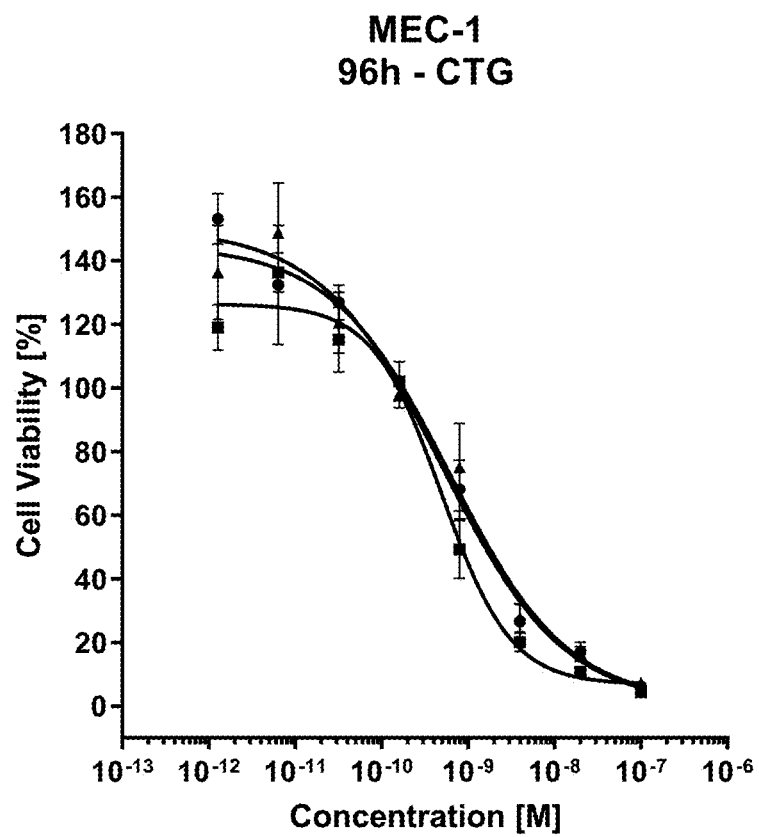
FIG. 4A. Results of cytotoxicity studies in vitro on CD37-positive MEC-1 cells, using different anti-CD37-antibody-targeted amatoxin conjugates in a CTG assay after incubation for 96 hours.
Figure 4B:
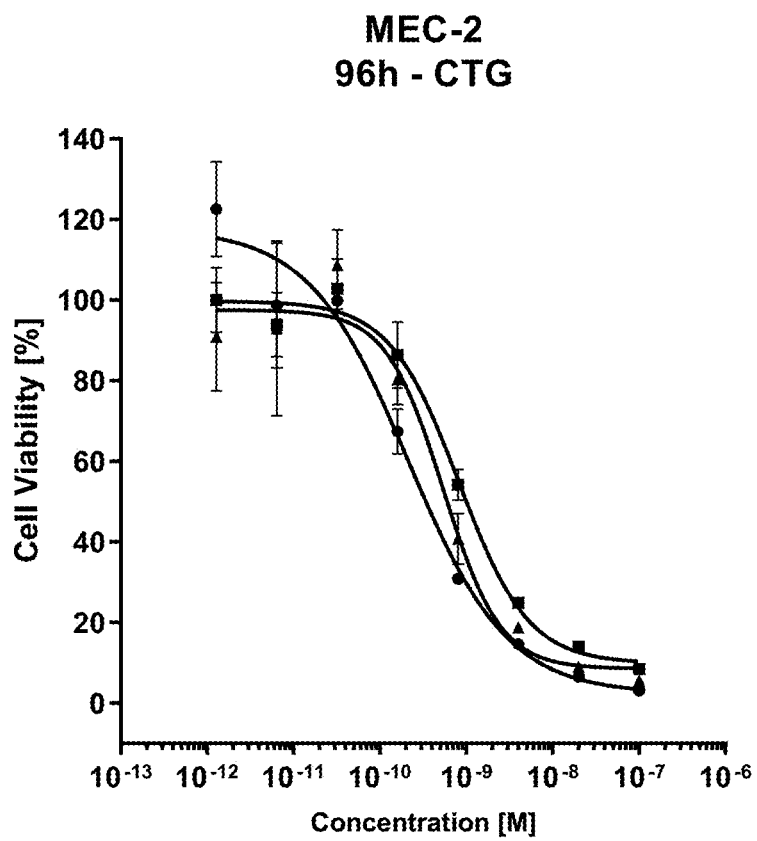
FIG. 4B. Results of cytotoxicity studies in vitro on CD37-positive MEC-2 cells, using different anti-CD37-antibody-targeted amatoxin conjugates in a CTG assay after incubation for 96 hours.
Figure 4:
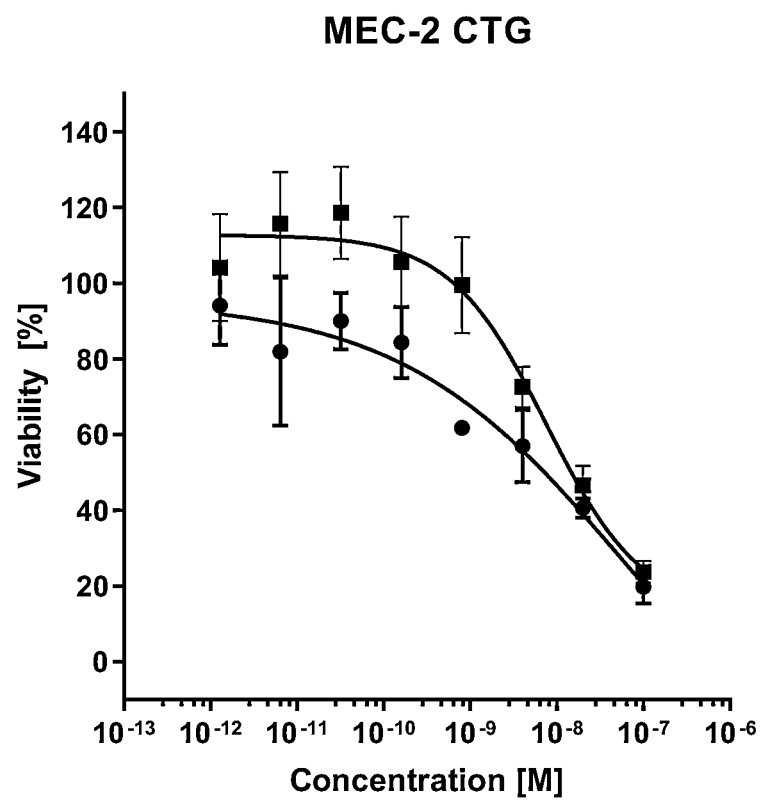
FIG. 4C. Results of cytotoxicity studies in vitro on CD37-positive MEC-2 cells, using different anti-CD37-antibody-targeted amatoxin conjugates in a CTG assay after incubation for 96 hours.
FIG. 4D. Results of cytotoxicity studies in vitro on CD37-positive MEC-2 cells, using different anti-CD37-antibody-targeted amatoxin conjugates in a CTG assay after incubation for 96 hours.
FIG. 4E. Results of cytotoxicity studies in vitro on CD37-positive MEC-2 cells, using different anti-CD37-antibody-targeted amatoxin conjugates in a CTG assay after incubation for 96 hours.
FIG. 4F. Results of cytotoxicity studies in vitro on CD37-positive MEC-2 cells, using different anti-CD37-antibody-targeted amatoxin conjugates in a CTG assay after incubation for 96 hours.
FIG. 4G. Results of cytotoxicity studies in vitro on CD37-positive MEC-2 cells, using different anti-CD37-antibody-targeted amatoxin conjugates in a CTG assay after incubation for 96 hours.
Figure 4D:
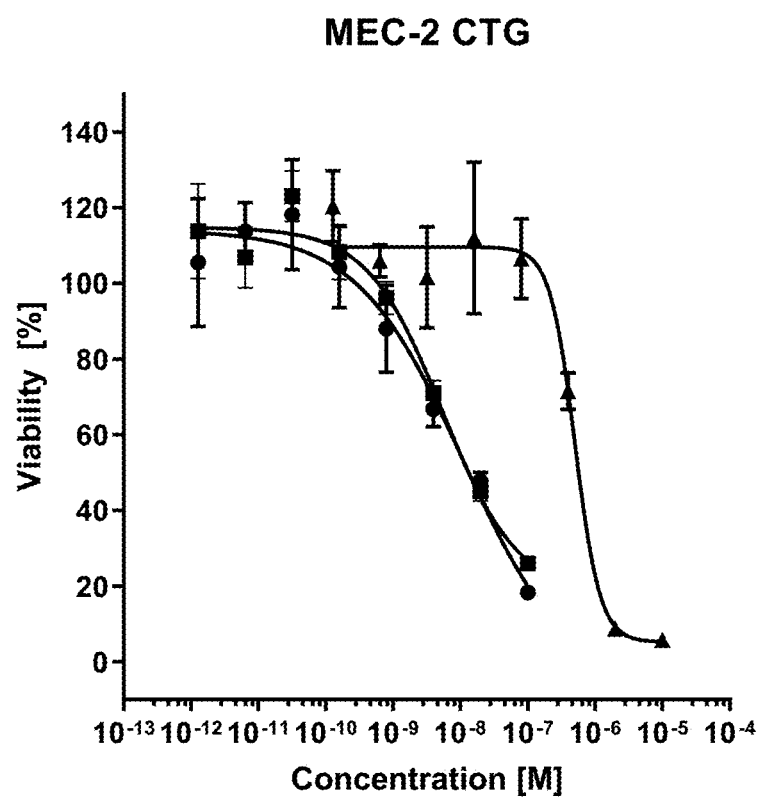
Figure 4E:
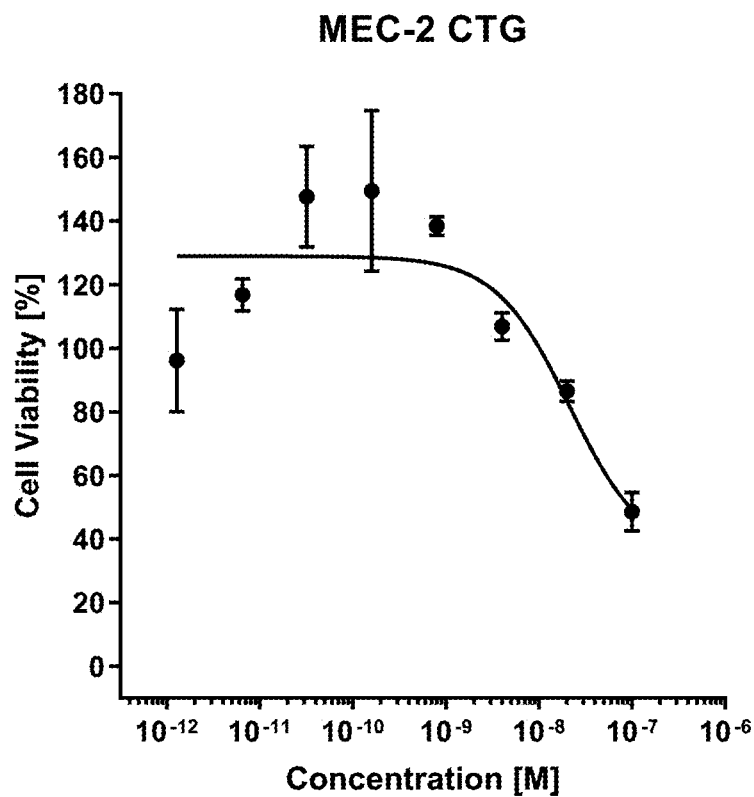
Figure 4F:
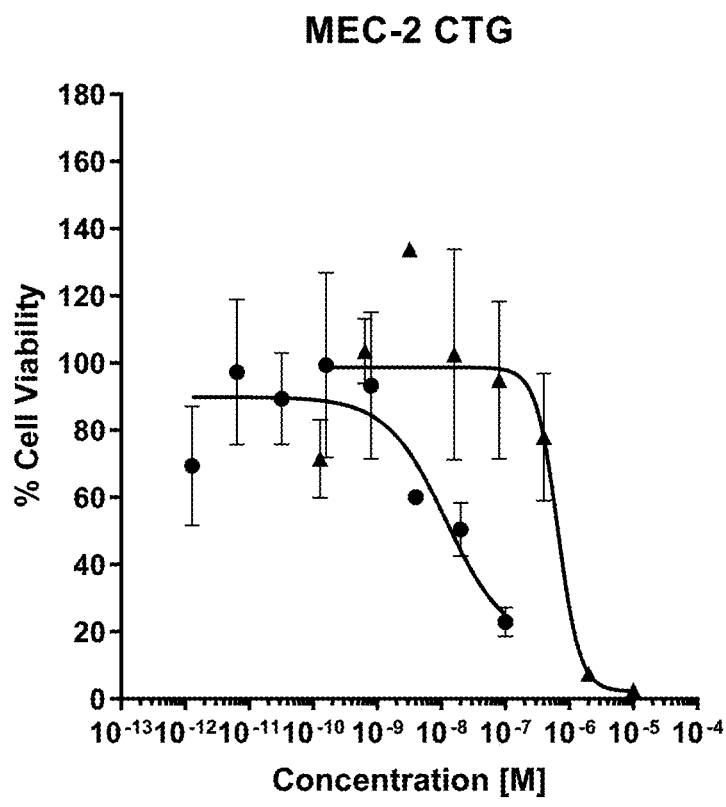
Figure 4G:
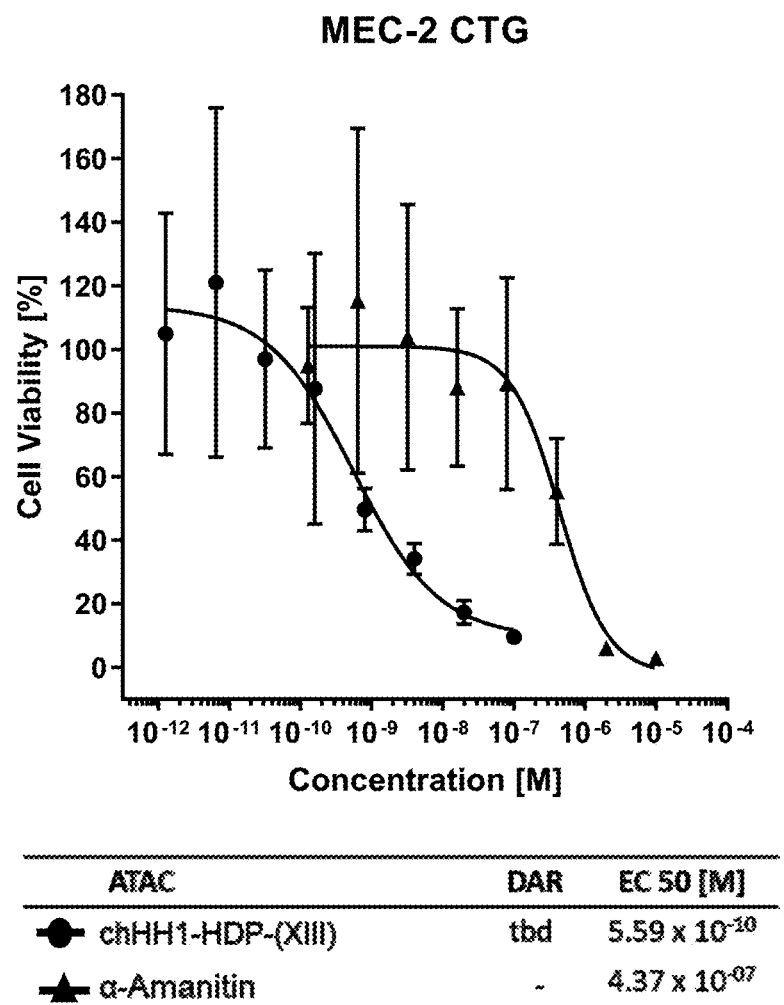
Figure 5A:
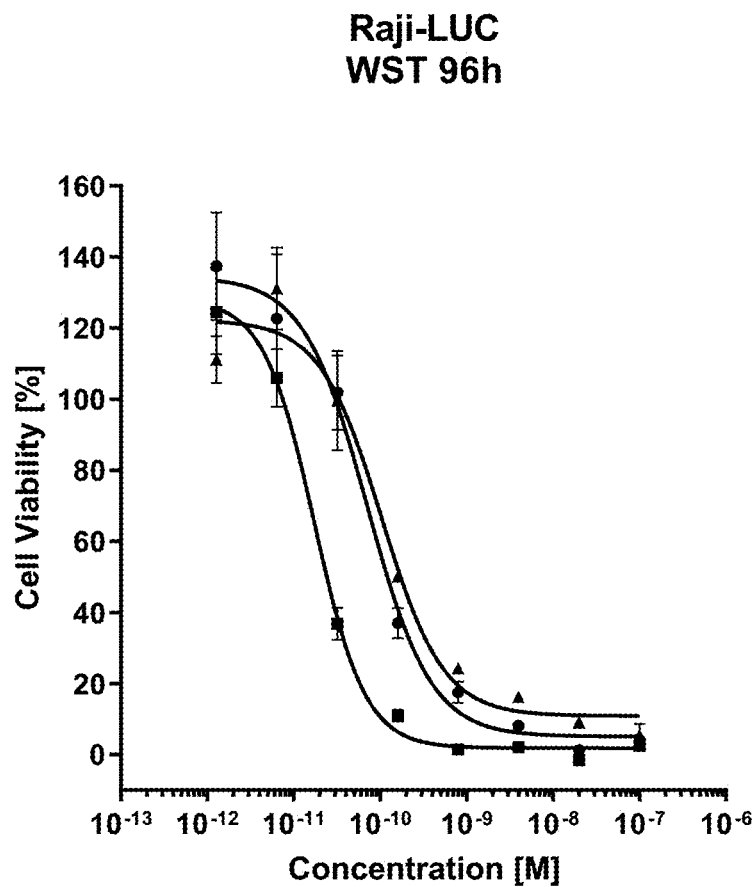
FIG. 5A. Results of cytotoxicity studies in vitro on CD37-positive Raji-Luc cells using different anti-CD37-antibody-targeted amatoxin conjugates in a WST-1 cell proliferation assay.
Figure 5B:
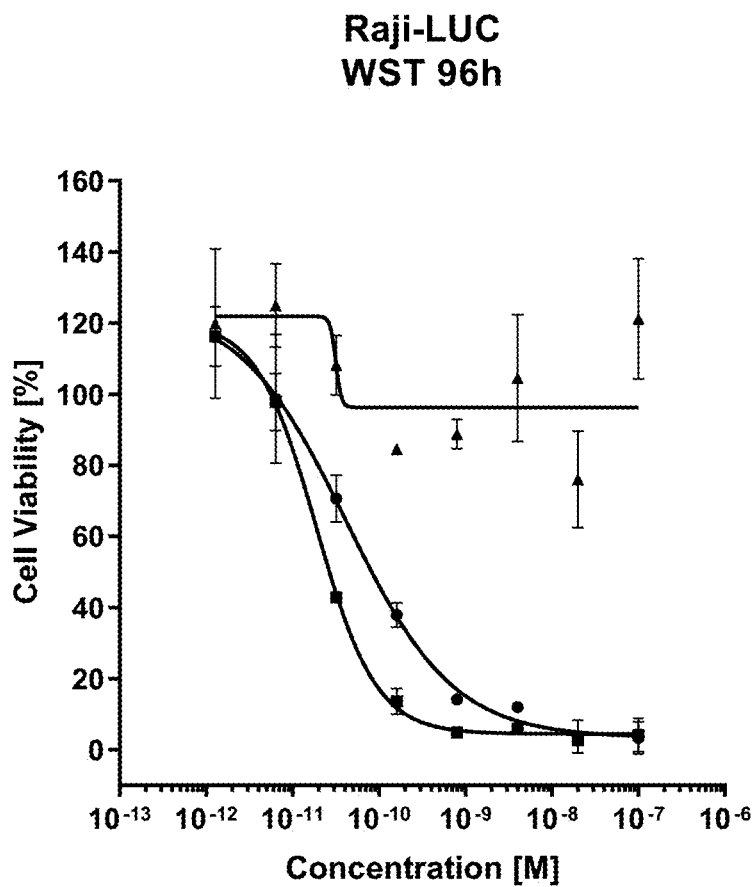
FIG. 5B. Results of cytotoxicity studies in vitro on CD37-positive Raji-Luc cells using different anti-CD37-antibody-targeted amatoxin conjugates in a WST-1 cell proliferation assay.
Figure 5C:
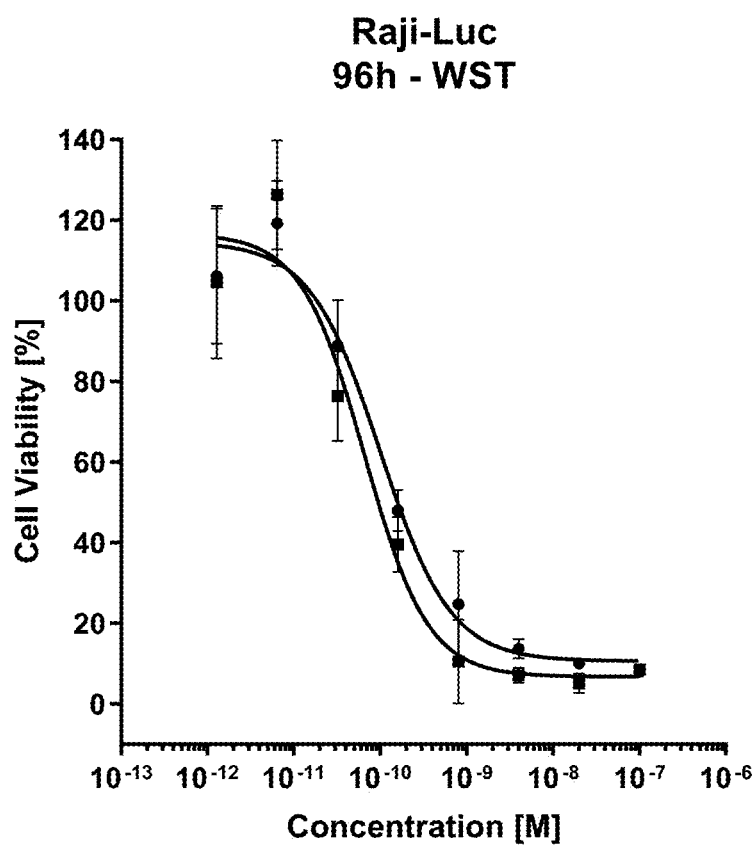
FIG. 5C. Results of cytotoxicity studies in vitro on CD37-positive Raji-Luc cells using different anti-CD37-antibody-targeted amatoxin conjugates in a WST-1 cell proliferation assay.
Figure 5D:
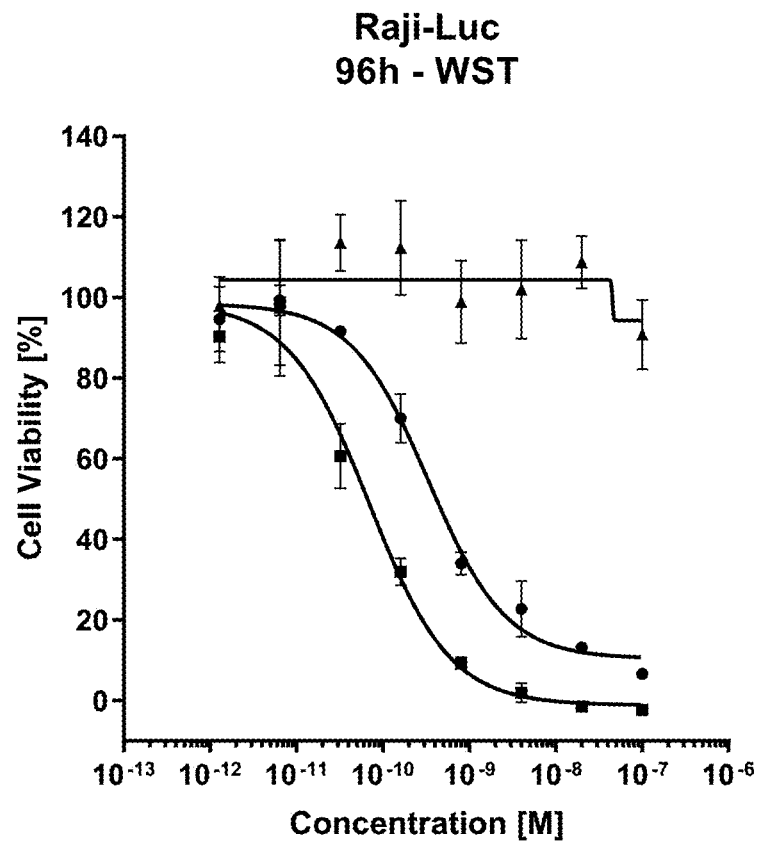
FIG. 5D. Results of cytotoxicity studies in vitro on CD37-positive Raji-Luc cells using different anti-CD37-antibody-targeted amatoxin conjugates in a WST-1 cell proliferation assay.
Figure 6A:
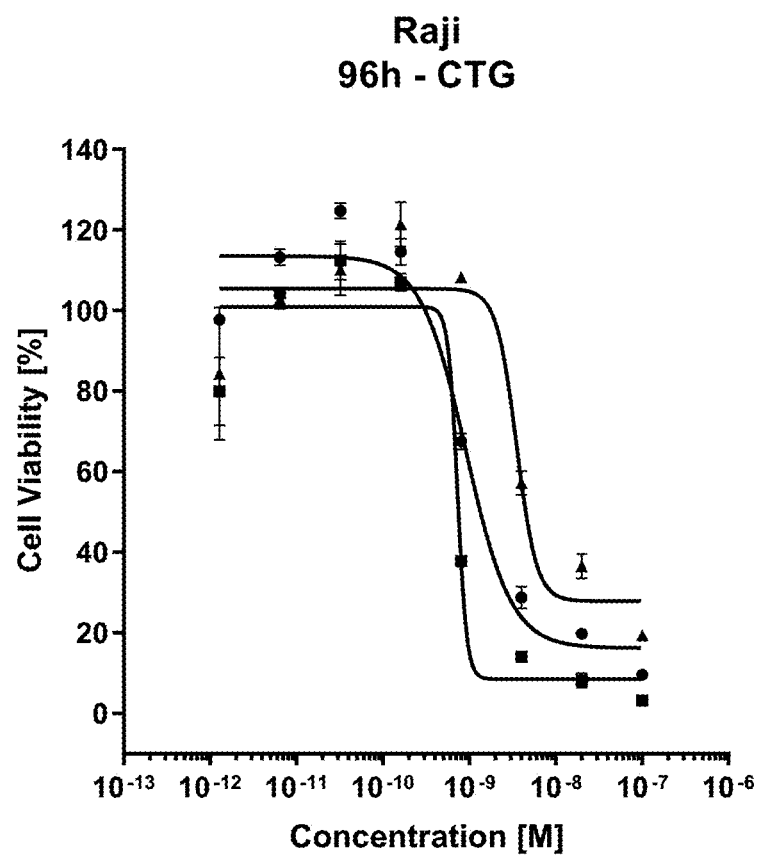
FIG. 6A. Results of cytotoxicity studies in vitro on CD37-positive Raji cells using different anti-CD37-antibody-targeted amatoxin conjugates in a CTG assay following incubation for 96 hours with amatoxin-conjugates as indicated.
Figure 6B:
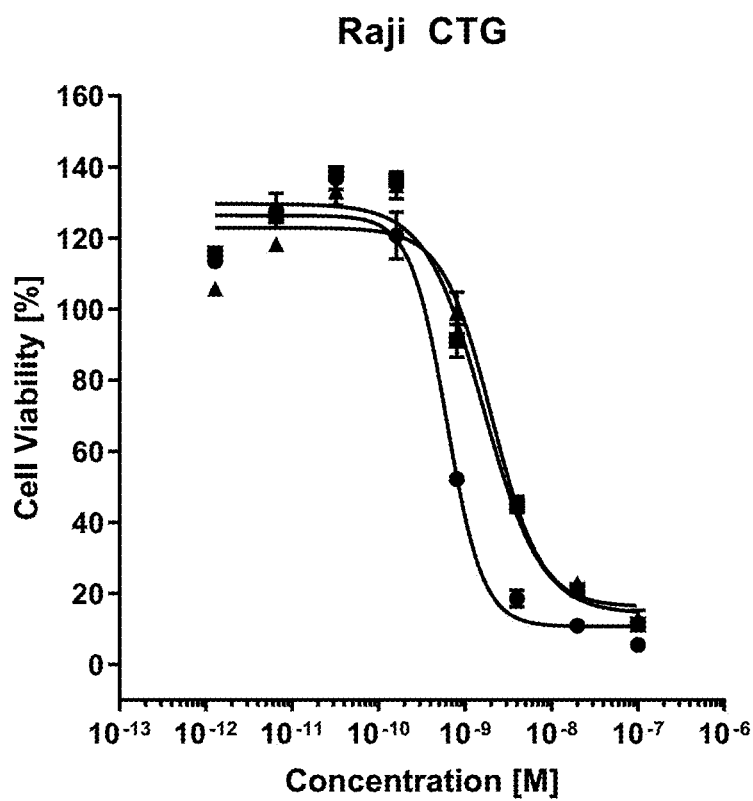
FIG. 6B. Results of cytotoxicity studies in vitro on CD37-positive Raji cells using different anti-CD37-antibody-targeted amatoxin conjugates in a CTG assay following incubation for 96 hours with amatoxin-conjugates as indicated.
Figure 6C:
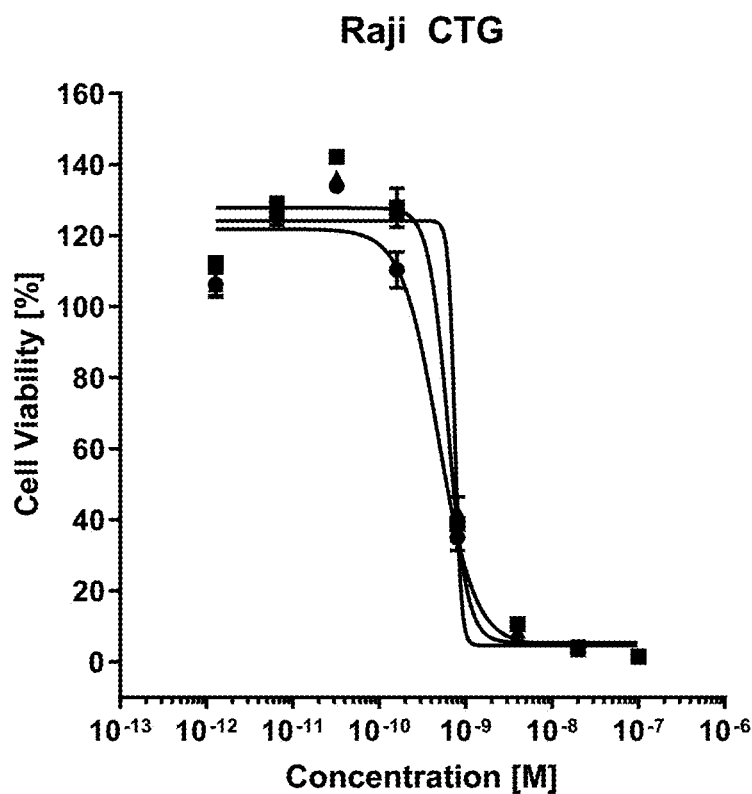
FIG. 6C. Results of cytotoxicity studies in vitro on CD37-positive Raji cells using different anti-CD37-antibody-targeted amatoxin conjugates in a CTG assay following incubation for 96 hours with amatoxin-conjugates as indicated.
Figure 6D:
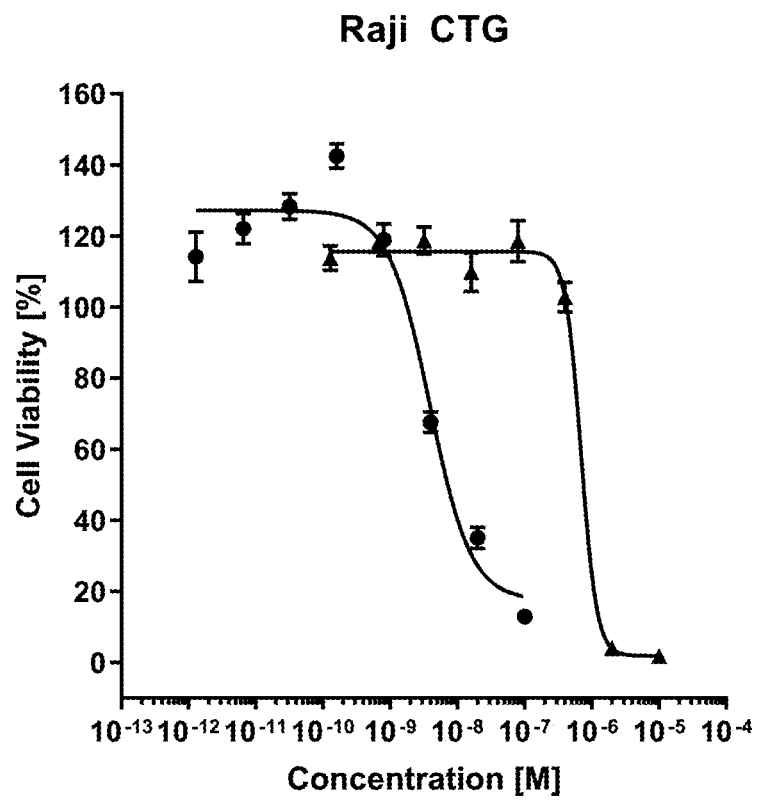
FIG. 6D. Results of cytotoxicity studies in vitro on CD37-positive Raji cells using different anti-CD37-antibody-targeted amatoxin conjugates in a CTG assay following incubation for 96 hours with amatoxin-conjugates as indicated.
Figure 6E:
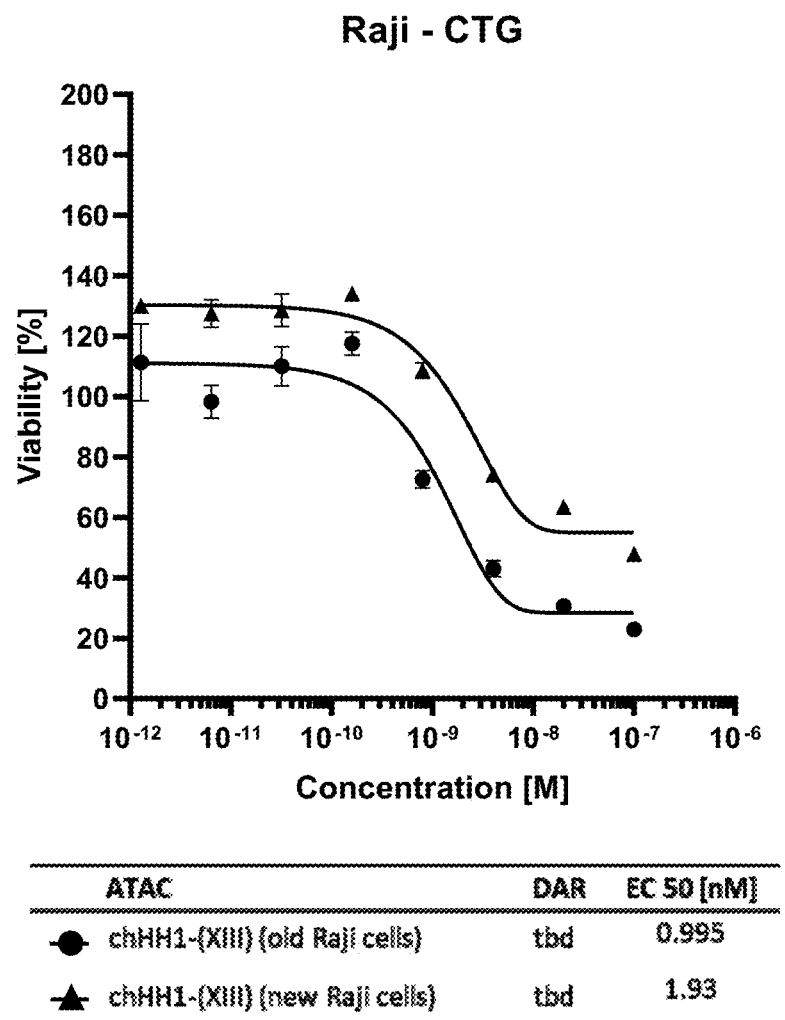
FIG. 6E. Results of cytotoxicity studies in vitro on CD37-positive Raji cells using different anti-CD37-antibody-targeted amatoxin conjugates in a CTG assay following incubation for 96 hours with amatoxin-conjugates as indicated.
Figure 7A:
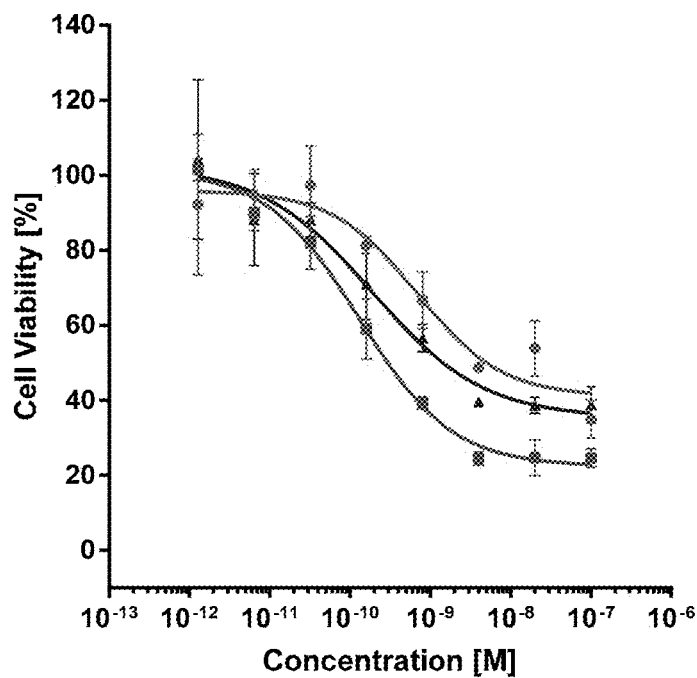
FIG. 7A. Results of cytotoxicity studies in vitro on CD37-positive Ramos cells using different anti-CD37-antibody-targeted amatoxin conjugates in a CTG assay following incubation for 96 hours with amatoxin-conjugates as indicated.
Figure 7B:
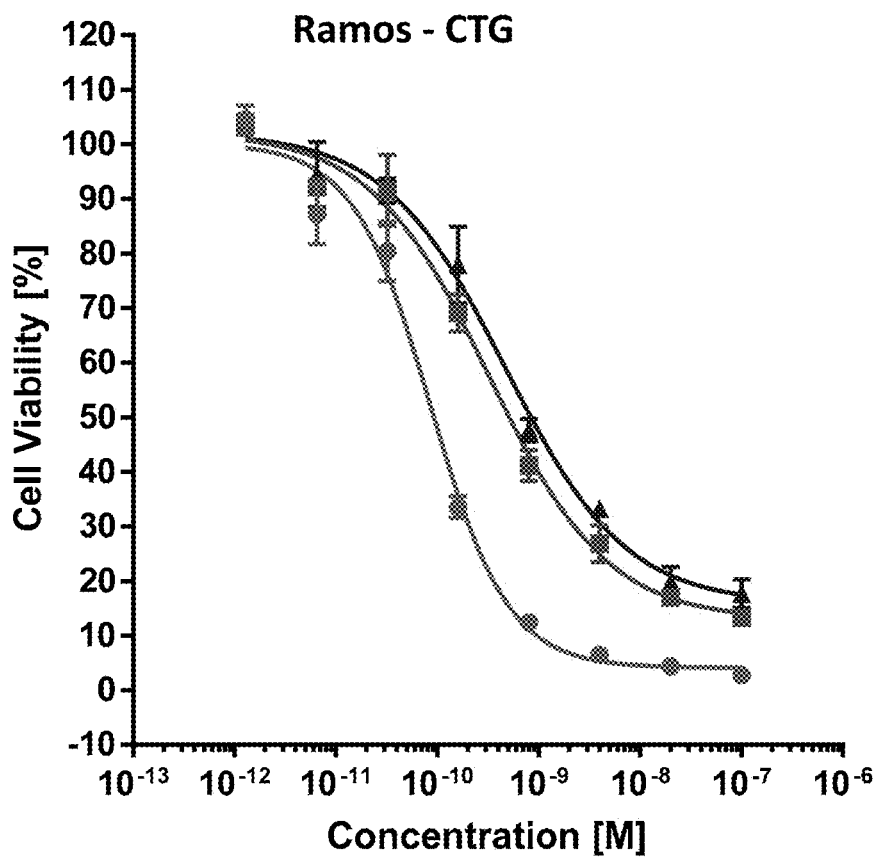
FIG. 7B. Results of cytotoxicity studies in vitro on CD37-positive Ramos cells using different anti-CD37-antibody-targeted amatoxin conjugates in a CTG assay following incubation for 96 hours with amatoxin-conjugates as indicated.
Figure 7C:
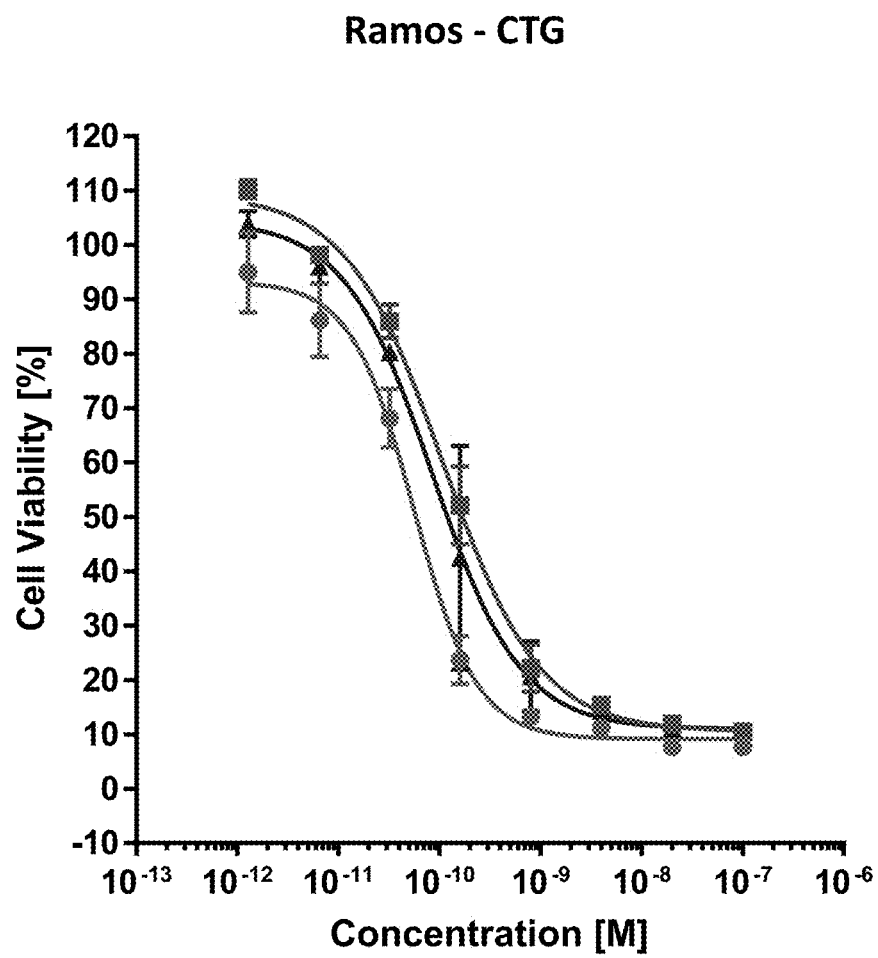
FIG. 7C. Results of cytotoxicity studies in vitro on CD37-positive Ramos cells using different anti-CD37-antibody-targeted amatoxin conjugates in a CTG assay following incubation for 96 hours with amatoxin-conjugates as indicated.
Figure 7D:
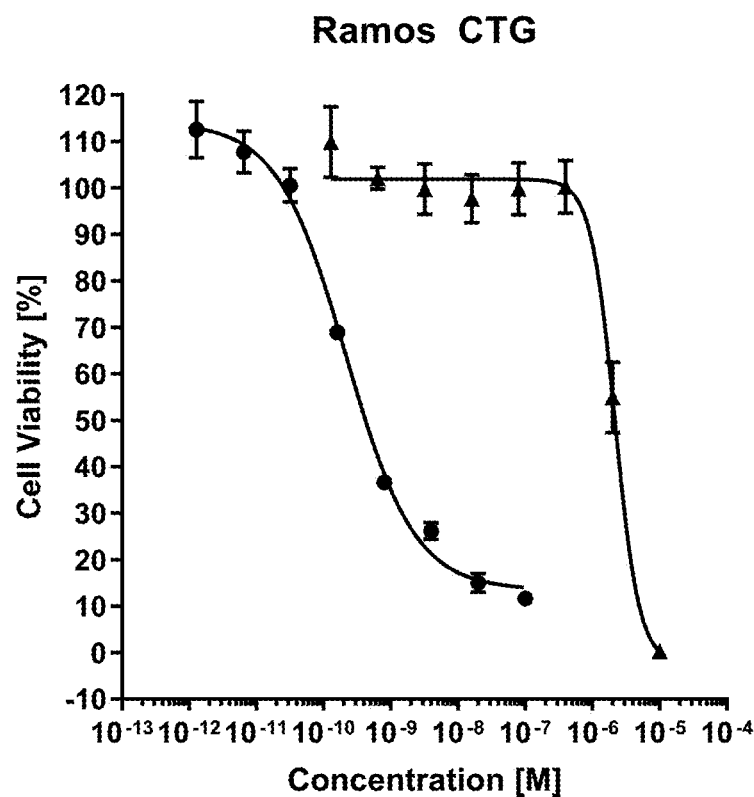
FIG. 7D. Results of cytotoxicity studies in vitro on CD37-positive Ramos cells using different anti-CD37-antibody-targeted amatoxin conjugates in a CTG assay following incubation for 96 hours with amatoxin-conjugates as indicated.
Figure 8:
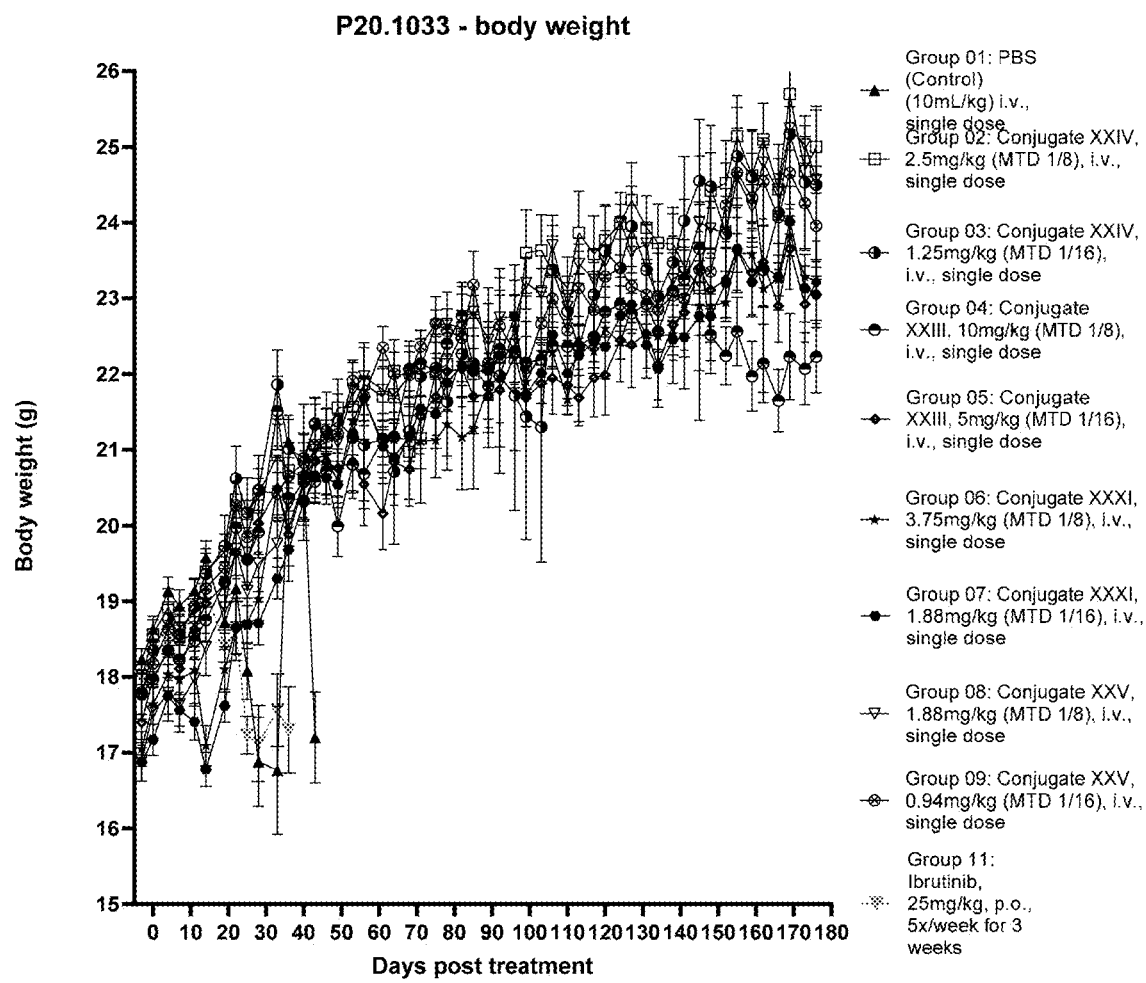
FIG. 8. Results of cytotoxic efficacy studies in vivo using various anti-CD37 amatoxin conjugates in a disseminated MEC2 tumor xenograft model over 180 days of treatment showing the body weight of the individual treatment groups.
Figure 9:
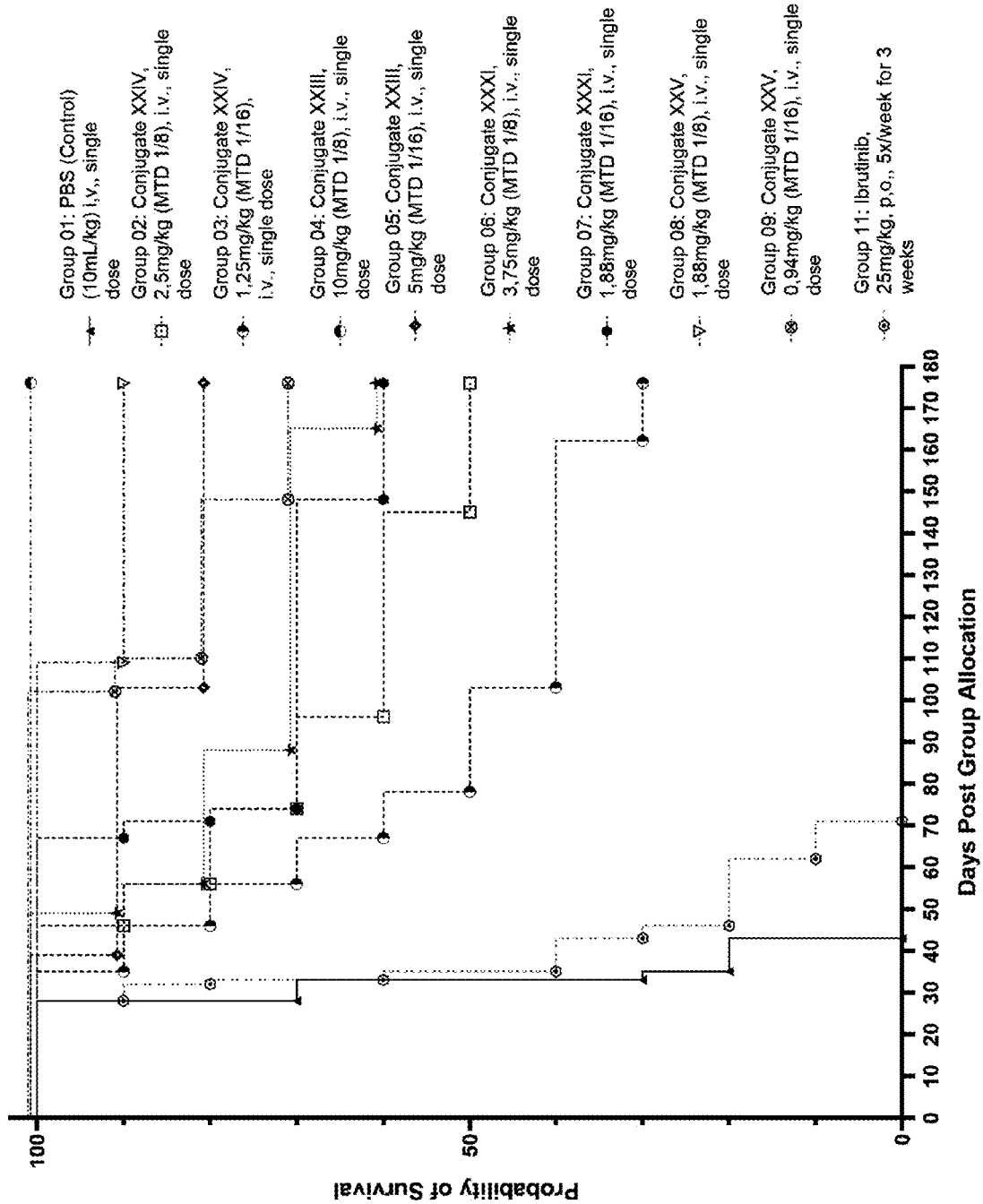
FIG. 9. Results of cytotoxic efficacy studies in vivo using various anti-CD37 amatoxin conjugates as indicated in a disseminated MEC2 tumor xenograft model over 180 days of treatment: Survival.

Cytotoxicity studies in vitro were performed on CD37-positive MEC-1 cells and CD37-positive MEC-2 cells (B-chronic lymphocytic leukemia); on CD37-positive Raji-Luc, Raji and Ramos cells, respectively (Burkitt's lymphoma); and CD37-negative Nalm-6 cells (B-cell precursor leukemia), respectively, using different anti-CD37-antibody-targeted amatoxin conjugates in a CTG assay after incubation for 96 hours, or a WST-1 assay. The results are shown in FIG. 4A (MEC-1 cells), FIG. 4 B-G (MEC-2 cells), FIG. 5A-D (Raji-Luc cells), FIG. 6A-E (Raji cells), FIG. 7A-D (Ramos cells) The results are summarized in Table 3.

The quantitative determination of cell viability was performed by using the CTG (CellTiter Glo 2.0) assay (Promega), a homogeneous method to determine the number of viable cells in culture based on quantitation of the ATP present, which signals the presence of metabolically active cells. By use of the assay, a "glow-type" luminescent signal is generated, produced by the luciferase reaction, which can be detected.

The quantitative determination of cell viability in some experiments was performed by using a commercially available WST-1 assay (Roche). The "Cell Proliferation Reagent" WST-1 is designed to be used for the spectrophotometric quantification of cell viability, in cell populations using multi-well-plate format, and is based on the cleavage of the slightly red tetrazolium salt WST-1 (4-[3-(4-Iodophenyl)-2-(4-nitro-phenyl)-2H-5-tetrazolio]-1,3-benzene sulfonate) to the dark red formazan.

All tested anti-CD37 ATACs showed in vitro cytotoxicity in the picomolar range on CD37-positive cell lines. No cytotoxic activity on CD37-negative cells was observed.

TABLE 3

Summary of cytotoxicity results in vitro

| ATAC | DAR | EC 50 [M] | | |
|---|---|---|---|---|
| | | MEC-2 | Raji | Ramos |
| chHH1-HDP-(XV) | 3.36 | $6.06 \times 10^{-8}$ | $6.10 \times 10^{-10}$ | $8.5 \times 10^{-11}$ |
| chHH1-HDP-D265C-(XV) | 2.80 | $1.11 \times 10^{-8}$ | $1.63 \times 10^{-9}$ | $4.7 \times 10^{-10}$ |
| conjugate XXVI | 3.15 | $7.54 \times 10^{-9}$ | $2.04 \times 10^{-9}$ | $3.2 \times 10^{-10}$ |
| chHH1-HDP-(XIII) | — | $5.59 \times 10^{-10}$ | $4.80 \times 10^{-10}$ | $5.6 \times 10^{-11}$ |
| chHH1-HDP-D265C-(XIII) | 1.96 | $5.41 \times 10^{-9}$ | $6.20 \times 10^{-10}$ | $1.1 \times 10^{-10}$ |
| conjugate XXIV | — | $1.19 \times 10^{-8}$ | $7.50 \times 10^{-10}$ | $8.6 \times 10^{-11}$ |
| chHH1-HDP-D265C-(XII) | 2.03 | $2.14 \times 10^{-8}$ | $3.90 \times 10^{-9}$ | $2.2 \times 10^{-10}$ |

Example 4: Cytotoxicity of Anti-CD37 Amatoxin Conjugates in Mouse Models In Vivo Example 4.1: Cytotoxic Efficacy of Anti-CD37 Amatoxin Conjugates in Disseminated MEC-2 Tumor Xenograft Model Cytotoxic efficacy studies in vivo were performed using various anti-CD37 antibody amatoxin conjugates in a disseminated MEC-2 tumor xenograft model over 140 days of treatment.

Figure 10:
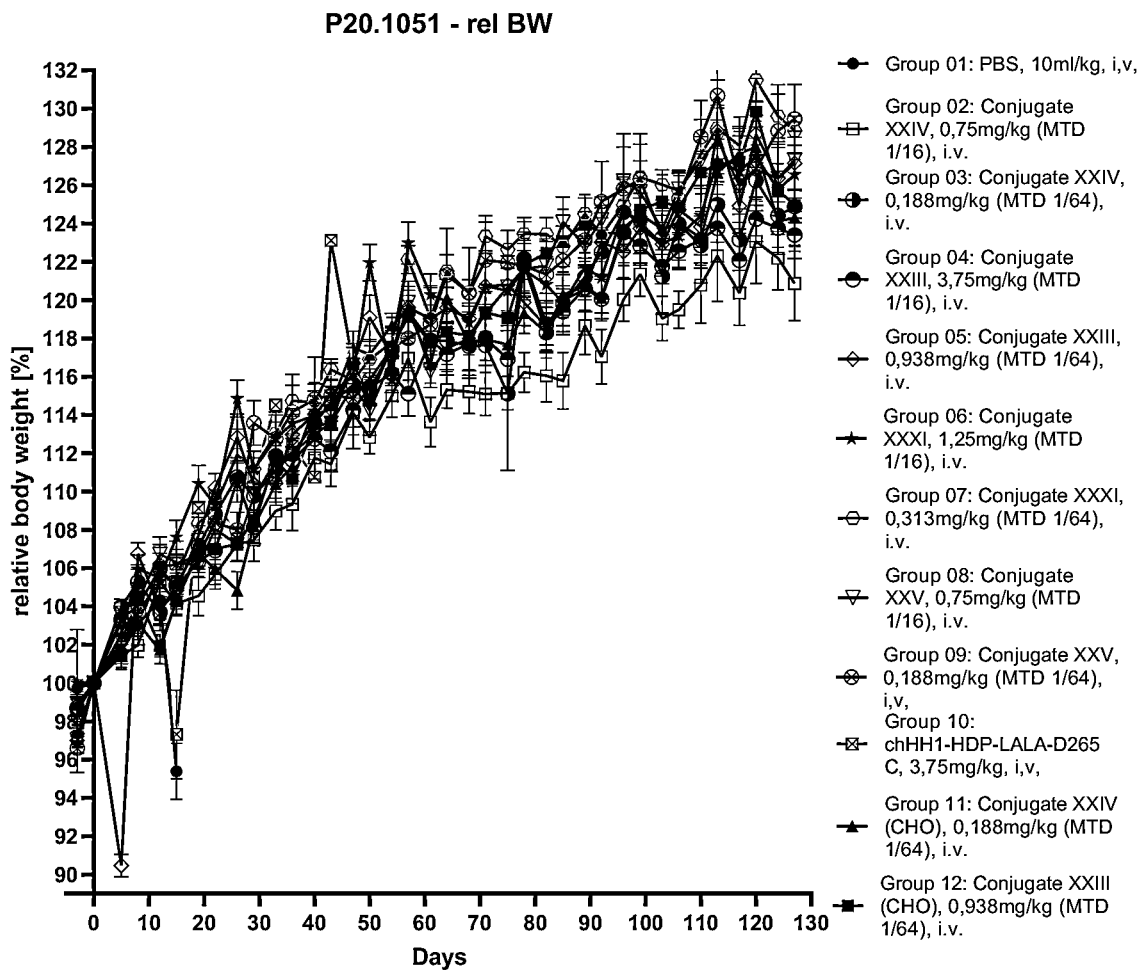
FIG. 10. Results of cytotoxic efficacy studies in vivo using various anti-CD37 amatoxin conjugates in a disseminated Raji-Luc tumor xenograft model over 130 days of treatment showing the body weight of the individual treatment groups Body weight.
Figure 11:
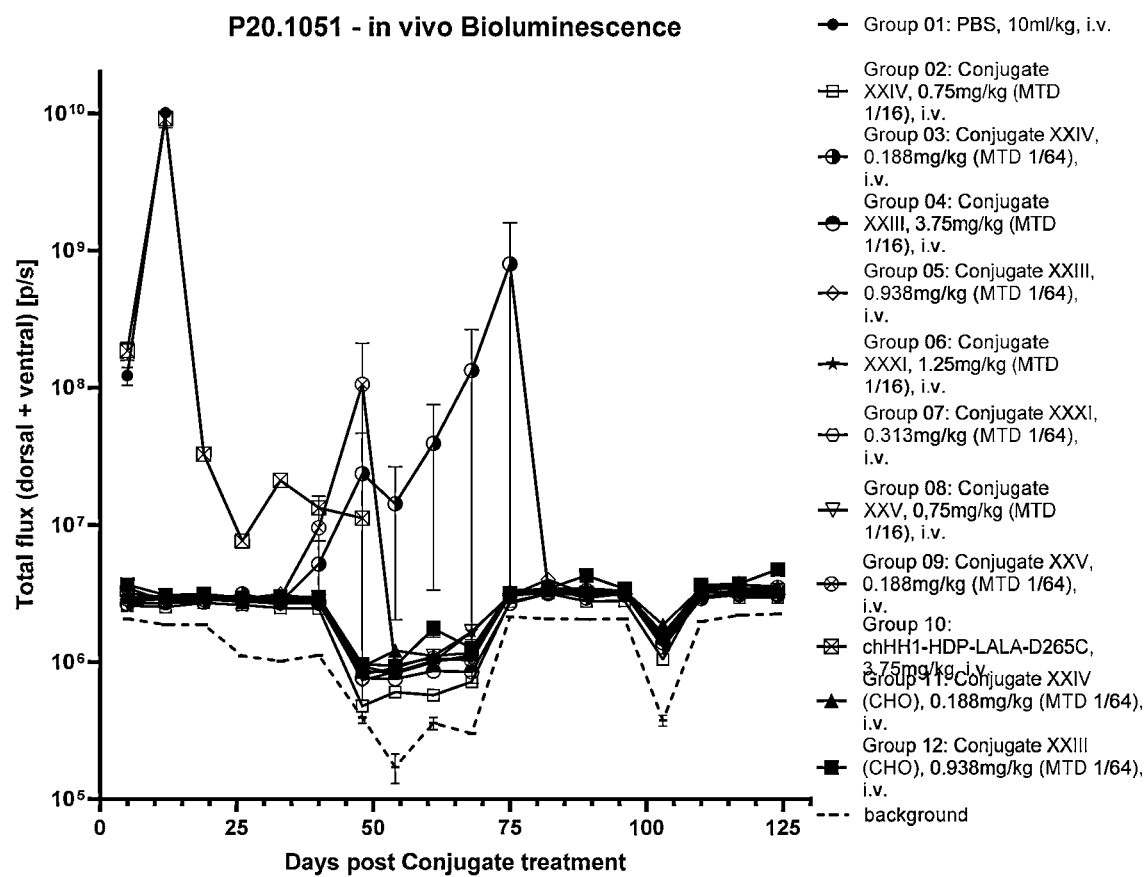
FIG. 11. Results of cytotoxic efficacy studies in vivo using various anti-CD37 amatoxin conjugates in a disseminated Raji-Luc tumor xenograft model over 125 days of treatment: Bioluminesce (background normalized).

Study Outline:

Tumor cell inoculation was done on day −3 by i.v. injection of $2.5 \times 10^6$ MEC-2 cells in CB17 Scid mice. Treatment was performed on day 0 by single dose i.v.

injection at maximum tolerable dose (MTD) of 1/8 and MTD of 1/16 doses, respectively. Readout of the study was body weight and survival. Results are shown in FIG. 10 (body weight) and FIG. 11 (survival) at day 138 after treatment. All groups treated with conjugate gained body weight as normal, in contrast to the control group.

TABLE 4

Study groups of the cytotoxic efficacy study in disseminated MEC-2 tumor xenograft model; roman numerals refer to the amatoxin conjugate as disclosed herein.

| Group | Treatment | Dose protein [mg/kg] | Schedule | Alive animals |
|---|---|---|---|---|
| 1 | PBS (Control) | 10 mL/kg | i.v. single dose | 0/10 |
| 2 | Conjugate XXIV | 2.5 (MTD 1/8) | i.v. single dose | 6/10 |
| 3 | Conjugate XXIV | 1.25 (MTD 1/16) | i.v. single dose | 4/10 |
| 4 | chHH1-HDP-D265C-(XII) | 10 (MTD 1/8) | i.v. single dose | 10/10 |
| 5 | chHH1-HDP-D265C-(XII) | 5 (MTD 1/16) | i.v. single dose | 8/10 |
| 6 | Conjugate XXXI | 3.75 (MTD 1/8) | i.v. single dose | 7/10 |
| 7 | Conjugate XXXI | 1.88 (MTD 1/16) | i.v. single dose | 7/10 |
| 8 | Conjugate XXV | 1.88 (MTD 1/8) | i.v. single dose | 9/10 |
| 9 | Conjugate XXV | 0.94 (MTD 1/16) | i.v. single dose | 8/10 |
| 10 | chHH1-HDP-LALA-D265C | 10 | p.o. single dose | n.a. |
| 11 | Ibrutinib | 25 | p.o. 5×/w for 3 weeks | 0/10 |

Treatment groups are defined in Table 4. Group 10 (chHH1-HDP-LALA-D265C, p.o., single dose; 10 mg/kg) was excluded from analysis. Group 11 (Ibrutinib) was treated with Ibrutinib p.o. 5×/w for 3 weeks at a dose 25 mg/kg.

Abbreviations used: "chHH1-HDP-LALA-D265C" refers to the unconjugated antibody comprising heavy and lights chains each comprising an amino acid sequence according to SEQ ID NO: 11 and SEQ ID NO: 12. "chHH1-HDP-D265C" refers to the unconjugated anti-CD37 antibody comprising heavy and lights chains each comprising an amino acid sequence according to SEQ ID NO: 10 and SEQ ID NO: 12. Suffixes in the form of e.g. -(XII) to an antibody such as chHH1-HDP-D265C refers to the respective amatoxin-linker conjugate linked as disclosed herein to said antibody.

Example 4.2: Cytotoxic Efficacy of Anti-CD37 Amatoxin Conjugates in Disseminated Raji-Luc Tumor Xenograft Model Cytotoxic efficacy studies in vivo were performed using various anti-CD37 antibody amatoxin conjugates in a disseminated Raji-Luc tumor xenograft model over 89 days of treatment.

Figure 12:
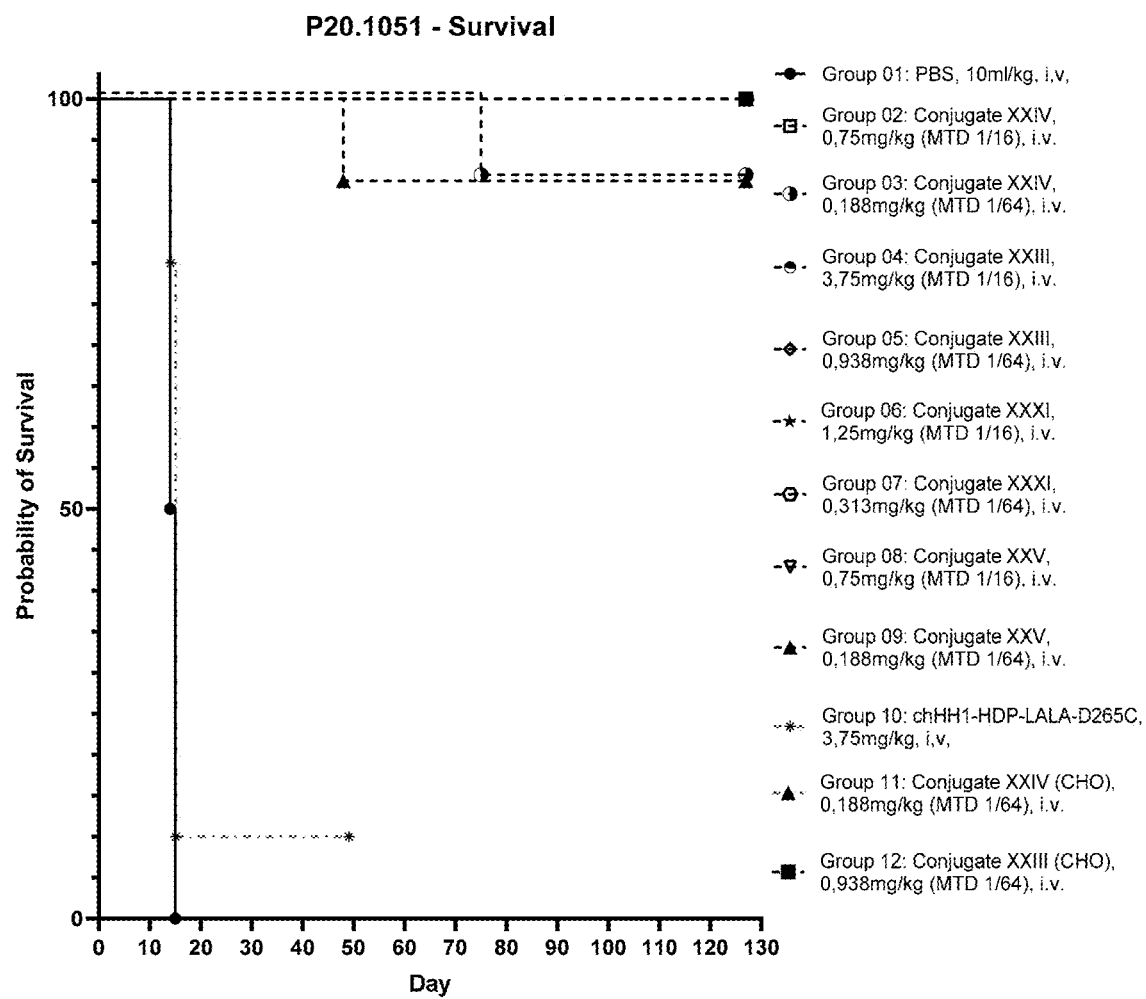
Figure 13A:
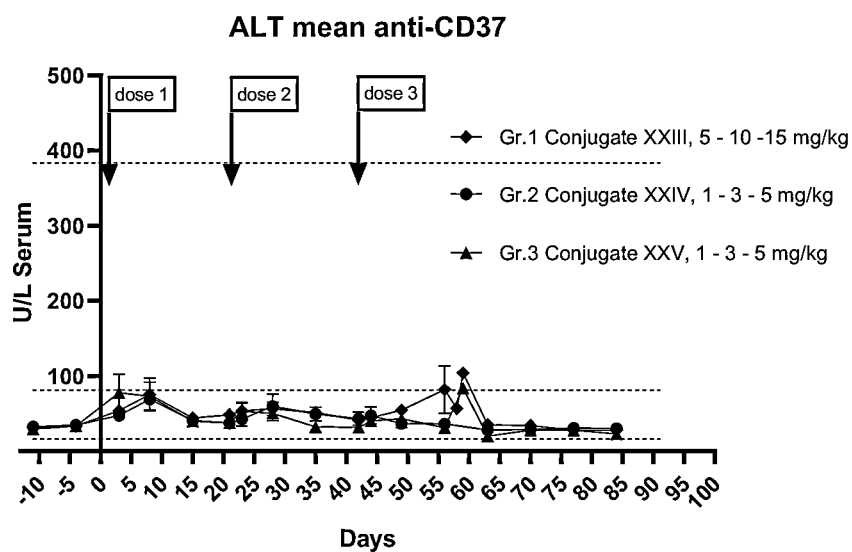
Figure 13B:
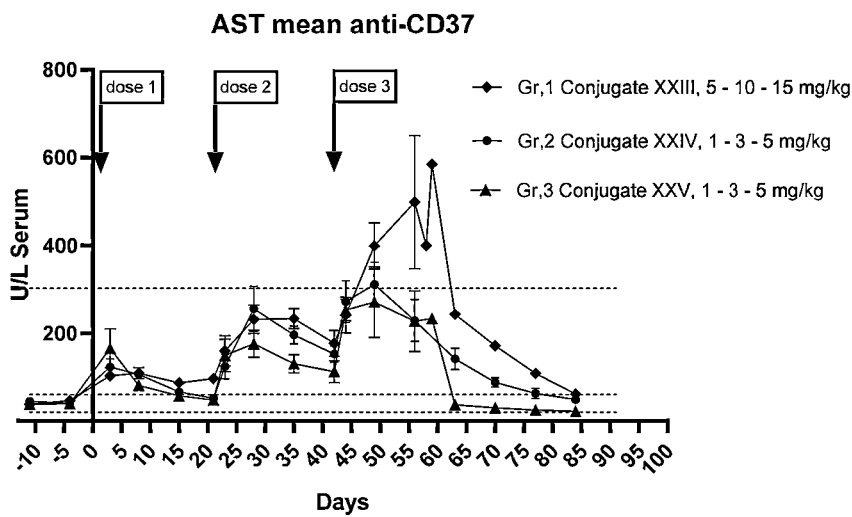
Figure 13C:
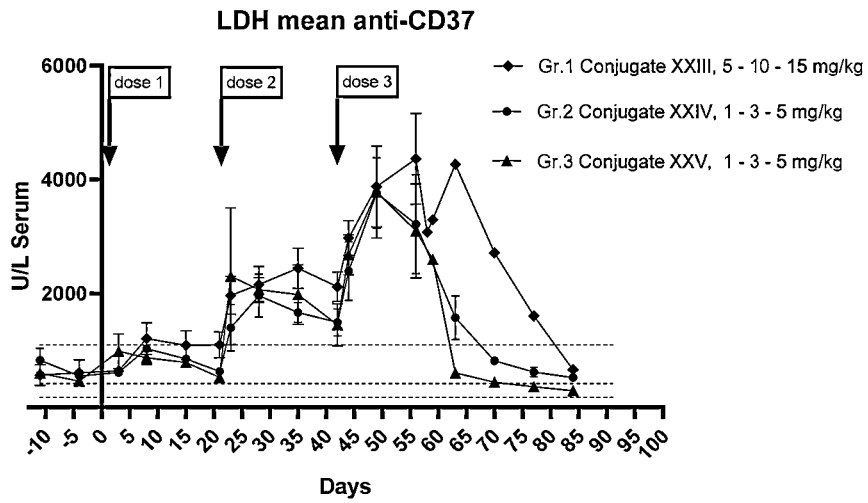
Figure 13D:
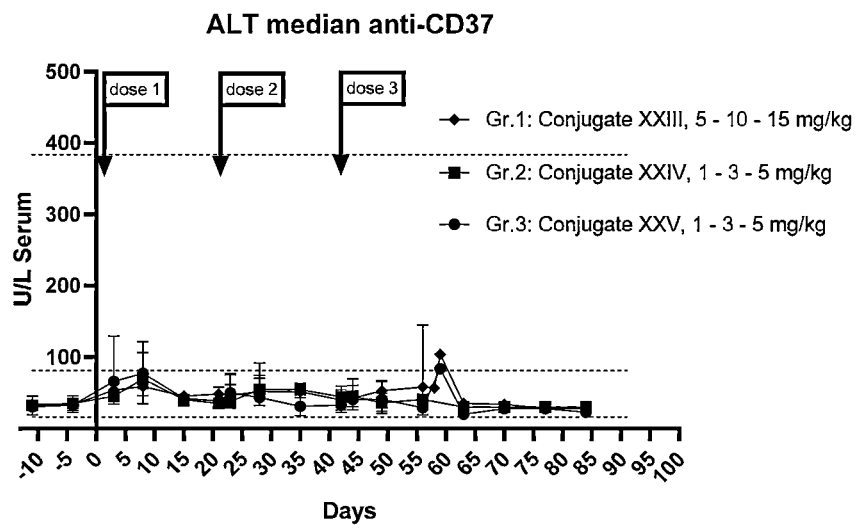
Figure 13E:
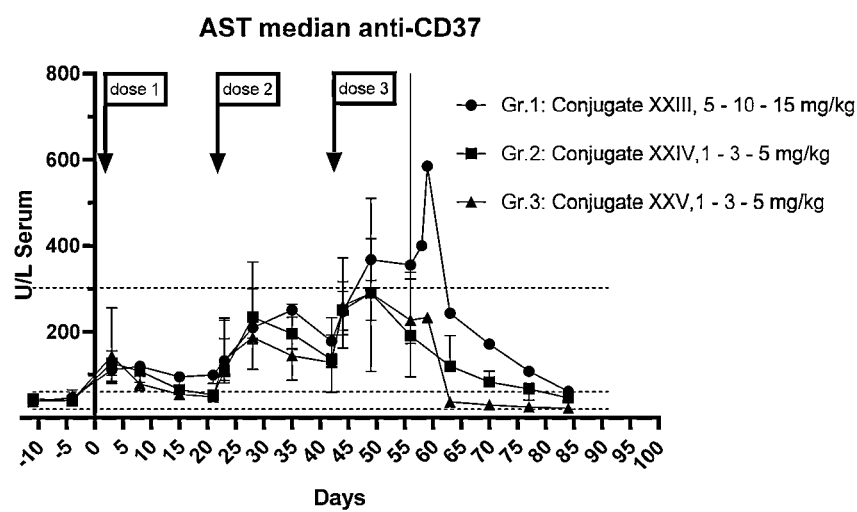
Figure 13F:
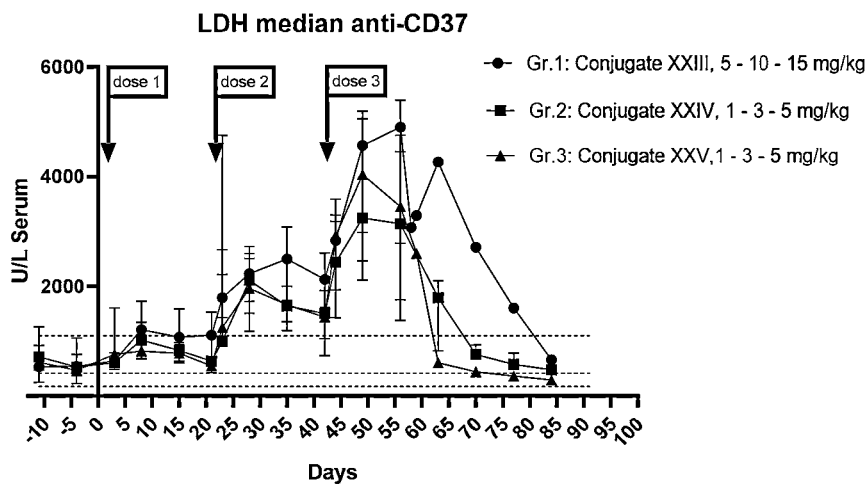
Figure 14A:
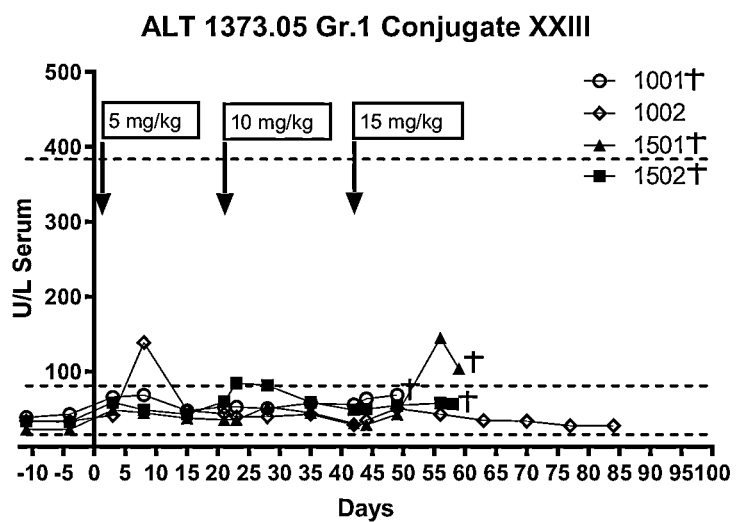
Figure 14B:
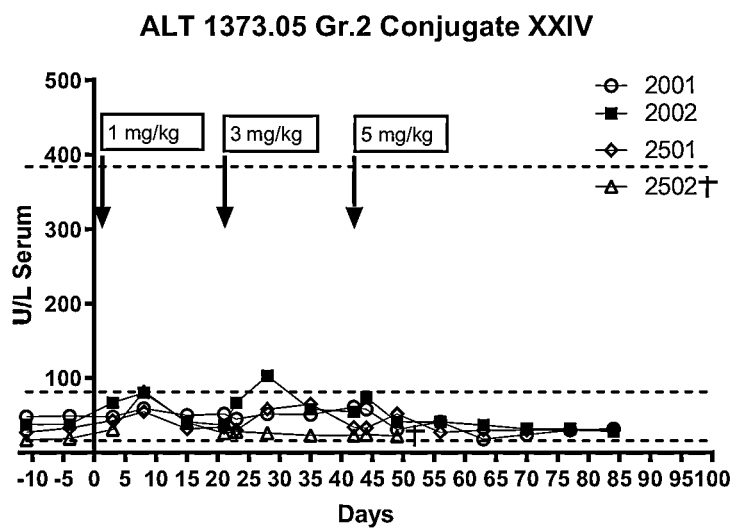
Figure 14C:
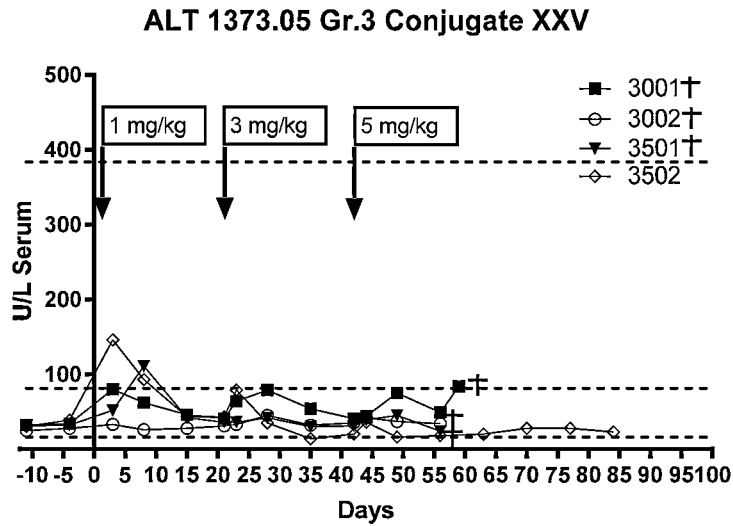
Figure 14D:
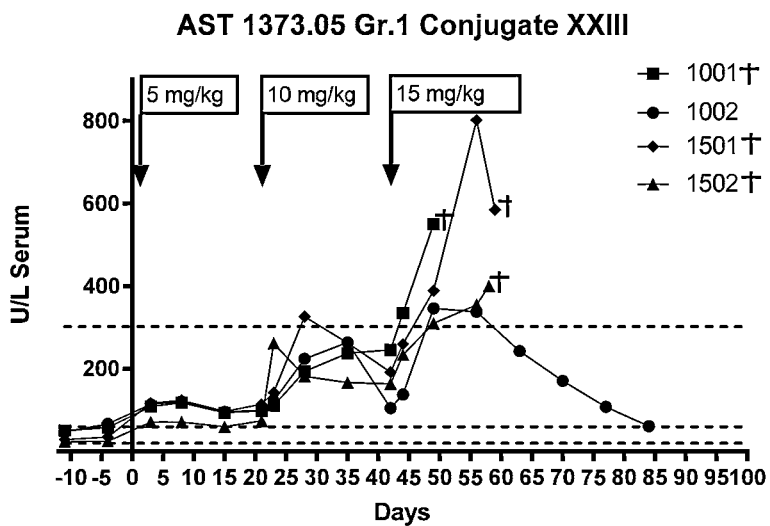
Figure 14E:
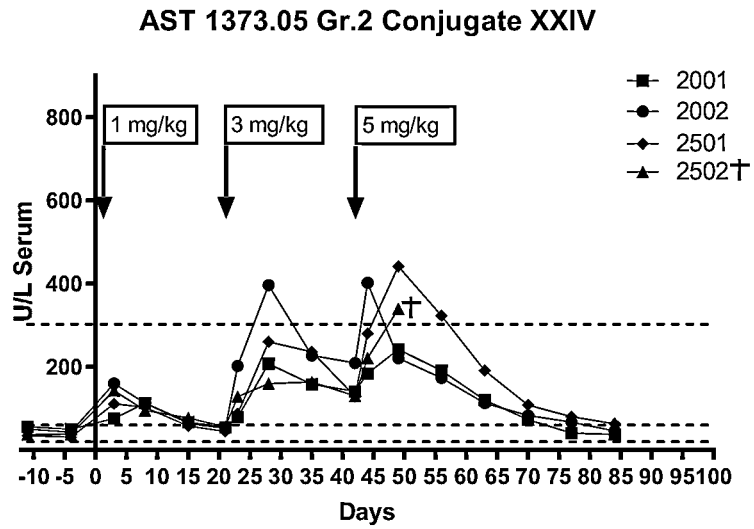
Figure 14F:
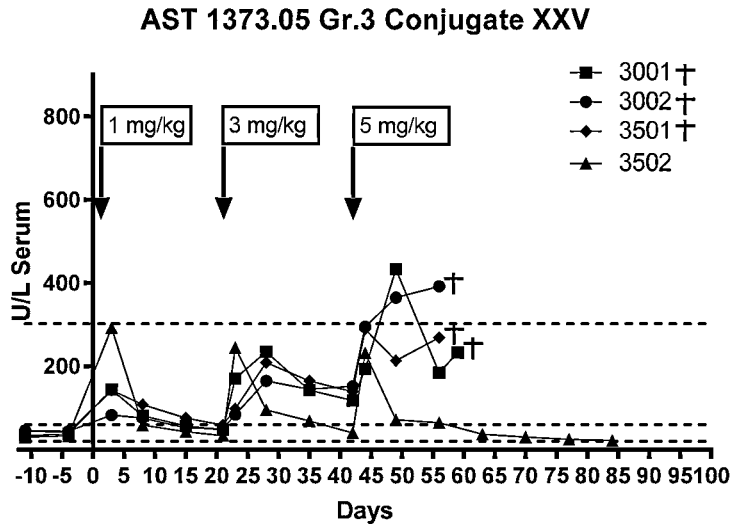
Figure 14G:
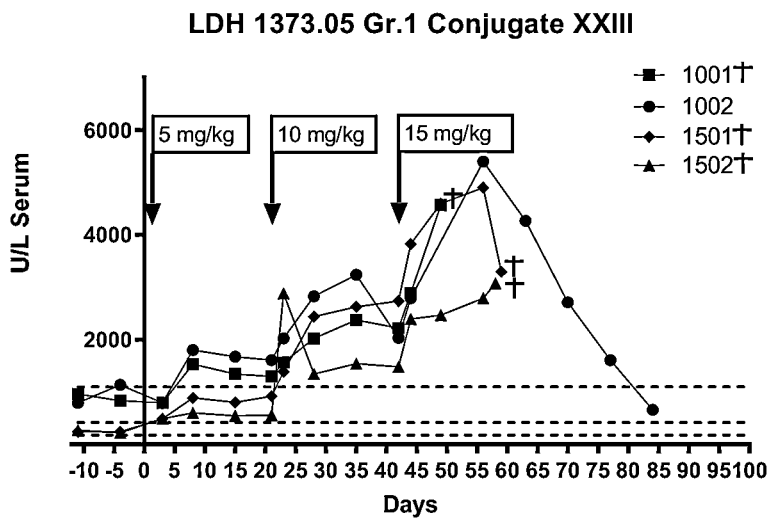
Figure 14H:
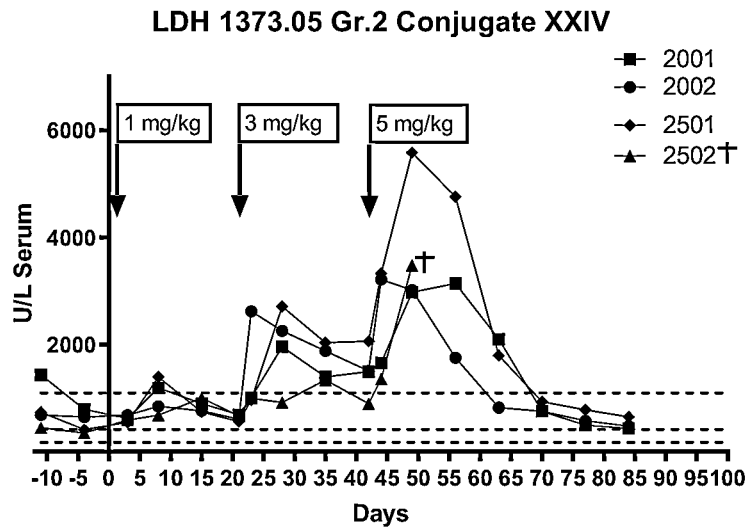
Figure 14I:
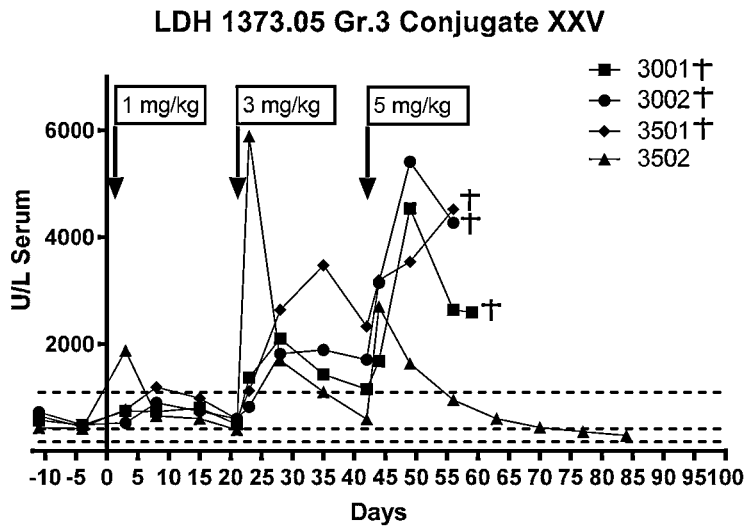

Study Outline:

Tumor cell inoculation was done on day −3 by i.v. injection of 2.5×10$^6$ Raji-Luc cells in CB17 Scid mice. Treatment was performed on day 0 by single dose i.v. injection at maximum tolerable dose (MTD) of 1/16 and MTD of 1/64 doses of cynomolgus MTD, respectively. Readout of the study was body weight, bioluminescence and survival. Results are shown in FIG. 10 (body weight), FIG. 11 (bioluminescence) and FIG. 12 (survival) at day 89 after treatment. All groups treated with conjugate gained body weight as normal, in contrast to the control group.

Treatment groups are as defined in Table 5.

TABLE 5

Study groups of the cytotoxic efficacy study in disseminated Raji-Luc tumor xenograft model.

| Group | Treatment | Dose protein [mg/kg] | Alive animals |
|---|---|---|---|
| 1 | PBS (Control) | — | 0/10 |
| 2 | Conjugate XXIV | 0.75 (MTD 1/16) | 10/10 |
| 3 | Conjugate XXIV | 0.188 (MTD 1/64) | 9/10 |
| 4 | Conjugate XXIII | 3.75 (MTD 1/16) | 10/10 |
| 5 | Conjugate XXIII | 0.938 (MTD 1/64) | 10/10 |
| 6 | Conjugate XXXI | 1.25 (MTD 1/16) | 10/10 |
| 7 | Conjugate XXXI | 0.313 (MTD 1/64) | 10/10 |
| 8 | Conjugate XXV | 0.75 (MTD 1/16) | 10/10 |
| 9 | Conjugate XXV | 0.188 (MTD 1/64) | 9/10 |
| 10 | chHH1-HDP-HDP-LALA-D265C | 3.75 | 0/10 |
| 11 | Conjugate XXIV (CHO) | 0.188 (MTD 1/64) | 10/10 |
| 12 | Conjugate XXIII (CHO) | 0.938 (MTD 1/64) | 10/10 |

In summary, disseminating mouse xenograft tumor models (MEC-2 and Raji-Luc) and CD37-positive patient derived xenograft (PDX; Richter's Syndrome) models were performed in single-dose experiments.

In the mouse xenograft models, 80-100% overall survival for the full duration of the studies (>100 days) were achieved with two anti-CD37 ATACs with 1/16 MTD in MEC-2 model and 1/64 MTD in Raji-Luc model. Single-dose treatment with doses as low as 0.1 mg/kg caused rapid and complete tumor remission 7 days after treatment. The tolerability of the tested ATACs in mice was shown to be >15 mg/kg.

Example 5: Exploratory Toxicity Study with Anti-CD37 Amatoxin Conjugates in *Cynomolgus* Monkeys Exploratory toxicity study in Cynomolgus monkeys (*Macaca fascicularis*) was performed using different anti-CD37 antibody-amatoxin conjugates.

Figure 15A:
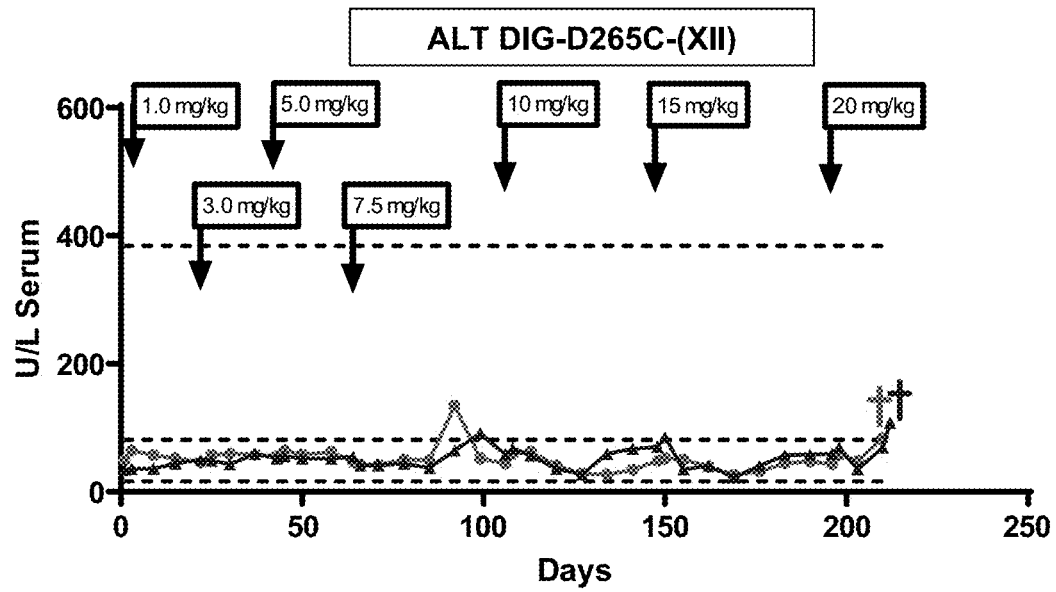
Figure 15B:
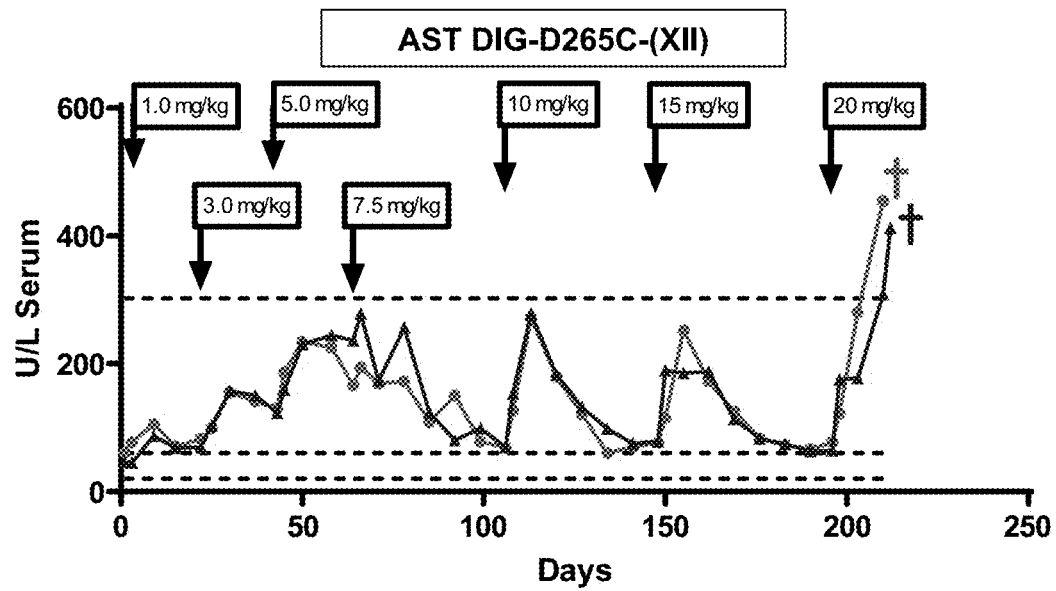
Figure 15C:
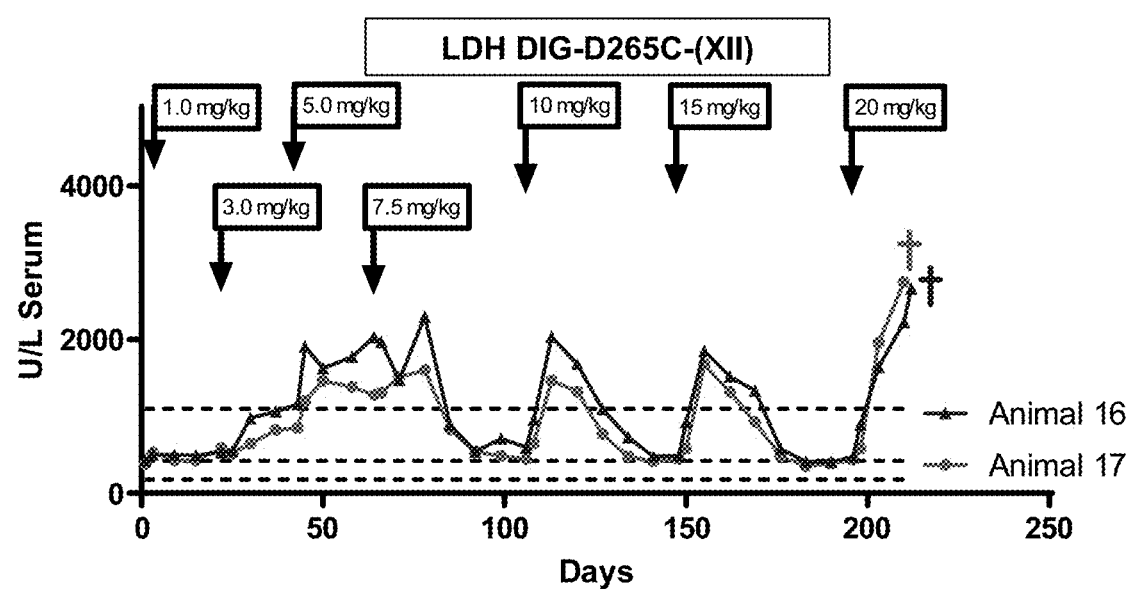

Three monkeys were assigned per group (3 kg body weight). Anti-CD37 monoclonal antibody expressed in CHO cells was used for conjugation with different amatoxin-linker constructs. Three groups were assigned and dosed as follows:

Conjugate XXIII: 5 mg/kg, 10 mg/kg, 15 mg/kg
Conjugate XXIV: 1 mg/kg, 3 mg/kg, 5 mg/kg
Conjugate XXV: 1 mg/kg, 3 mg/kg, 5 mg/kg Results regarding alanine transaminase (ALT) assessment, aspartate trans-aminase (AST) assessment, and lactate dehydrogenase (LDH) assessment are shown in FIGS. 13-15.

The antibody used in this study is not cross-reactive to CD37 in animals, including non-human primates (NHP). Therefore, the linker-amanitin derivative was conjugated to a non-binding anti-DIG antibody. This anti-DIG conjugate revealed a good tolerability indicating a low off target toxicity in NHP. Hematology and clinical chemistry parameters were unaffected except liver transaminases and LDH; a mild to moderate and transient increase was observed.

In conclusion, targeted cytotoxic drug delivery to CD37-positive cell lines was achieved by using anti-CD37 antibody-targeted amatoxin conjugates (ATACs). The mode of action of the payload amanitin led to an efficient anti-tumor potential in vitro and in vivo with good tolerability in non-human primates. The experimental data shown suggest using ATACs in the therapy of B-cell lymphomas and other B-cell-associated malignancies, including malignancies that underwent Richter's transformation, as a promising approach.

Example 6: Exploratory Toxicity Study with Anti-CD37 Amatoxin Conjugates in a Richter's Syndrome (RS) Patient-Derived Xenograft (PDX) Model Study Outline:

The patient-derived xenograft (PDX) model for Richter's syndrome were adapted from *Cancer Res* (2018); 78(13); 3413-20 with modifications.

Briefly, a total of $2 \times 10^7$ primary Richter syndrome cells from peripheral blood or lymph nodes were resuspended in Matrigel (BD Biosciences) and subcutaneously injected (double flank) in 8-week old CB17 Scid mice immunocompromised mice and left to engraft. Tumor masses were then collected, partially disrupted, and tumor cells reinjected as a single-cell suspension in Matrigel. These steps were repeated several times to obtain stable models of Richter syndrome.

Figure 16A:
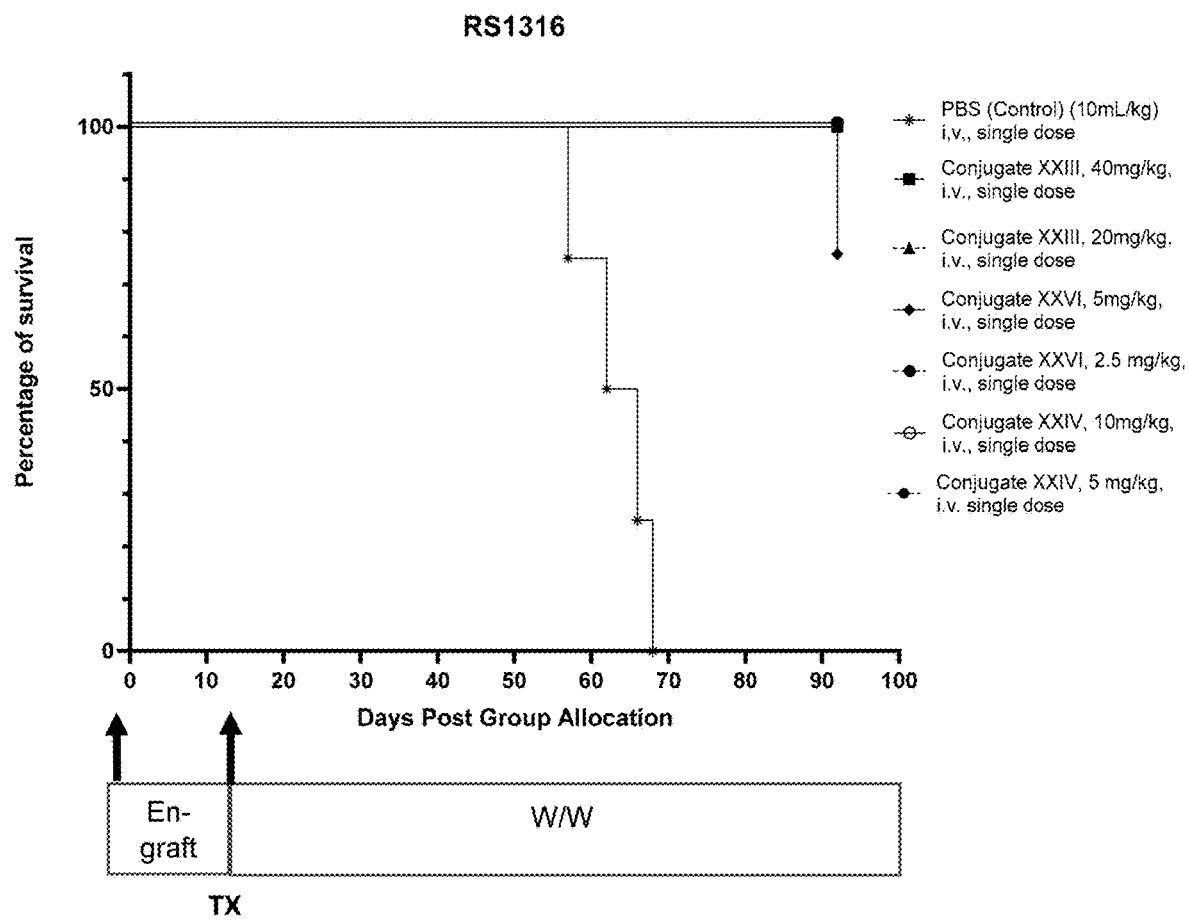

For the intravenous model, $10^7$ Richter syndrome cells purified from tumor masses were resuspended in PBS and injected in the tail vein of the mice. Groups of n=4 mice each were treated 15 days post engraftment as indicated in FIG. 16A. Mice were injected with a single dose of the conjugates XXIII, XXIV, or XXVI as indicated. All mice within the PBS control group died within 68 days post engraftment. One animal in the group receiving conjugate XXVI at a dose of 5 mg/kg i.v. died at day 90 post engraftment. The results indicate that treatment with a single dose of conjugates XXIII, XXIV, XXVI is well tolerated at different doses and effective in treating RS.

Assessment of Residual RS Disease Activity in Organs

Figure 16B:
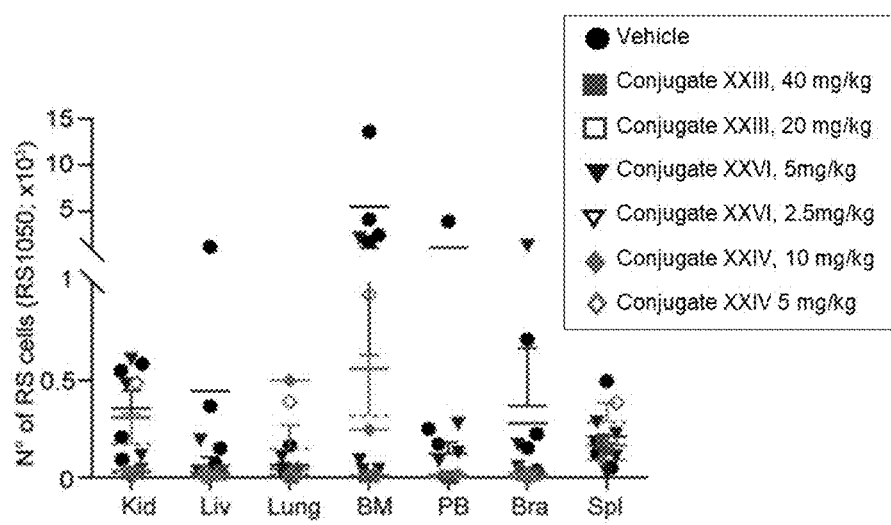

To assess residual RS disease activity in the organs of engrafted animals mice were euthanized and peripheral blood and organs (kidneys, spleen, bone marrow, lung, liver, and brain) collected and disease spread evaluated by flow cytometry, using anti-human antibodies (CD45PerCPCy5.5/CD19APC/CD20FITC). Results are depicted in FIG. 16B indicating that a single dose of a conjugate of the invention can significantly reduce (in the case of conjugate XXIV, 5 mg), or even eliminate RS disease activity from organs of engrafted animals.

Example 7: Assessment of Crossreactivity of Anti-CD37 Antibody

Cross reactivity of the anti-CD37 chHH1-HDP-LALA-D265C with cynomolgus peripheral blood mononuclear cells (PBMCs) was assessed by flow cytometry. As control, human PBMCs were stained using the same set of antibodies. FACS analysis was done according to a standard protocol. In brief: PBMCs were resuspend in 300 µL staining medium ($3.3 \times 10^5$ cells/50 µl staining medium). 50 µl cell suspension for each sample (=$3.3 \times 10^5$ cells per sample) were pipetted into one well of an U-well plate. 50 µl of pre-diluted isotype and antibody solutions were added to the samples in each well and incubated for 30 min on ice, followed by the addition of 100 µl ice-cold PBS and centrifugation at 4° C., 300 g, 6 min. The resulting supernatant was discarded and cells were washed with 200 µl ice-cold PBS, pH 7.4 followed by centrifugation at 4° C., 300 g, 6 min. The wash step was repeated once. The supernatant was discarded and cells resuspended in 100 µl of the secondary antibody solution. For the untreated sample (control) 100 µl staining medium were used. Cells were incubated for 30 min on ice protected from light. 100 µl ice-cold PBS were added and cells were centrifuge at 4° C., 300 g, 6 min. The supernatant was discarded and cells were washed twice with 200 µl ice-cold PBS, pH 7.4 and centrifuged at 4° C., 300 g, 6 min. Subsequently the supernatant was discarded and cells resuspend cells in 200 µl freshly prepared fixation solution. Cells were stored in fixation solution at 4° C. protected from light until analysis in BD FACSLyric device using FACSuite Software. The results are depicted in FIG. 17 indicating that chHH1-HDP-LALA-D265C does not exhibit specific binding to cynomolgus CD37.

Antibodies used:
anti-human CD37 chHH1-HDP-LALA-D265C 10.0 mg/ml, stored at 4° C., diluted to 100 µg/ml in staining medium (1 µl antibody dilution+99 µL staining medium);
mouse anti-human CD37 (Novus Biologicals) stored at −20° C., 1:100 dilution in staining medium (1 µl antibody dilution+99 µL staining medium)
Goat anti-Human IgG (Fc)-AlexaFluor488 Fab: 1.5 mg/ml (Jackson Immuno; 109-546-008) (Storage: −70° C.)
Goat anti-mouse IgG (Fc)-AlexaFluor488 F(ab)2-Fragment: 1.5 mg/ml (in vitrogen: A11001)
Staining medium: RPMI 1640, 25 mM HEPES, 3% FCS, 0.02% Na-Azid
Fixation solution: 2% Paraformaldehyde in PBS

REFERENCES

Bargh et al. (2019) Cleavable linkers in antibody-drug conjugates Chem Soc Rev. August 12; 48(16):4361-4374.

Beckwith K A et al. (2014). The CD37-targeted antibody-drug conjugate IMGN529 is highly active against human CLL and in a novel CD37 transgenic murine leukemia model. *Leukemia*. Vol. 28(7): 1501-1510.

Belov L et al. (2001) Immunophenotyping of Leukemias Using a Cluster of Differentiation Antibody Microarray. *Cancer Research* Vol. 61: 4483-4489.

Brown J R (2018). How I treat CLL patients with ibrutinib. *Blood* Vol. 131(4): 379-386.

Buchman, A. R., et al. (1988) Comparison of intron-dependent and intron-independent gene expression. Mol. Cell. Biol. 8: 4395-4405

Costa, R. A., et al. (2010) Guidelines to cell engineering for monoclonal antibody production. Eur. J. Pharmaceut. Biopharmaceut. 74:127-138

Cothia & Lesk, (1987) Canonical structures for the hypervariable regions of immunoglobulins. J Mol Biol. August 20; 196(4):901-17

Deckert J et al. (2013). A novel anti-CD37 antibody-drug conjugate with multiple anti-tumor mechanisms for the treatment of B-cell malignancies. *Blood* Vol. 122(20): 3500-3510.

Edelman, G. M. et al., *Proc. Natl. Acad. USA,* 63, 78-85 (1969). The covalent structure of an entire gammaG immunoglobulin molecule.

English et al. (2020) Ancient species offers contemporary therapeutics: an update on shark VNAR single domain antibody sequences, phage libraries and potential clinical applications. *Antibody Therapeutics,* Vol. 3, No. 11-9

Fuhrman et al. (2014). Ibrutinib Resistance in Chronic Lymphocytic Leukemia. *N Engl J Med.* doi:10.1056/NEJMc1402716

George B et al. (2020). Ibrutinib Resistance Mechanisms and Treatment Strategies for B-Cell Lymphomas. *Cancers* Vol. 12: 1328; doi:10.3390/cancers12051328.

Hemler M E (2001). Specific tetraspanin functions. *The Journal of Cell Biology* Vol. 155(7): 1103-1107.

Iyer S et al. (1997). Quantibrite: A New Standard for Fluorescence Quantitation. *Becton Dickinson Immunocytometry Systems,* San Jose, CA White Paper.

Jäger et al. (2013) High level transient production of recombinant antibodies and antibody fusion proteins in HEK293 cells. BMC Biotechnology 13:52

Junutula J R et al. (2008). Site-specific conjugation of a cytotoxic drug to an antibody improves the therapeutic index. *Nat Biotechnology* Vol. 26: 925-932.

Kabat E A, Wu T T, Bilofsky H., et al., Sequence of Proteins of Immunological Interest, National Institutes of Health, Bethesda (1983))

Kamle et al (2022) Methods for transient expression and purification of monoclonal antibodies in mammalian cells. Advances in Protein Molecular and Structural Biology Methods p. 31-39

Kim, D. W., et al. (1990) Use of the human elongation factor 1 alpha promoter as a versatile and efficient expression system. Gene 91: 217-223

Knobeloch K P et al. (2000). Targeted inactivation of the tetraspanin CD37 impairs T-cell-dependent B-cell response under suboptimal costimulatory conditions. *Mol Cell Biol.* Vol. 20: 5363-5369.

Lapalombella R et al. (2012). Tetraspanin CD37 directly mediates transduction of survival and apoptotic signals. *Cancer Cell* Vol. 21(5): 694-708.

Lefranc et al. (2003) IMGT unique numbering for immunoglobulin and T cell receptor variable domains and Ig superfamily V-like domains. Dev Comp Immunol. 27:55-77.

Link M P et al. (1986). A unique antigen on mature B cells defined by a monoclonal antibody. *J Immunol* Vol. 137(9): 3013-3018.

Merz et al. (2016) Baseline characteristics, chromosomal alterations, and treatment affecting prognosis of deletion 17p in newly diagnosed myeloma. *Am J Hematol.* 2016 November; 91(11):E473-E477.

Pillow et al. (2017) Decoupling stability and release in disulfide bonds with antibody-small molecule conjugates. Chem. Sci., 8, 366-370.

Pula B et al. (2019). Overcoming Ibrutinib Resistance in Chronic Lymphocytic Leukemia. *Cancers* Vol. 11: 1834; doi:10.3390/cancers11121834.

Saiz M L et al. (2018). Tetraspanins as Organizers of Antigen-Presenting Cell Function. *Frontiers in Immunology* Vol. 9: Article 1074.

Schwartz-Albiez R et al. (1988). The B cell-associated CD37 antigen (gp40-52). Structure and subcellular expression of an extensively glycosylated glycoprotein. *J Immunol.* Vol. 140(3): 905-914.

Smeland E et al. (1985). Characterization of Two Murine Monoclonal Antibodies Reactive with Human B Cells. *Scand. J Immunol.* Vol. 21: 205-214.

Spangler et al. (2018) Toward a Ferrous Iron-Cleavable Linker for Antibody-Drug Conjugates. Mol Pharm. May 7; 15(5):2054-2059

Stacchini A et al. (1999). MEC1 and MEC2: two new cell lines derived from B-chronic lymphocytic leukaemia in prolymphocytoid transformation. *Leukemia Research* Vol. 23: 127-136.

Stilgenbauer S et al. (2019). Phase 1 first-in-human trial of the anti-CD37 antibody BI 836826 in relapsed/refractory chronic lymphocytic leukemia. *Leukemia* Vol. 33: 2531-2535.

Tsimberidou et al. (2008) Phase I-II study of oxaliplatin, fludarabine, cytarabine, and rituximab combination therapy in patients with Richter's syndrome or fludarabine-refractory chronic lymphocytic leukemia. J Clin Oncol. January 10; 26(2):196-203).

Vaisitti et al. (2018). Novel Richter Syndrome Xenograft Models to Study Genetic Architecture, Biology, and Therapy Responses. Cancer Research Vol. 78: 3413-3420.

Van Spriel A B et al. (2004). A Regulatory Role for CD37 in T Cell Proliferation. *Journal of Immunology* Vol. 172: 2953-2961.

Wieland T et al. (1978). Amatoxins, Phallotoxins, Phallolysin, and Antamanide: The Biologically Active Components of Poisonous Amanita Mushroom. *CRC Crit Rev Biochem.* Vol. 5: 185-260.

Xu-Monette Z Y et al. (2016). Assessment of CD37 B-cell antigen and cell of origin significantly improves risk prediction in diffuse large B-cell lymphoma. *Blood* Vol. 128(26): 3083-3100.

Zhao X et al. (2007). Targeting CD37-positive lymphoid malignancies with a novel engineered small modular immunopharmaceutical. *Blood* Vol. 110(7): 2569-2577.

Zou F et al. (2018). Expression and Function of Tetraspanins and Their Interacting Partners in B Cells. *Frontiers in Immunology* Vol. 9. Article 1606.

What is claimed is:

1. A conjugate comprising (i) a target binding moiety, (ii) at least one toxin, and (iii) at least one linker connecting said target binding moiety with said at least one toxin, wherein
said target binding moiety binds to CD37,
said at least one toxin is an amatoxin,
said target binding moiety is an antibody,
consisting of two heavy chains, each heavy chain comprising an amino acid sequence according to SEQ ID No. 11, and two light chains, each light chain comprising an amino acid sequence according to SEQ ID No. 12, as target binding moiety, conjugated to at least one amatoxin-linker moiety of formula (XII), (XIII), or (XIV) via thioether linkage of the linker with the sulfhydryl group of heavy chain 265Cys residue according to the EU numbering system of said antibody, wherein formula (XII), (XIII), or (XIV) have the structure according to:

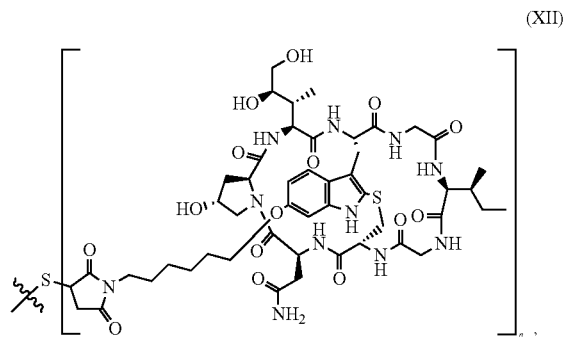

(XII)

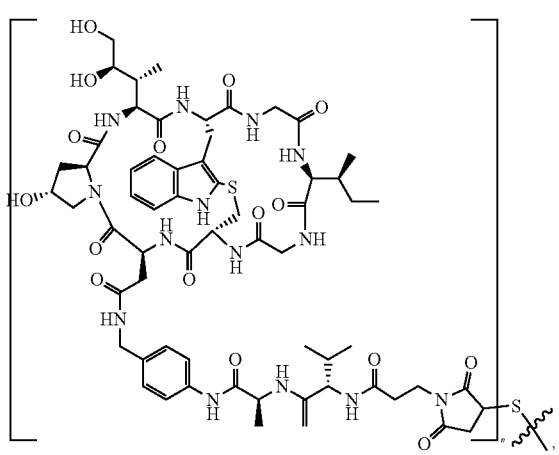

(XIII)

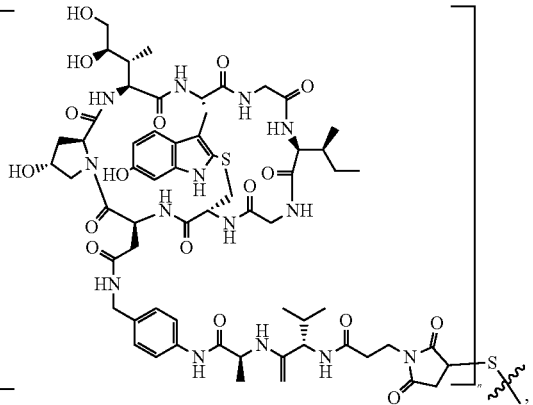

(XIV)

wherein n is 1 or 2.

2. A pharmaceutical composition comprising the conjugate of claim 1.

3. The pharmaceutical composition according to claim 2, further comprising one or more pharmaceutically acceptable buffers, surfactants, diluents, carriers, excipients, fillers, binders, lubricants, glidants, disintegrants, adsorbents, and/or preservatives.

4. A method of treating a patient suffering from a B lymphocyte-associated malignancy or B cell-mediated autoimmune disease, wherein the method comprises administering a therapeutically effective amount of a conjugate according to claim 1 or a pharmaceutical composition comprising said conjugate to said patient.

5. The method of treating a patient according to claim 4, wherein the patient is suffering from Richter syndrome and wherein the method comprises administering a therapeutically effective amount of a conjugate of claim 1 or a pharmaceutical composition comprising said conjugate as monotherapy, or in combination with an immune checkpoint inhibitor.

6. The method of treating a patient according to claim 4, wherein the patient is suffering from non-Hodgkin's lymphoma (NHL), follicular lymphoma, diffuse large B cell non-Hodgkin's lymphoma (DBNHL), subtypes of non-Hodgkin's lymphoma including mantle cell lymphoma (MCL), chronic lymphocytic leukaemia (CLL), Richter syndrome, primary cutaneous marginal zone lymphoma (PCMZL), hairy cell leukemia, acute myeloid leukemia (AML), rheumatoid arthritis, granulomatosis with polyangiitis and microscopic polyangiitis, or pemphigus vulgaris.

7. The method of treating a patient according to claim 4, wherein the method comprises administering a therapeutically effective amount of said conjugate or a pharmaceutical composition comprising said conjugate in combination with an immune checkpoint inhibitor.

8. The method of treating a patient according to claim 4, wherein the B lymphocyte-associated malignancies or B cell-mediated autoimmune diseases are characterized by a hemizygous loss of TP53, POLR2A, or del(17p13).

* * * * *